(12) United States Patent
Kröger et al.

(10) Patent No.: US 7,282,357 B2
(45) Date of Patent: Oct. 16, 2007

(54) METHOD FOR THE PRODUCTION BY FERMENTATION OF SULPHUR-CONTAINING FINE CHEMICALS (METF)

(75) Inventors: Burkhard Kröger, Limburgerhof (DE); Oskar Zelder, Speyer (DE); Corinna Kolpprogge, Mannheim (DE); Hartwig Schröder, Nußloch (DE); Stefan Häfner, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/525,907

(22) PCT Filed: Aug. 26, 2003

(86) PCT No.: PCT/EP03/09451

§ 371 (c)(1),
(2), (4) Date: Feb. 25, 2005

(87) PCT Pub. No.: WO2004/024931

PCT Pub. Date: Mar. 25, 2004

(65) Prior Publication Data

US 2006/0068476 A1   Mar. 30, 2006

(30) Foreign Application Priority Data

Aug. 27, 2002   (DE)   ................ 102 39 308

(51) Int. Cl.
- C12P 13/12   (2006.01)
- C12P 21/06   (2006.01)
- C12N 9/02   (2006.01)
- C12N 9/10   (2006.01)
- C12N 1/20   (2006.01)
- C12N 15/70   (2006.01)
- C07H 21/04   (2006.01)

(52) U.S. Cl. ................. 435/113; 435/189; 435/252.32; 435/193; 435/69.1; 435/471; 536/23.2

(58) Field of Classification Search ................. 435/113, 435/252.32, 69.1, 320.1; 536/23.2
See application file for complete search history.

(56) References Cited

U.S. PATENT DOCUMENTS

| | | | |
|---|---|---|---|
| 4,489,160 A | 12/1984 | Katsumata et al. | |
| 4,601,893 A | 7/1986 | Cardinal | |
| 5,158,891 A | 10/1992 | Takeda et al. | |
| 5,175,108 A | 12/1992 | Bachmann et al. | |
| 5,965,391 A | 10/1999 | Reinscheid et al. | |
| 2003/0170775 A1 | 9/2003 | Pompejus et al. | |

FOREIGN PATENT DOCUMENTS

| | | |
|---|---|---|
| DE | 10046870 A1 | 3/2002 |
| EP | 0472869 A2 | 3/1992 |
| EP | 1108790 A2 | 6/2001 |
| JP | 10-229891 A | 9/1998 |
| WO | WO-93/17112 | 9/1993 |
| WO | WO-96/15246 A1 | 5/1996 |
| WO | WO-02/10206 | 2/2002 |
| WO | WO-03/087386 A3 | 10/2003 |
| WO | WO-03/100072 A2 | 12/2003 |
| WO | WO-2004/024932 | 3/2004 |
| WO | WO-2004/024933 | 3/2004 |

OTHER PUBLICATIONS

U.S. Appl. No. 10/511,302, Kröger et al.
Krämer, R., "Genetic and physiological approaches for the production of amino acids", Journal of Biotechnology, vol. 45, 1996, pp. 1-21.
Matthews, R. G., et al., "Methylenetetrahydrofolate reductase and methionine synthase: biochemistry and molecular biology", Eur. J. Pediatr., vol. 157, Suppl. 2, 1998, pp. S54-S59.
Trimmer, E. E., et al., "Methylenetetrahydrofolate Reductase from *Escherichia coli*: Elucidation of the Kinetic mechanism by Steady-State and Rapid-Reaction Studies", Biochemistry, vol. 40, 2001, pp. 6205-6215.
Matthews, R. G., "Methylenetetrahydrofolate Reductase from Pig Liver", Methods in Enzym, 122, 372, 1986, Enzymology, vol. 122, pp. 372-381.
Sahm, H., et al., "Pathway Analysis and Metabolic Engineering in *Corynebacterium glutamicum*", Biol. Chem., vol. 381, 2000, pp. 899-910.
Eikmanns, B. J., et al., "Molecular Aspects of lysine, threonine, and isoleucine biosynthesis in *Corynebacterium glutamicum*", Atonie van Leeuwenhoek, vol. 64, 1993, pp. 145-163.
Pearson, W. R., et al., "Improved tools for biological sequence comparison", Proc. Natl. Acad. Sci. USA, vol. 85, 1988, pp. 2444-2448.
Narang, S. A., "Tetrahedron Report No. 140—DNA Synthesis", Tetrahedron, vol. 39, No. 1, 1983, pp. 3-22.
Itakura, K., et al., "Synthesis and Use of Synthetic Oligonucleotides", Ann. Rev. Biochem., vol. 53, 1984, pp. 323-356.
Itakura, K., et al., "Expression in *Escherichia coli* of a Chemically Synthesized Gene for the Hormone Somatostatin", Science, vol. 198, 1977, pp. 1056-1063.
Ike, Y., et al., "Solid phase synthesis of polynucleotides. VIII. Synthesis of mixed oligodeoxyribonucleotides by the phosphotriester solid phase method", Nucleic Acids Research, vol. 11, No. 2, 1983, pp. 477-488.
Arkin, A. P., et al., "An algorithm for protein engineering: Simulations of recursive ensemble mutagenesis", Proc. Natl. Acad. Sci., USA, vol. 89, 1992, pp. 7811-7815.

(Continued)

*Primary Examiner*—Rebecca E. Prouty
*Assistant Examiner*—Iqbal Chowdhury
(74) *Attorney, Agent, or Firm*—Connolly Bove Lodge & Hutz LLP

(57) ABSTRACT

The invention relates to methods for the fermentative production of sulfur-containing fine chemicals, in particular L-methionine, by using bacteria which express a nucleotide sequence coding for a methionine synthase (metF) gene.

17 Claims, 3 Drawing Sheets

OTHER PUBLICATIONS

Delagrave, S., et al., "Recursive ensemble mutagenesis", Protein Engineering, vol. 6, No. 3, 1993, pp. 327-331.

Kohara, Y., et al., "The Physical Map of the Whole E. coli Chromosome: Application of a New Strategy for Rapid Analysis and Sorting of a Large Genomic Library", Cell, vol. 50, 1987, pp. 495-508.

Wahl, G. M., et al., "Cosmid vectors for rapid genomic walking, restriction mapping, and gene transfer", Proc. Natl. Acad. Sci. USA, vol. 84, 1987, pp. 2160-2164.

Bolivar, F., "Molecular Cloning Vectors Derived From The CoLE1 Type Plasmid pMB1", Life Sciences, vol. 25, 1979, pp. 807-817.

Vieira, J., et al., "The pUC plasmids, an M13mp7-derived system for insertion mutagenesis and sequencing with synthetic universal primers", Gene, vol. 19, 1982, pp. 259-268.

Grant, S. G. N., et al., "Differential plasmid rescue from transgenic mouse DNAs into *Escherichia coli* methylation-restriction mutants", Proc. Natl. Acad. Sci. USA, vol. 87, 1990, pp. 4645-4649.

Sanger, F., et al., "DNA sequencing with chain-terminating inhibitors", Proc. Natl. Acad. Sci. USA, vol. 74, No. 12, 1977, pp. 5463-5467.

Staden, R., "The current status and portability of our sequence handling software", Nucleic Acids Research, vol. 14, No. 1, 1986, pp. 217-231.

Marck, C., "DNA Strider: a 'C' program for the fast analysis of DNA and protein sequences on the Apple Macintosh family of computers", Nucleic Acids Research, vol. 16, No. 5, 1988, pp. 1829-1836.

Butler, B. A., "Sequence Analysis Using GCG", Methods of Biochemical Analysis, vol. 39, 1998, pp. 74-97.

Liebl, W., et al., "Transfer of *Brevibacterium divaricatum* DSM 20297$^T$, *"Brevibacterium flavum"* DSM 20411, *"Brevibacterium lactofermentum"* DSM 20412 and DSM 1412, and *Corynebacterium lilium* DSM 20137$^T$ to *Corynebacterium glutamicum* and Their Distinction by rRNA Gene Restriction Patterns", International Journal of Systematic Bacteriology, vol. 41, No. 2, 1991, pp. 255-260.

Ben-Bassat, A., et al., "Processing of the Initiation Methionine from Proteins: Properties of the *Escherichia coli* Methionine Aminopeptidase and Its Gene Structure", Journal of Bacteriology, vol. 169, No. 2, 1987, pp. 751-757.

O'Regan, M., et al., "Cloning and nucleotide sequence of the phosphoenolpyruvate, Gene, 1989, 77:237, carboxylase-coding gene of *Corynebacterium glutamicum* ATCC13032", Gene, vol. 77, 1989, pp. 237-251.

Sahin-Toth, M., et al., "Cysteine scanning mutagenesis of the N-terminal 32 amino acid residues in the lactose permease of *Escherichia coli*", Protein Sciences, vol. 3, 1994, pp. 240-247.

Hochuli, E., et al., "Genetic Approach to Facilitate Purfication of Recombinant Proteins With a Novel Metal Chelate Adsorbent", Biotechnology, vol. 6, 1988, pp. 1321-1325.

Martin, J.F., et al., "Cloning Systems in Amino Acid-Producing Corynebacteria", Biotechnology, vol. 5, 1987, pp. 137-146.

Guerrero, C., et al., "Directed mutagenesis of a regulatory palindromic sequence upstream from the *Brevibacterium lactofermentum* tryptophan operon", Gene, vol. 138, 1994, pp. 35-41.

Tsuchiya, M., et al., "Genetic Control Systems of *Escherichia coli* Can Confer Inducible Expression of Cloned Genes in Coryneform Bacteria", Biotechnology, vol. 6, 1988, pp. 428-430.

Eikmanns, B. J., et al., "A family of *Corynebacterium glutamicum/ Escherichia coli* shuttle vectors for cloning, controlled gene expression, and promoter probing", Gene, vol. 102, 1991, pp. 93-98.

Schwarzer, A., et al., "Manipulation of *Corynebacterium glutemicum* by Gene Disruption and Replacement", Biotechnology, vol. 9, 1991, pp. 84-87.

Reinscheid, D. J., et al., "Stable Expression of *hom-1-thrB* in *Corynebacterium glutamicum* and Its Effect on the Carbon Flux to Threonine and Related Amino Acids", Applied and Environmental Microbiology, vol. 60, No. 1, 1994, pp. 126-132.

Labarre, J., et al., "Gene Replacement, Integration, and Amplification at the *gdhA* Locus of *Corynebacterium glutamicum*", Journal of Bacteriology, 1993, vol. 175, No. 4, pp. 1001-1007.

Malumbres, M., et al., "Codon preference in Corynebacteria", Gene, vol. 134, 1993, pp. 15-24.

Jensen, P. R., et al., "Artificial Promoters for Metabolic Optimization", Biotechnology and Bioengineering, vol. 58, 1998, pp. 191-195.

Makrides, S. C., "Strategies for Achieving High-Level Expression of Genes in *Escherichia coli*", Microbiological Reviews, vol. 60, No. 3, 1996, pp. 512-538.

Patek, M., et al., "Promoters from *Corynebacterium glutamicum*: cloning, molecular analysis and search for a consensus motif", Microbiology, 1996, vol. 142, pp. 1297-1309.

Sonnen, H., et al., "Characterization of pGA1, a new plasmid from *Corynebacterium glutamicum* LP-6", Gene, vol. 107, 1991, pp. 69-74.

Serwold-Davis, T. M., et al., "Localization of an origin of replication in *Corynebacterium diphtheriae* broad host range plasmid pNG2 that also function in *Escherichia coli*", FEMS Microbiology Letters, vol. 66, 1990, pp. 119-124.

Simon, R., et al., "A Broad Host Range Mobilization System for In Vivo Genetic Engineering: Transposon Mutagenesis in Gram Negative Bacteria", Biotechnology, vol. 1, 1983, pp. 784-791.

Schäfer, A., et al., "Small mobilizable multi-purpose cloning vectors derived from the *Escherichia coli* plasmids pK18 and pK19: selection of defined deletions in the chromosome of *Corynebacterium glutamicum*", Gene, vol. 145, 1994, pp. 69-73.

Bernard, P., et al., "The F Plasmid CcdB Protein Induces Efficient ATP-dependent DNA Cleavage by Gyrase", J. Mol. Biol., vol. 234, 1993, pp. 534-541.

Schrumpf, B., et al., "A Functionally Split Pathway for Lysine Synthesis in *Corynebacterium glutamicum*", Journal of Bacteriology, vol. 173, No. 14, 1991, pp. 4510-4516.

Spratt, B. G., "Kanamycin-resistant vectors that are analogues of plasmids pUC8, pUC9, Gene 1986, 41: 337 pEMBL8 and pEMBL9", Gene, vol. 41, 1986, pp. 337-342.

Thierbach, G., et al., "Transformation of spheroplasts and protoplasts of *Corynebacterium glutamicum*", Appl. Microbiol. Biotechnol., vol. 29, 1988, pp. 356-362.

Dunican, L. K., et al., "High Frequency Transformation of Whole Cells of Amino Acid Producing Coryneform Bacteria Using High Voltage Electroporation", Biotechnology, vol. 7, 1989, pp. 1067-1070.

Tauch, A., et al., "*Corynebacterium glutamicum* DNA is subjected to methylation-restriction in *Escherichia coli*", FEMS Microbiology Letters, vol. 123, 1994, pp. 343-347.

Motoyama, H., et al., "Overproduction of $_L$-Lysine from methanol by *Methylobacillus glycogenes* Derivatives Carrying a Plasmid with a Mutated *dapA* Gene", Applied and Environmental Microbiology, vol. 67, No. 7, 2001, pp. 3064-3070.

Eikmanns, B. J., "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase", Journal of Bacteriology, vol. 174, No. 19, 1992, pp. 6076-6086.

Patek, M., et al., "Leucine Synthesis in *Corynebacterium glutamicum*: Enzyme Activities, Structure of *leuA*, and Effect of *leuA* Inactivation of Lysine Synthesis", Applied and Environmental Microbiology, vol. 60, No. 1, 1994, pp. 133-140.

Malakhova, I. I., et al., "Thin-Layer Chromatography of Free Amino Acids, Selection of Conditions for the Separation of L-Lysine, L-Homoserine, and L-Threonine", Biotekhnologiya, vol. 11, 1996, pp. 27-31.

Schmidt, S., et al., "Near infrared spectroscopy in fermentation and quality control for amino acid production", Bioprocess Engineering, vol. 19, 1998, pp. 67-70.

Lennox, E.S., "Transduction of Linked Genetic Characters of the Host by Bacteriophage P1", Virology, vol. 1, 1955, pp. 190-206.

Tauch, A., et al., "The Erythromycin Resistance Gene of the *Corynebacterium xerosis* R-plasmid pTP10 Also Carrying Chloramphenicol, Kanamycin, and Tetracycline Resistances is Capable of Transposition in *Corynebacterium glutamicum*", Plasmid, vol. 33, 1995, pp. 168-179.

Liebl, W., et al., "High efficiency electroporation of intact *Corynebacterium glutamicum* cells", FEMS Microbiology Letters, vol. 65, 1989, pp. 299-303.

Kase, H., et al., "$_L$-Methionine Production by Methionine Analog-resistant Mutants of *Corynebacterium glutamicum*", Agr. Biol. Chem., vol. 39, No. 1, 1975, pp. 153-160.

Eikmanns, B. J., et al., "Nucleotide sequence, expression and transcriptional analysis of the *Corynebacterium glutemicum gltA* gene encoding citrate synthase", Microbiology, vol. 140, 1994, pp. 1817-1828.

METHOD FOR THE PRODUCTION BY FERMENTATION OF SULPHUR-CONTAINING FINE CHEMICALS (METF)

RELATED APPLICATIONS

This application is a national stage application (under 35 U.S.C 371) of PCT/EP2003/009451 filed Aug. 26, 2003, which claims benefit of German application 102 39 308.7 filed Aug. 27, 2002.

The invention relates to a method for the fermentative production of sulfur-containing fine chemicals, in particular L-methionine, by using bacteria which express a nucleotide sequence coding for a methylenetetrahydrofolate reductase (metF) gene.

PRIOR ART

Sulfur-containing fine chemicals such as, for example, methionine, homocysteine, S-adenosylmethionine, glutathione, cysteine, biotin, thiamine, lipoic acid are produced in cells via natural metabolic processes and are used in many branches of industry, including the food, animal feed, cosmetics and pharmaceutical industries. These substances which are collectively referred to "sulfur-containing fine chemicals" include organic acids, both proteinogenic and nonproteinogenic amino acids, vitamins and cofactors. They are most expediently produced on a large scale by means of cultivating bacteria which have been developed in order to produce and secrete large amounts of the substance desired in each case. Organisms which are particularly suitable for this purpose are coryneform bacteria, Gram-positive nonpathogenic bacteria.

It is known that amino acids are produced by fermentation of strains of coryneform bacteria, in particular *Corynebacterium glutamicum*. Due to the great importance, the production processes are constantly improved. Process improvements can relate to measures regarding technical aspects of the fermentation, such as, for example, stirring and oxygen supply, or to the nutrient media composition such as, for example, sugar concentration during fermentation or to the work-up to give the product, for example by ion exchange chromatography, or to the intrinsic performance properties of the microorganism itself.

A number of mutant strains which produce an assortment of desirable compounds from the group of sulfur-containing fine chemicals have been developed via strain selection. The performance properties of said microorganisms are improved with respect to the production of a particular molecule by applying methods of mutagenesis, selection and mutant selection. However, this is a time-consuming and difficult process. In this way strains are obtained, for example, which are resistant to antimetabolites such as, for example, the methionine analogs α-methylmethionine, ethionine, norleucine, n-acetylnorleucine, S-trifluoromethylhomocysteine, 2-amino-5-heprenoitic acid, selenomethionine, methioninesulfoximine, methoxine, 1-aminocyclopentanecarboxylic acid or which are auxotrophic for metabolites important for regulation and which produce sulfur-containing fine chemicals such as, for example, L-methionine.

Methods of recombinant DNA technology have also been used for some years to improve *Corynebacterium* strains producing L-amino acids by amplifying individual amino-acid biosynthesis genes and investigating the effect on amino acid production.

BRIEF DESCRIPTION OF THE INVENTION

It is an object of the present invention to provide a novel method for the improved fermentative production of sulfur-containing fine chemicals, in particular L-methionine.

We have found that this object is achieved by providing a method for the fermentative production of a sulfur-containing fine chemical, comprising the expression of a heterologous nucleotide sequence coding for a protein with metF activity in a coryneform bacterium.

The invention firstly relates to a method for the fermentative production of at least one sulfur-containing fine chemical, which comprises the following steps:
a) fermentation of a coryneform bacteria culture producing the desired sulfur-containing fine chemical, the coryneform bacteria expressing at least one heterologous nucleotide sequence which codes for a protein with methylenetetrahydrofolate reductase (metF) activity;
b) concentration of the sulfur-containing fine chemical in the medium or in the bacterial cells, and
c) isolation of the sulfur-containing fine chemical, which preferably comprises L-methionine.

The above heterologous metF-encoding nucleotide sequence is preferably less than 100%, such as, for example, more than 70%, such as 75, 80, 85, 90 or 95%, or less than 90%, such as, for example, up to 60, 50, 40, 30, 20 or 10% homologous to the metF-encoding sequence from *Corynebacterium glutamicum* ATCC 13032. The metF-encoding sequence is derived preferably from any of the following organisms of list I:

| List I | |
|---|---|
| Organism | Strain collection |
| *Corynebacterium diphteriae* | ATCC 14779 |
| *Streptomyces lividans* | ATCC 19844 |
| *Streptomyces coelicolor* | ATCC 10147 |
| *Aquifex aeolicus* | DSM 6858 |
| *Burkholderia cepacia* | ATCC 25416 |
| *Nitrosomonas europaea* | ATCC 19718 |
| *Pseudomonas aeruginosa* | ATCC 17933 |
| *Xylella fastidiosa* | ATCC 35881 |
| *Pseodomonas fluorescens* | ATCC 13525 |
| *Schizosaccharomyces pombe* | ATCC 24969 |
| *Saccharomyces cerevisiae* | ATCC 10751 |
| *Erwinia carotovora* | ATCC 15713 |
| *Klebsiella pneumoniae* | ATCC 700721 |
| *Salmonella typhi* | ATCC 12839 |
| *Salmonella typhimurium* | ATCC 15277 |
| *Escherichia coli* K12 | ATCC 55151 |
| *Vibrio cholerae* | ATCC 39315 |
| *Haemophilus influenzae* | ATCC 51907 |
| *Caulobacter crescentus* | ATCC 19089 |
| *Actinobacillus actinomycetemcomitans* | ATCC 33384 |
| *Neisseria meningitis* | ATCC 6253 |
| *Rhodobacter capsulatus* | ATCC 11166 |
| *Campylobacter jejuni* | ATCC 33560 |
| *Lactococcus lactis* | ATCC 7962 |
| *Prochlorococcus marinus* | PCC 7118 |
| *Bacillus stearothermophilus* | ATCC 12980 |

ATCC: American Type Culture Collection, Rockville, Md., USA
PCC: Pasteur Culture Collection of Cyanobacteria. Paris France
DSM: German collection of Microorganisms and Cell Cultures The metF-encoding sequence used according to the invention preferably comprises a coding sequence according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 or a nucleotide sequence homologous thereto which codes for a protein with metF activity.

Moreover, the metF-encoding sequence used according to the invention preferably codes for a protein with metF activity, said protein comprising an amino acid sequence according to SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 or an amino acid sequence homologous thereto which represents a protein with metF activity.

The coding metF sequence is preferably a DNA or an RNA which can be replicated in coryneform bacteria or is stably integrated into the chromosome.

According to a preferred embodiment, the method of the invention is carried out by
a) using a bacterial strain transformed with a plasmid vector which carries at least one copy of the coding metF sequence under the control of regulatory sequences or
b) using a strain in which the coding metF sequence has been integrated into the bacterial chromosome.

Furthermore, preference is given to overexpressing the coding metF sequence for the fermentation.

It may also be desirable to ferment bacteria in which additionally at least one further gene of the biosynthetic pathway of the desired sulfur-containing fine chemical has been amplified; and/or in which at least one metabolic pathway, which reduces production of the desired sulfur-containing fine chemical has, at least partially, been switched off.

It may also be desirable to ferment bacteria in which additionally the activity of at least one further gene of the biosynthetic pathway of the desired sulfur-containing fine chemical is not undesirably influenced by metabolic metabolites.

Therefore, according to another embodiment of the method of the invention, coryneform bacteria are fermented in which, at the same time, at least one of the genes selected from among
  a) the lysC gene, which encodes an aspartate kinase,
  b) the gene asd, which encodes an aspartate-semialdehyde dehydrogenase,
  c) the glyceraldehyde-3-phosphate dehydrogenase-encoding gene gap,
  d) the 3-phosphoglycerate kinase-encoding gene pgk,
  e) the pyruvate carboxylase-encoding gene pyc,
  f) the triose phosphate isomerase-encoding gene tpi,
  g) the homoserine O-acetyltransferase-encoding gene metA,
  h) the cystathionine gamma-synthase-encoding gene metB,
  i) the cystathionine gamma-lyase-encoding gene metC,
  j) the serine hydroxymethyltransferase-encoding gene glyA,
  k) the O-acrylhomoserine sulfhydrylase-encoding gene metY,
  l) the methionine synthase-encoding gene metH,
  m) the phosphoserine aminotransferase-encoding gene serC,
  n) the phosphoserine phosphatase-encoding gene serB,
  o) the serine acetyl transferase-encoding gene cysE,
  p) the homoserine dehydrogenase-encoding gene hom is overexpressed.

According to another embodiment of the method of the invention, coryneform bacteria are fermented in which, at the same time, at least one of the genes selected from among genes of the abovementioned group a) to p) is mutated in such a way that the activity of the corresponding proteins is influenced by metabolic metabolites to a smaller extent, if at all, compared to nonmutated proteins and that in particular the inventive production of the fine chemical is not adversely affected.

According to another embodiment of the method of the invention, coryneform bacteria are fermented in which, at the same time, at least one of the genes selected from among
  q) the homoserine kinase-encoding gene thrB,
  r) the threonine dehydratase-encoding gene ilvA,
  s) the threonine synthase-encoding gene thrC,
  t) the meso-diaminopimelate D-dehydrogenase-encoding gene ddh,
  u) the phosphoenolpyruvate carboxykinase-encoding gene pck,
  v) the glucose-6-phosphate 6-isomerase-encoding gene pgi,
  w) the pyruvate oxidase-encoding gene poxB,
  x) the dihydrodipicolinate synthase-encoding gene dapA,
  y) the dihydrodipicolinate reductase-encoding gene dapB; or
  z) the diaminopicolinate decarboxylase-encoding gene lysA is attenuated, in particular by reducing the rate of expression of the corresponding gene.

According to another embodiment of the method of the invention, coryneform bacteria are fermented in which, at the same time, at least one of the genes of the above groups q) to z) is mutated in such a way that the enzymic activity of the corresponding protein is partially or completely reduced.

Preference is given to using, in the method of the invention, microorganisms of the species *Corynebacterium glutamicum*.

The invention further relates to a method for producing an L-methionine-containing animal feed additive from fermentation broths, which comprises the following steps:
  a) culturing and fermentation of an L-methionine-producing microorganism in a fermentation medium;
  b) removal of water from the L-methionine-containing fermentation broth;
  c) removal of from 0 to 100% by weight of the biomass formed during fermentation; and
  d) drying of the fermentation broth obtained according to b) and/or c), in order to obtain the animal feed additive in the desired powder or granule form.

The invention likewise relates to the coding metF sequences isolated from the above microorganisms for the first time, to the metF enzymes encoded thereby and to the functional homologs of these polynucleotides and proteins, respectively.

Figure 1:
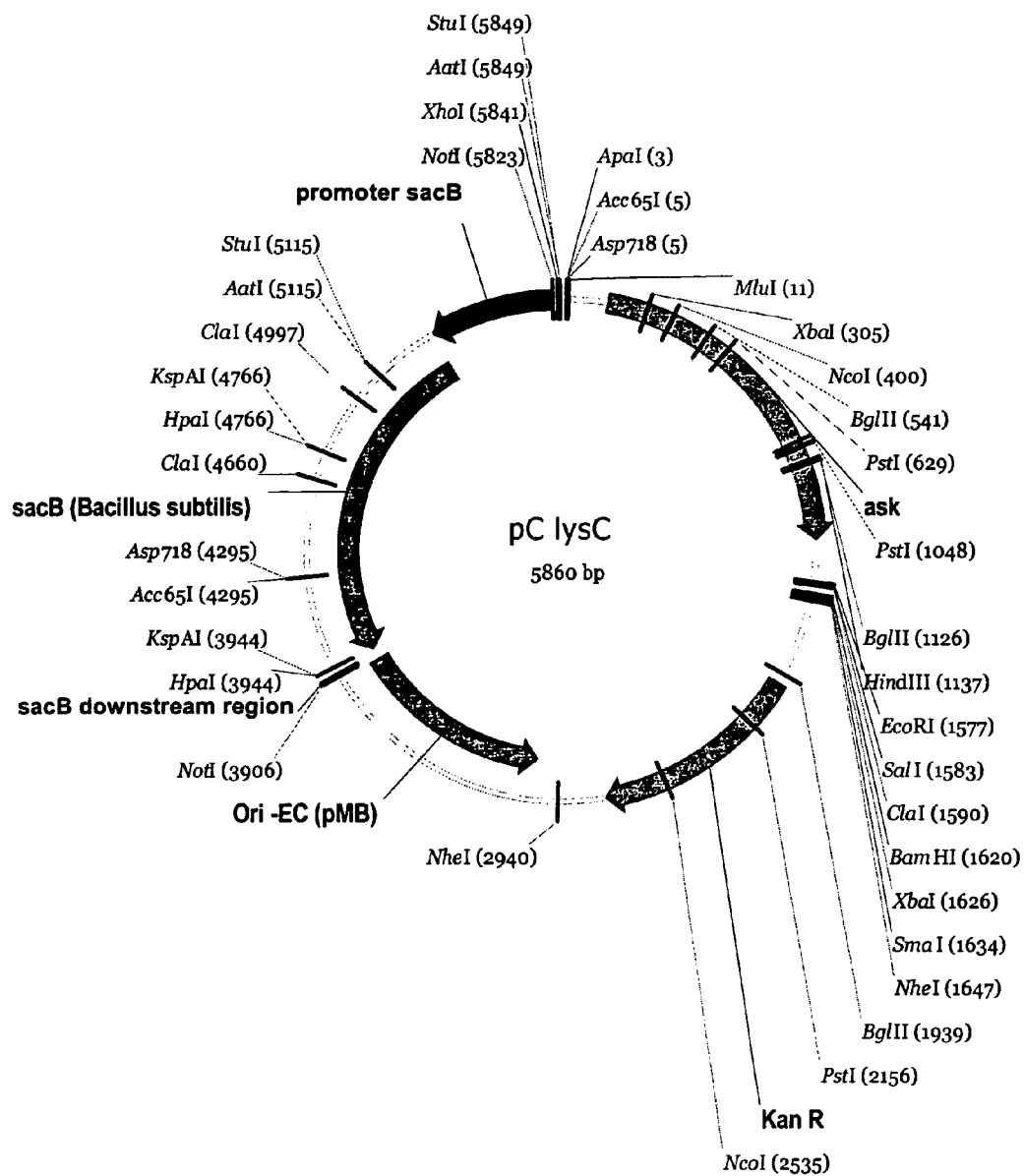
FIG. 1 shows the plasmid map of plasmid pCIS lysC.

DETAILED DESCRIPTION OF THE INVENTION a) General Terms

Proteins with methylenetetrahydrofolate reductase activity are described as being proteins which are capable of reducing 5,10-methylenetetrahydrofolare ($CH_2$—H(4)folate) to 5-methyltetrehydrofolate ($CH_3$—H(4)folate) with oxidation of the cofactor NADH or NADPH. The skilled worker is familiar with further details of the metF protein: (Matthews R G. Sheppard C. Goulding C. European Journal of Pediatrics. 157 Suppl 2: S54-9,1998, Trimmer E E. Ballou D P. Matthewsn R G. Biochemistry. 40(21):6205-15, 2001). The skilled worker can detect the enzymatic activity of metF by means of enzyme assays, protocols for which may be: Matthews, R. G., Methylenetetrahydrofolate reductase from pig liver. Methods in Enzymology. 122:372-81, 1986.

Within the scope of the present invention, the term "sulfur-containing fine chemical" includes any chemical compound which contains at least one covalently bound sulfur atom and is accessible by a fermentation method of the invention. Nonlimiting examples thereof are methionine, homocysteine, S-adenosylmethionine, in particular methionine and S-adenosylmethionine.

Within the scope of the present invention, the terms "L-methionine", "methionine", homocysteine and S-adenosylmethionine also include the corresponding salts such as, for example, methionine hydrochloride or methionine sulfate.

"Polynucleotides" in general refers to polyribonucleotides (RNA) and polydeoxyribonucleotides (DNA) which may be unmodified RNA and DNA respectively, or modified RNA and DNA, respectively.

According to the invention, "polypeptides" means peptides or proteins which contain two or more amino acids linked via peptide bonds.

The term "metabolic metabolite" refers to chemical compounds which occur in the metabolism of organisms as intermediates or else final products and which, apart from their property as chemical building blocks, may also have a modulating effect on enzymes and on their catalytic activity. It is known from the literature that such metabolic metabolites may act on the activity of enzymes in both an inhibiting and a stimulating manner (Biochemistry, Stryer, Lubert, 1995 W. H. Freeman & Company, New York, N.Y.). The possibility of producing in organisms enzymes in which the influence of metabolic metabolites has been modified by measures such as mutation of the genomic DNA by UV radiation, ionizing radiation or mutagenic substances and subsequent selection for particular phenotypes has also been described in the literature (Sahm H., Eggeling L., de Graaf A A., Biological Chemistry 381(9-10):899-910,2000; Eikmanns B J., Eggeling L., Sahm H., Antonie van Leeuwenhoek., 64:145-63, 1993-94). These altered properties may also be achieved by specific measurements. The skilled worker knows that it is possible specifically to modify in enzyme genes particular nucleotides of the DNA coding for the protein in such a way that the protein resulting from the expressed DNA sequence has certain new properties, for example that the modulating effect of metabolic metabolites on the unmodified protein has changed.

The activity of enzymes may be influenced in such a way that the reaction rate is reduced or the affinity for the substrate is modified or the reaction rates are changed.

The terms "express" and "amplification" or "overexpression" describe in the context of the invention the production of or increase in intracellular activity of one or more enzymes encoded by the corresponding DNA in a microorganism. For this purpose, for example, it is possible to introduce a gene into an organism, to replace an existing gene by another gene, to increase the copy number of the gene or genes, to use a strong promoter or to use a gene which codes for a corresponding enzyme having a high activity, and these measures can be combined, where appropriate.

b) metF Proteins of the Invention

The invention likewise includes "functional equivalents" of the specifically disclosed metF enzymes of organisms in the above list I.

Within the scope of the present invention, "functional equivalents" or analogs of the specifically disclosed polypeptides are polypeptides different therefrom, which furthermore have the desired biological activity such as, for example, substrate specificity.

According to the invention, "functional equivalents" means in particular mutants which have in at least one of the abovementioned sequence positions an amino acid other than the specifically mentioned amino acid, but which have nevertheless one of the abovementioned biological activities. "Functional equivalents" thus also include the mutants obtainable by one or more amino acid additions, substitutions, deletions and/or inversions, it being possible for said modifications to occur at any position in the sequence as long as they result in a mutant having the property profile of the invention. There is functional equivalence in particular also when the reaction patterns of mutant and unmodified polypeptide match qualitatively, i.e. identical substrates are converted with different rates, for example.

"Functional equivalents" naturally also comprise polypeptides which are obtainable from other organisms, and naturally occurring variants. For example, homologous sequence regions can be found by sequence comparison, and equivalent enzymes can be established following the specific guidelines of the invention.

"Functional equivalents" likewise comprise fragments, preferably individual domains or sequence motifs, of the polypeptides of the invention, which have the desired biological function, for example.

"Functional equivalents" are also fusion proteins which have one of the abovementioned polypeptide sequences or functional equivalents derived therefrom and at least one further heterologous sequence functionally different therefrom in functional N- or C-terminal linkage (i.e. with negligible functional impairment of the functions of the fusion protein parts). Nonlimiting examples of such heterologous sequences are, for example, signal peptides, enzymes, immunoglobulins, surface antigens, receptors or receptor ligands.

According to the invention, "functional equivalents" include homologs of the specifically disclosed proteins. These have at least 30%, or about 40%, 50%, preferably at least about 60%, 65%, 70%, or 75%, in particular at least 85%, such as, for example, 90%, 95% or 99%, homology to one of the specifically disclosed sequences, calculated by the algorithm of Pearson and Lipman, Proc. Natl. Acad., Sci. (USA) 85(8), 1988, 2444-2448.

Homologs of the proteins or polypeptides of the invention can be generated by mutagenesis, for example by point mutation or truncation of the protein. The term "homolog", as used herein, relates to a variant form of the protein, which acts as agonist or antagonist of the protein activity.

Homologs of the proteins of the invention can be identified by screening combinatorial libraries of mutants such as, for example, truncation mutants. It is possible, for example, to generate a variegated library of protein variants by combinatory mutagenesis at the nucleic acid level, for example by enzymatic ligation of a mixture of synthetic oligonucleotides. There is a multiplicity of methods which can be used for preparing libraries of potential homologs from a degenerate oligonucleotide sequence. Chemical synthesis of a degenerate gene sequence can be carried out in an automatic DNA synthesizer, and the synthetic gene can then be ligated into a suitable expression vector. The use of a degenerate set of genes makes it possible to provide whole sequences which encode the desired set of potential protein sequences in one mixture. Methods for synthesizing degenerate oligonucleotides are known to the skilled worker (for example, Narang, S. A., (1983) Tetrahedron 39:3; Itakura et al., (1984) Annu. Rev. Biochem. 53:323; Itakura et al., (1984) Science 198:1056; Ike et al., (1983) Nucleic Acids Res. 11:477).

In addition, libraries of fragments of the protein codon can be used to generate a variegated population of protein fragments for screening and for subsequent selection of homologs of a protein of the invention. In one embodiment, a library of coding sequence fragments can be generated by treating a double-stranded PCR fragment of a coding sequence with a nuclease under conditions under which nicking occurs only about once per molecule, denaturing the double-stranded DNA, renaturing the DNA to form double-stranded DNA which may comprise sense/antisense pairs of various nicked products, removing single-stranded sections from newly formed duplexes by treatment with S1 nuclease and ligating the resulting fragment library into an expression vector. It is possible by this method to devise an expression library which encodes N-terminal, C-terminal and internal fragments of the protein of the invention, which has different sizes.

Several techniques are known in the prior art for screening gene products from combinatorial libraries which have been produced by point mutations or truncation and for screening cDNA libraries for gene products with a selected property. These techniques can be adapted to rapid screening of gene libraries which have been generated by combinatorial mutagenesis of homologs of the invention. The most frequently used techniques for screening large gene libraries undergoing high-throughput analysis comprise the cloning of the gene library into replicable expression vectors, transformation of suitable cells with the resulting vector library and expression of the combinatorial genes under conditions under which detection of the desired activity facilitates isolation of the vector encoding the gene whose product has been detected. Recursive ensemble mutagenesis (REM), a technique which increases the frequency of functional mutants in the libraries, can be used in combination with the screening tests in order to identify homologs (Arkin und Yourvan (1992) PNAS 89:7811-7815; Delgrave et al. (1993) Protein Engineering 6(3):327-331 c) Polynucleotides of the Invention

The invention also relates to nucleic acid sequences (single- and double-stranded DNA and RNA sequences such as, for example cDNA and mRNA) coding for one of the above metF enzymes and the functional equivalents thereof which are obtainable, for example, also by use of artificial nucleotide analogs.

The invention relates both to isolated nucleic acid molecules which code for polypeptides or proteins of the invention or for biologically active sections thereof, and to nucleic acid fragments which can be used, for example, for use as hybridization probes or primers for identifying or amplifying coding nucleic acids of the invention.

Moreover, the nucleic acid molecules of the invention may contain untranslated sequences from the 3' and/or 5' ends of the coding region of the gene.

An "isolated" nucleic acid molecule is separated from other nucleic acid molecules which are present in the natural source of the nucleic acid and may moreover be essentially free of other cellular material or culture medium if it is prepared by recombinant techniques, or free of chemical precursors or other chemicals if it is chemically synthesized.

The invention furthermore comprises the nucleic acid molecules complementary to the specifically described nucleotide sequences or a section thereof.

The nucleotide sequences of the invention make it possible to generate probes and primers which can be used for identifying and/or cloning homologous sequences in other cell types and organisms. Such probes and primers usually complete a nucleotide sequence region which hybridizes under stringent conditions to at least about 12, preferably at least about 25, such as, for example 40, 50 or 75, consecutive nucleotides of a sense strand of a nucleic acid sequence of the invention or of a corresponding antisense strand.

Further nucleic acid sequences of the invention are derived from SEQ ID NO:1, 3, 5, 7, 9, 11, 13, 15, 17, 19, 21, 23, 25, 27, 29, 31, 33, 35, 37, 39, 41, 43, 45, 47, 49, 51 or 53 and differ therefrom through addition, substitution, insertion or deletion of one or more nucleotides, but still code for polypeptides having the desired profile of properties. These may be polynucleotides which are identical to above sequences in at least about 50%, 55%, 60%, 65%, 70%, 80% or 90%, preferably in at least about 95%, 96%, 97%, 98% or 99%, of the sequence positions.

The invention also includes those nucleic acid sequences which comprise "silent" mutations or are modified, by comparison with a specifically mentioned sequence, in accordance with the codon usage of a specific source or host organism, as well as naturally occurring variants such as, for example, splice variants or allelic variants. The invention likewise relates to sequences which are obtainable by conservative nucleotide substitutions (i.e. the relevant amino acid is replaced by an amino acid of the same charge, size, polarity and/or solubility).

The invention also relates to molecules derived from specifically disclosed nucleic acids through sequence polymorphisms. These genetic polymorphisms may exist because of the natural variation between individuals within a population. These natural variations usually result in a variance of from 1 to 5% in the nucleotide sequence of a gene.

The invention furthermore also comprises nucleic acid sequences which hybridize with or are complementary to the abovementioned coding sequences. These polynucleotides can be found on screening of genomic or cDNA libraries, and where appropriate, be amplified therefrom by means of PCR using suitable primers, and then, for example, be isolated with suitable probes. Another possibility is to transform suitable microorganisms with polynucleotides or vectors of the invention, multiply the microorganisms and thus the polynucleotides, and then isolate them. An additional possibility is to synthesize polynucleotides of the invention by chemical routes.

The property of being able to "hybridize" to polynucleotides means the ability of a polynucleotide or oligonucleotide to bind under stringent conditions to an almost complementary sequence, while there are no unspecific bindings between noncomplementary partners under these conditions. For this purpose, the sequences should be 70-100%, preferably 90-100%, complementary. The property of complementary sequences being able to bind specifically to one another is made use of, for example, in the Northern or Southern blot technique or in PCR or RT-PCR in the case of primer binding. Oligonucleotides with a length of 30 base pairs or more are usually employed for this purpose. Stringent conditions means, for example, in the Northern blot technique the use of a washing solution at 50-70° C., preferably 60-65° C., for example 0.1×SSC buffer with 0.1% SDS (20×SSC; 3M NaCl, 0.3M Na citrate, pH 7.0) for eluting nonspecifically hybridized cDNA probes or oligonucleotides. In this case, as mentioned above, only nucleic acids with a high degree of complementarity remain bound to one another. The setting up of stringent conditions is known to the skilled worker and is described, for example, in Ausubel et al., Current Protocols in Molecular Biology, John Wiley & Sons, N.Y. (1989), 6.3.1-6.3.6. beschrieben.

c) Isolation of the Coding metF Gene

The metF genes coding for the enzyme methylenetetrahydrofolate reductase can be isolated from the organisms of the above list I in a manner known per se.

In order to isolate the metF genes or else other genes of the organisms of the above list I, first a gene library of this organism is generated in *Escherichia coli* (*E. coli*). The generation of gene libraries is described in detail in generally known textbooks and manuals. Examples which may be mentioned are the textbook by Winnacker: Gene und Klone, Eine Einführung in die Gentechnologie (Verlag Chemie, Weinheim, Germany, 1990), and the manual by Sambrook et al.: Molecular Cloning, A Laboratory Manual (Cold Spring Harbor Laboratory Press, 1989). A very well-known gene library is that of *E. coli* K-12 strain W3110, which was generated in λ vectors by Kohara et al. (Cell50, 495-508 (198)).

In order to produce a gene library from organisms of list I in *E. coli*, cosmids such as the cosmid vector SuperCos I (Wahl et al., 1987, Proceedings of the National Academy of Sciences USA, 84: 2160-2164), or else plasmids such as pBR322 (BoliVal; Life Sciences, 25,807-818 (1979)) or pUC9 (Vieira et al., 1982, Gene, 19: 259-268) can be used. Suitable hosts are in particular those *E. coli* strains which are restriction and recombination defective. An example of this is the strain DH5αmcr which has been described by Grant et al. (Proceedings of the National Academy of Sciences USA, 87 (1990) 4645-4649). The long DNA fragments cloned with the aid of cosmids may then in turn be subcloned into common vectors suitable for sequencing and subsequently be sequenced, as described, for example, in Sanger et al. (proceedings of the National Academy of Sciences of the United States of America, 74: 5463-5467, 1977).

The DNA sequences obtained can then be studied using known algorithms or sequence analysis programs such as, for example, those by Staden (Nucleic Acids Research 14, 217-232(1986)), by Marck (Nucleic Acids Research 16, 1829-1836 (1988)) or the GCG program by Butler (Methods of Biochemical Analysis 39, 74-97 (1998)).

The metF-encoding DNA sequences from organisms according to the above list I were found. In particular, DNA sequences according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 were found. Furthermore, the amino acid sequences of the corresponding proteins were derived from said DNA sequences present, using the above-described methods. SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 depict the resulting amino acid sequences of the metF gene products.

Coding DNA sequences which result from the sequences according to SEQ ID NO:1, 3, 5, 7, 9, 11, 13, 15, 17, 19, 21, 23, 25, 27, 29, 31, 33, 35, 37, 39, 41, 43, 45, 47, 49, 51 and 53 due to the degeneracy of the genetic code are likewise subject of the invention. In the same way, the invention relates to DNA sequences which hybridize with said sequences or parts of sequences derived therefrom.

Instructions for identifying DNA sequences by means of hybridization can be found by the skilled worker, inter alia, in the manual "The DIG System Users Guide fur Filter Hybridization" from Boehringer Mannheim GmbH (Mannheim, Germany, 1993) and in Liebl et al. (International Journal of Systematic Bacteriology (1991) 41: 255-260). Instructions for amplifying DNA sequences with the aid of the polymerase chain reaction (PCR) can be found by the skilled worker, inter alia, in the manual by Gait: Oligonucleotide synthesis: A Practical Approach (IRL Press, Oxford, UK, 1984) and in Newton and Graham: PCR (Spektrum Akademischer Verlag, Heidelberg, Germany, 1994).

It is furthermore known that changes at the N- and/or C-terminus of a protein do not substantially impair its function or may even stabilize said function. Information on this can be found by the skilled worker, inter alia, in Ben-Bassat et al. (Journal of Bacteriology 169: 751-757 (1987)), in O'Regan et al. (Gene 77: 237-251 (1989), in Sahin-Toth et al. (Protein Sciences 3: 240-247 (1994)), in Hochuli et al. (Biotechnology 6: 1321-1325 (1988)) and in known textbooks of genetics and molecular biology.

Amino acid sequences which result accordingly from SEQ ID NO:2, 4, 6, 8, 10, 12, 14, 16, 18, 20, 22, 24, 26, 28, 30, 32, 34, 36, 38, 40, 42, 44, 46, 48, 50, 52 and 54 are likewise part of the invention.

d) Host Cells used According to the Invention

The invention further relates to microorganisms serving as host cells, in particular coryneform bacteria, which contain a vector, in particular a shuttle vector or plasmid vector, carrying at least one metF gene as defined by the invention or in which a metF gene of the invention is expressed or amplified.

These microorganisms can produce sulfur-containing fine chemicals, in particular L-methionine, from glucose, sucrose, lactose, fructose, maltose, molasses, starch, cellulose or from glycerol and ethanol. Said microorganisms are preferably coryneform bacteria, in particular of the genus *Corynebacterium*. Of the genus *Corynebacterium*, mention must be made in particular of the species *Corynebacterium glutamicum* which is known in the art for its ability to produce L-amino acids.

Examples of suitable strains of coryneform bacteria, which may be mentioned, are those of the genus *Corynebacterium*, in particular of the species *Corynebacterium glutamicum* (*C. glutamicum*), such as

*Corynebacterium glutamicum* ATCC 13032,
*Corynebacterium acetoglutamicum* ATCC 15806,
*Corynebacterium acetoacidophilum* ATCC 13870,
*Corynebacterium thermoaminogenes* FERM BP-1539,
*Corynebacterium melassecola* ATCC 17965
or
of the genus *Brevibacterium*, such as
*Brevibacterium flavum* ATCC 14067
*Brevibacterium lactofermentum* ATCC 13869 and

*Brevibacterium divaricatum* ATCC 14020;
Or strains derived therefrom such as
*Corynebacterium glutamicum* KFCC10065
*Corynebacterium glutamicum* ATCC21608
which likewise produce the desired fine chemical or the precursor(s) thereof.

The abbreviation KFCC means the Korean Federation of Culture Collection, the abbreviation ATCC means the American Type Strain Culture Collection, the abbreviation FERM BP means the Collection of the National Institute of Bioscience and Human Technology, Agency of Industrial Science and Technology, Japan.

e) Carrying out the Fermentation of the Invention

According to the invention, it was found that coryneform bacteria, after overexpression of a metF gene from organisms of the list I, produce sulfur-containing fine chemicals, in particular L-methionine, in an advantageous manner.

To achieve overexpression, the skilled worker can take different measures individually or in combination. Thus it is possible to increase the copy number of the appropriate genes or to mutate the promoter and regulatory region or the ribosomal binding site which is located upstream of the structural gene. Expression cassettes which are incorporated upstream of the structural gene act in the same way. Inducible promoters make it additionally possible to increase expression during the course of the fermentative L-methionine production. Expression is likewise improved by measures which extend the life span of the mRNA. Furthermore, the enzymic activity is likewise enhanced by preventing degradation of the enzyme protein. The genes or gene constructs may be either present in plasmids with varying copy number or integrated and amplified in the chromosome. A further possible alternative is to achieve overexpression of the relevant genes by changing the media composition and management of the culture. Instructions for this can be found by the skilled worker, inter alia, in Martin et al. (Biontechnology 5, 137-146 (1987)), in Guerrero et al. (Gene 138, 35-41 (1994)), Tsuchiya and Morinaga (Bio/Technology 6, 428-430 (1988)), in Eikmanns et al. (Gene 102, 93-98 (1991)), in the European patent 0472869, in U.S. Pat. No. 4,601,893, in Schwarzer and Pühler (Biotechnology 9, 84-87 (1991)), in Remscheid et al. (Applied and Environmental Microbiology 60, 126-132 (1994)), in LaBarre et al. (Journal of Bacteriology 175, 1001-1007 (1993)), in the patent application WO 96/15246, in Malumbres et al. (Gene 134, 15-24 (1993)), in the Japanese published specification JP-A-10-229891, in Jensen und Hammer (Biotechnology and Bioengineering 58, 191-195 (1998)), in Makrides (Microbiological Reviews 60: 512-538 (1996) and in known textbooks of genetics and molecular biology.

The invention therefore also relates to expression constructs comprising a nucleic acid sequence coding for a polypeptide of the invention under the genetic control of regulatory nucleic acid sequences; and to vectors comprising at least one of said expression constructs. Such constructs of the invention preferably include a promoter 5' upstream of the particular coding sequence and a terminator sequence 3' downstream and also, where appropriate, further regulatory elements, in each case operatively linked to the coding sequence. An "operative linkage" means the sequential arrangement of promoter, coding sequence, terminator and, where appropriate, further regulatory elements such that each of the regulatory elements can properly carry out its function in the expression of the coding sequence. Examples of operatively linkable sequences are activating sequences and enhancers and the like. Further regulatory elements include selectable markers, amplification signals, origins of replication and the like. Suitable regulatory sequences are described, for example in Goeddel, Gene Expression Technology: Methods in Enzymology 185, Academic Press, San Diego, Calif. (1990).

In addition to the artificial regulatory sequences, the natural regulatory sequence may still be present upstream of the actual structural gene. Genetic modification can, where appropriate, switch off this natural regulation and increase or decrease expression of the genes. However, the gene construct may also have a simpler design, i.e. no additional regulatory signals are inserted upstream of the structural gene and the natural promoter with its regulation is not removed. Instead, the natural regulatory sequence is mutated such that regulation no longer takes place and gene expression is increased or reduced. The gene construct may contain one or more copies of the nucleic acid sequences.

Examples of useful promoters are: ddh, amy, lysC, dapA, lysA from *Corynebacterium glutamicum* promoters, but also Gram-positive promoters SPO2, as are described in *Bacillus Subtilis* and Its Closest Relatives, Sonenshein, Abraham L., Hoch, James A., Losick, Richard; ASM Press, District of Columbia, Wash. and Patek M. Eikmanns B J., Patek J., Sahm H., Microbiology. 142 1297-309, 1996 or else the cos, tac, trp, tet, trp-tet, lpp, lac, lpp-lac, laclq, T7, T5, T3, gal, trc, ara, SP6, λ-PR and λ-PL promoters which are advantageously applied in Gram-negative bacteria. Preference is also give to using inducible promoters such as, for example light- and, in particular, temperature-inducible promoters such as the $P_rP_l$ promoter. It is in principle possible to use all natural promoters with their regulatory sequences. In addition, it is also possible to use advantageously synthetic promoters.

The regulatory sequences mentioned are intended to make specific expression of the nucleic acid sequences possible. Depending on the host organism, this may mean, for example, that the gene is expressed or overexpressed only after induction, or that it is immediately expressed and/or overexpressed.

In this connection, the regulatory sequences and factors may preferably have a beneficial effect on, and thus increase or decrease, expression. Thus, it is possible and advantageous to enhance the regulatory elements at the transcriptional level by using strong transcription signals such as promoters and/or enhancers. However, it is also possible besides this to enhance translation by, for example, improving the stability of the mRNA.

An expression cassette is prepared by fusing a suitable promoter, a suitable Shine-Dalgarno sequence, to a metF nucleotide sequence and a suitable termination signal. For this purpose, common recombination and cloning techniques are used, such as those described, for example, in Current Protocols in Molecular Biology, 1993, John Wiley & Sons, Incorporated, New York, N.Y., PCR Methods, Gelfand, David H., Innis, Michael A., Sninsky, John J., 1999, Academic Press, Incorporated, Calif., San Diego, PCR Cloning Protocols, Methods in Molecular Biology Ser., Vol. 192, 2nd ed., Humana Press, New Jersey, Totowa. T. Maniatis, E. F. Fritsch and J. Sambrook, Molecular Cloning: A Laboratory Manual, Cold Spring Harbor Laboratory, Cold Spring Harbor, N.Y. (1989) and in T. J. Silhavy, M. L. Berman und L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

The recombinant nucleic acid construct or gene construct is expressed in a suitable host organism by inserting it advantageously into a host-specific vector which makes optimal expression of the genes in the host possible. Vectors are well known to the skilled worker and can be found, for example, in "Cloning Vectors" (Pouwels P. H. et al., Hrsg, Elsevier, Amsterdam-New York-Oxford, 1985). The term "vectors" means, apart from plasmids, also all other vectors known to the skilled worker, such as, for example, phages, transposons, IS elements, plasmids, cosmids and linear or circular DNA. These vectors can replicate autonomously in the host organism or are replicated chromosomally.

MetF genes of the invention were amplified by overexpressing them by way of example with the aid of episomal plasmids. Suitable plasmids are those which are replicated in coryneform bacteria. Numerous known plasmid vectors such as, for example, pZ1 (Menkel et al., Applied and Environmental Microbiology (1989) 64: 549-554), pEKEx1 (Eikmanns et al., Gene 102: 93-98 (1991)) or pHS2-1 (Sonnen et al., Gene 107:69-74 (1991)) are based on the cryptic plasmids pHM1519, pBL1 or pGA1. Other plasmid vectors such as, for example, pCLiK5MCS, or those based on pCG4 (U.S. Pat. No. 4,489,160) or pNG2 (Serwold-Davis et al., FEMS Microbiology Letters 66, 119-124 (1990)) or pAG1 (U.S. Pat. No. 5,158,891) may be used in the same way.

Suitable plasmid vectors are furthermore also those with the aid of which it is possible to apply the method of gene amplification by integration into the chromosome, as has been described, for example, by Remscheid et al. (Applied and Environmental Microbiology 60, 126-132 (1994)) for the duplication and amplification of the hom-thrB operon. In this method, the complete gene is cloned into a plasmid vector which can replicate in a host (typically *E. coli*) but not in *C. glutamicum*. Suitable vectors are, for example, pSUP301 (Simon et al., Bio/Technology 1, 784-791 (1983)), pK18mob or pK19mob (Schäfer et al., Gene 145, 69-73 (1994)), Bernard et al., Journal of Molecular Biology, 234: 534-541 (1993)), pEM1 (Schrumpf et al., 1991, Journal of Bacteriology 173: 4510-4516) or pBGS8 (Spratt et al.,1986, Gene 41: 337-342). The plasmid vector containing the gene to be amplified is then transferred into the desired *C. glutamicum* strain via transformation. Methods for transformation are described, for example, in Thierbach et al. (Applied Microbiology and Biotechnology 29, 356-362 (1988)), Dunican and Shivnan (Biotechnology 7, 1067-1070 (1989)) and Tauch et al. (FEMS Microbiological Letters 123, 343-347 (1994)).

The activity of enzymes can be influenced by mutations in the corresponding genes in such a way that the rate of the enzymic reaction is partly or completely reduced. Examples of such mutations are known to the skilled worker (Motoyama H., Yano H., Terasaki Y., Anazawa H., Applied & Environmental Microbiology. 67:3064-70,2001, Eikmanns B J., Eggeling L., Sahm H., Antonie van Leeuwenhoek. 64:145-63, 1993-94. )

Additionally, it may be advantageous for the production of sulfur-containing fine chemicals, in particular L-methionine, to amplify, in addition to expression and amplification of a metF gene of the invention, one or more enzymes of the respective biosynthetic pathway, the cysteine pathway, of aspartate-semialdehyde synthesis, of glycolysis, of anaplerosis, of the pentose phosphate metabolism, the citrate acid cycle or the amino acid export.

Thus, one or more of the following genes can be amplified to produce sulfur-containing fine chemicals, in particular L-methionine:

the aspartate kinase-encoding gene lysC (EP 1 108 790 A2; DNA-SEQ NO. 281), the aspartate-semialdehyde dehydrogenase-encoding gene asd (EP 1 108 790 A2; DNA-SEQ NO. 282), the glyceraldehyde-3-phosphate dehydrogenase-encoding gene gap (Eikmanns (1992), Journal of Bacteriology 174: 6076-6086), the 3-phosphoglycerate kinase-encoding gene pgk (Eikmanns (1992), Journal of Bacteriology 174: 6076-6086), the pyruvate carboxylase-encoding gene pyc (Eikmanns (1992), Journal of Bacteriology 174: 6076-6086), the triose phosphate isomerase-encoding gene tpi (Eikmanns (1992), Journal of Bacteriology 174: 6076-6086), the homoserine O-acetyltransferase-encoding gene metA (EP 1 108 790 A2; DNA-SEQ NO. 725), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the O-acetylhomoserine sulfhydrylase-encoding gene metY (EP 1 108 790 A2; DNA-SEQ NO. 726), the methionine synthase-encoding gene metH (EP 1 108 790 A2), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO . 467, DNA-SEQ NO. 2767), the serine acetyl transferase-encoding gene cysE (EP 1 108 790 A2; DNA-SEQ NO. 2818), the homoserine dehydrogenase-encoding gene hom (EP 1 108 790 A2; DNA-SEQ NO. 1306)

Thus, it may be advantageous for the production of sulfur-containing fine chemicals, in particular L-methionine, in coryneform bacteria to mutate, at the same time, at least one of the genes below, so that the activity of the corresponding proteins, compared to that of unmutated proteins, is influenced by a metabolic metabolite to a lesser extent or not at all:

the aspartate kinase-encoding gene lysC (EP 1 108 790 A2; DNA-SEQ NO. 281), the pyruvate carboxylase-encoding gene pyc (Eikmanns (1992), Journal of Bacteriology 174: 6076-6086), the homoserine O-acetyltransferase-encoding gene metA (EP 1 108 790 A2; DNA-SEQ NO. 725), the cystathionine gamma-synthase-encoding gene metB (EP 1 108 790 A2; DNA-SEQ NO. 3491), the cystathionine gamma-lyase-encoding gene metC (EP 1 108 790 A2; DNA-SEQ NO. 3061), the serine hydroxymethyltransferase-encoding gene glyA (EP 1 108 790 A2; DNA-SEQ NO. 1110), the O-acetylhomoserine sulfhydrylase-encoding gene metY (EP 1 108 790 A2; DNA-SEQ NO. 726), the methionine synthase-encoding gene metH (EP 1 108 790 A2), the phosphoserine aminotransferase-encoding gene serC (EP 1 108 790 A2; DNA-SEQ NO. 928), a phosphoserine phosphatase-encoding gene serB (EP 1 108 790 A2; DNA-SEQ NO. 334, DNA-SEQ NO. 467, DNA-SEQ NO. 2767), the serine acetyl transferase-encoding gene cysE (EP 1 108 790 A2; DNA-SEQ NO. 2818), the homoserine dehydrogenase-encoding gene hom (EP 1 108 790 A2; DNA-SEQ NO. 1306)

It may be furthermore advantageous for the production of sulfur-containing fine chemicals, in particular L-methionine, in addition to expression and amplification of one of the metF genes of the invention, to attenuate one or more of the following genes, in particular to reduce expression thereof, or to switch them off:

the homoserine kinase-encoding gene thrB (EP 1 108 790 A2; DNA-SEQ NO. 3453),
the threonine dehydratase-encoding gene ilvA (EP 1 108 790 A2; DNA-SEQ NO. 2328),
the threonine synthase-encoding gene thrC (EP 1 108 790 A2; DNA-SEQ NO. 3486),
the meso-diaminopimelate D-dehydrogenase-encoding gene ddh (EP 1 108 790 A2; DNA-SEQ NO. 3494),
the phosphoenolpyruvate carboxykinase-encoding gene pck (EP 1 108 790 A2; DNA-SEQ NO. 3157),
the glucose-6-phosphate 6-isomerase-encoding gene pgi (EP 1 108 790 A2; DNA-SEQ NO. 950),
the pyruvate oxidase-encoding gene poxB (EP 1 108 790 A2; DNA-SEQ NO. 2873),
the dihydrodipicolinate synthase-encoding gene dapA (EP 1 108 790 A2; DNA-SEQ NO. 3476),
the dihydrodipicolinate reductase-encoding gene dapB (EP 1 108 790 A2; DNA-SEQ NO. 3477)
the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, in addition to expression and amplification of one of the metF genes of the invention in coryneform bacteria, to mutate, at the same time, at least one of the following genes in such a way that the enzymic activity of the corresponding protein is partly or completely reduced:

the homoserine kinase-encoding gene thrB (EP 1 108 790 A2; DNA-SEQ NO. 3453),
the threonine dehydratase-encoding gene ilvA (EP 1 108 790 A2; DNA-SEQ NO. 2328),
the threonine synthase-encoding gene thrC (EP 1 108 790 A2; DNA-SEQ NO. 3486),
the meso-diaminopimelate D-dehydrogenase-encoding gene ddh (EP 1 108 790 A2; DNA-SEQ NO. 3494),
the phosphoenolpyruvate carboxykinase-encoding gene pck (EP 1 108 790 A2; DNA-SEQ NO. 3157),
the glucose-6-phosphate 6-isomerase-encoding gene pgi (EP 1 108 790 A2; DNA-SEQ NO. 950),
the pyruvate oxidase-encoding gene poxB (EP 1 108 790 A2; DNA-SEQ NO. 2873),
the dihydrodipicolinate synthase-encoding gene dapA (EP 1 108 790 A2; DNA-SEQ NO. 3476),
the dihydrodipicolinate reductase-encoding gene dapB (EP 1 108 790 A2; DNA-SEQ NO. 3477)
the diaminopicolinate decarboxylase-encoding gene lysA (EP 1 108 790 A2; DNA-SEQ NO. 3451)

It may be furthermore advantageous for the production of sulfur-containing fine chemicals, in particular L-methionine, apart from expression and amplification of a metF gene of the invention, to eliminate unwanted secondary reactions (Nakayama: "Breeding of Amino Acid Producing Microorganisms", in: Overproduction of Microbial Products, Krumphanzl, Sikyta, Vanek (eds.), Academic Press, London, UK, 1982).

The microorganisms produced according to the invention may be cultured continuously or batchwise or in a fed batch or repeated fed batch process to produce sulfur-containing fine chemicals, in particular L-methionine. An overview of known cultivation methods can be found in the textbook by Chmiel (Bioprozeβtechnik 1. Einführung in die Bioverfahrenstechnik (Gustav Fischer Verlag, Stuttgart, 1991)) or in the textbook by Storhas (Bioreaktoren und periphere Einrichtungen (Vieweg Verlag, Braunschweig/Wiesbaden, 1994)).

The culture medium to be used must satisfy the demands of the particular strains in a suitable manner. The textbook "Manual of Methods fur General Bacteriology" by the American Society for Bacteriology (Washington D.C., USA, 1981) contains descriptions of culture media for various microorganisms.

Said media which can be used according to the invention usually comprise one or more carbon sources, nitrogen sources, inorganic salts, vitamins and/or trace elements.

Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts of sugar refining. It may also be advantageous to add mixtures of different carbon sources. Other possible carbon sources are oils and fats such as, for example, soybean oil, sunflower oil, peanut oil and coconut fat, fatty acids such as, for example, palmitic acid, stearic acid and linoleic acid, alcohols such as, for example, glycerol, methanol and ethanol and organic acids such as, for example acetic acid and lactic acid.

Nitrogen sources are usually organic or inorganic hydrogen compounds or materials containing said compounds. Examples of nitrogen sources include ammonia gas or ammonium salts such as ammonium sulfate, ammonium chloride, ammonium phosphate, ammonium carbonate and ammonium nitrate, nitrates, urea, amino acids and complex nitrogen sources such as cornsteep liquor, soybean flour, soybean protein, yeast extract, meat extract and others. The nitrogen sources may be used singly or as mixture.

Inorganic salt compounds which may be included in the media comprise the chloride, phosphorus or sulfate salts of calcium, magnesium, sodium, cobalt, molybdenum, potassium, manganese, zinc, copper and iron.

Inorganic sulfur-containing compounds such as, for example, sulfates, sulfites, dithionites, tetrathionates, thiosulfates, sulfides, or else organic sulfur compounds such as mercaptans and thiols may be used as sources of sulfur for the production of sulfur-containing fine chemicals, in particular of methionine.

Phosphoric acid, potassium dihydrogen phosphate or dipotassium hydrogen phosphate or the corresponding sodium-containing salts may be used as sources of phosphorus.

Chelating agents may be added to the medium in order to keep the metal ions in solution. Particularly suitable chelating agents include dihydroxyphenols such as catechol or protocatechuate and organic acids such as citric acid.

The fermentation media used according to the invention usually also contain other growth factors such as vitamins or growth promoters, which include, for example, biotin, riboflavin, thiamine, folic acid, nicotinic acid, panthothenate and pyridoxine. Growth factors and salts are frequently derived from complex media components such as yeast extract, molasses, cornsteep liquor and the like. It is moreover possible to add suitable precursors to the culture medium. The exact composition of the media heavily depends on the particular experiment and is decided upon individually for each specific case. Information on the optimization of media can be found in the textbook "Applied Microbiol. Physiology, A Practical Approach" (Editors. P. M. Rhodes, P. F. Stanbury, IRL Press (1997) pp. 53-73, ISBN 0 19 963577 3).

Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The culture temperature is normally between 15° C. and 45° C., preferably at from 25° C. to 40° C., and may be kept constant or may be altered during the experiment. The pH of the medium should be in the range from 5 to 8.5, preferably around 7.0. The pH for cultivation can be controlled during cultivation by adding basic compounds such as sodium hydroxide, potassium hydroxide, ammonia and aqueous ammonia or acidic compounds such as phosphoric acid or sulfuric acid. Foaming can be controlled by employing antifoams such as, for example, fatty acid polyglycol esters. To maintain the stability of plasmids it is possible to add to the medium suitable substances having a selective effect, for example antibiotics. Aerobic conditions are maintained by introducing oxygen or oxygen-containing gas mixtures such as, for example, air into the culture. The temperature of the culture is normally 20° C. to 45° C. The culture is continued until formation of the desired product is at a maximum. This aim is normally achieved within 10 to 160 hours.

The fermentation broths obtained in this way, in particular those containing L-methionine, usually contain a dry biomass of from 7.5 to 25% by weight.

An additional advantage is to carry out the fermentation under sugar limitation, at least at the end, but in particular over at least 30% of the fermentation period. This means that during this time the concentration of utilizable sugar in the fermentation medium is maintained at or reduced to $\geq 0$ to 3 g/l.

The fermentation broth is then processed further. The biomass may, according to requirement, be removed completely or partially from the fermentation broth by separation methods such as, for example, centrifugation, filtration, decanting or a combination of these methods or be left completely in said broth.

Subsequently, the fermentation broth may be thickened or concentrated using known methods such as, for example, with the aid of a rotary evaporator, thin film evaporator, falling film evaporator, by reverse osmosis, or by nanofiltration. This concentrated fermentation broth can then be worked up by freeze drying, spray drying, spray granulation or by other methods.

However, it is also possible to further purify the sulfur-containing fine chemicals, in particular L-methionine. To this end, the product-containing broth, after removing the biomass, is subjected to a chromatography using a suitable resin, the desired product or the contaminations being retained completely or partially on the chromatographic resin. These chromatographic steps can be repeated, if necessary, using the same or different chromatographic resin. The skilled worker is familiar with the selection of suitable chromatographic resins and their most effective application. The purified product can be concentrated by filtration or ultrafiltration and stored at a temperature at which the stability of the product is greatest.

The identity and purity of the isolated compound(s) can be determined by techniques of the art. These include high performance liquid chromatography (HPLC), spectroscopic methods, staining methods, thin-layer chromatography, NIRS, enzyme assay or microbiological assays. These analytic methods are summarized in: Patek et al. (1994) Appl. Environ. Microbiol. 60:133-140; Malakhova et al. (1996) Biotekhnologiya 1127-32; and Schmidt et al. (1998) Bioprocess Engineer. 19:67-70. Ulmann's Encyclopedia of Industrial Chemistry (1996) Bd. A27, VCH: Weinheim, pp. 89-90, pp. 521-540, pp. 540-547, pp. 559-566, 575-581 and pp. 581-587; Michal, G., (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Volume 17.

Figure 2:
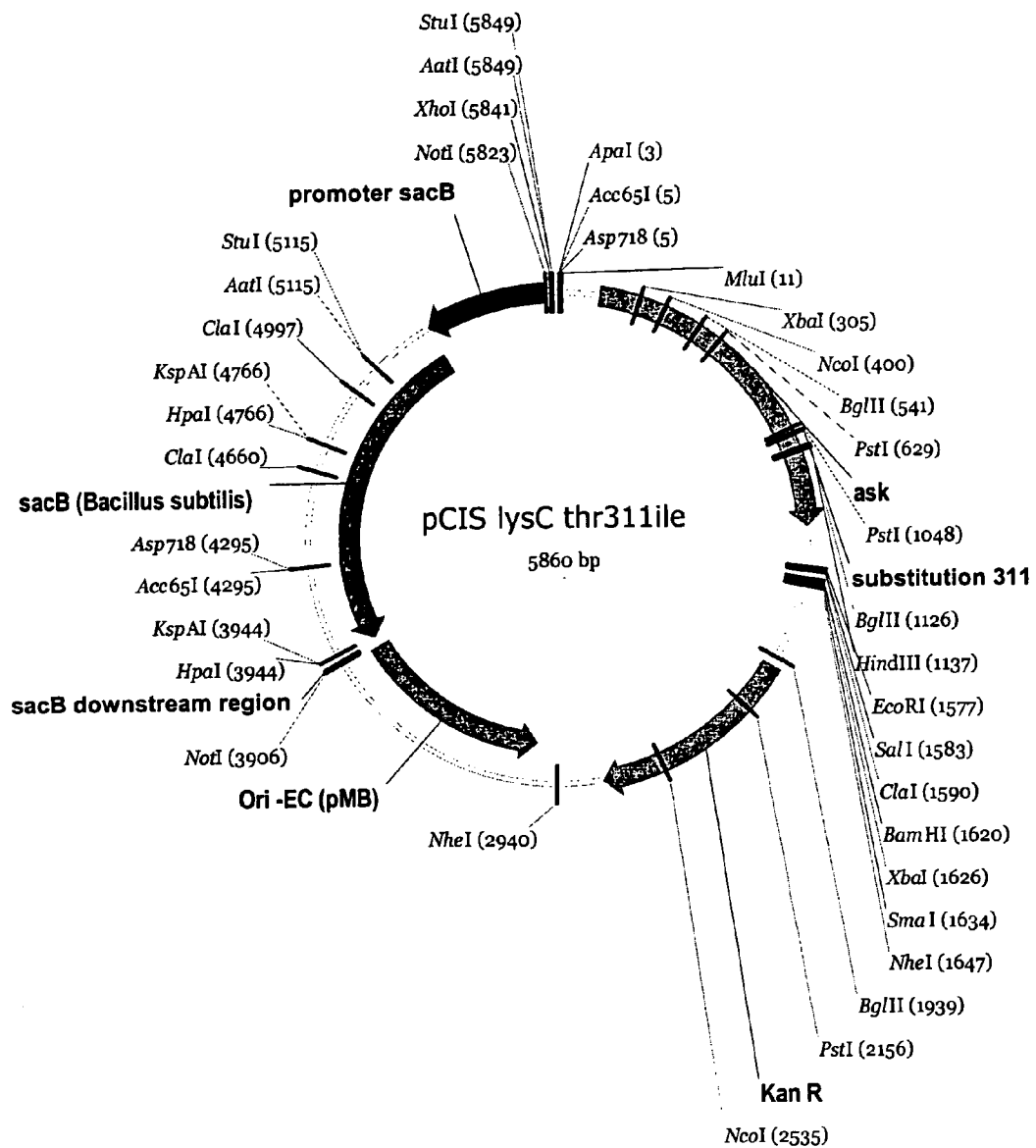
FIG. 2 shows the plasmid map of plasmid pCIS lysC thr311ile.
Figure 3:
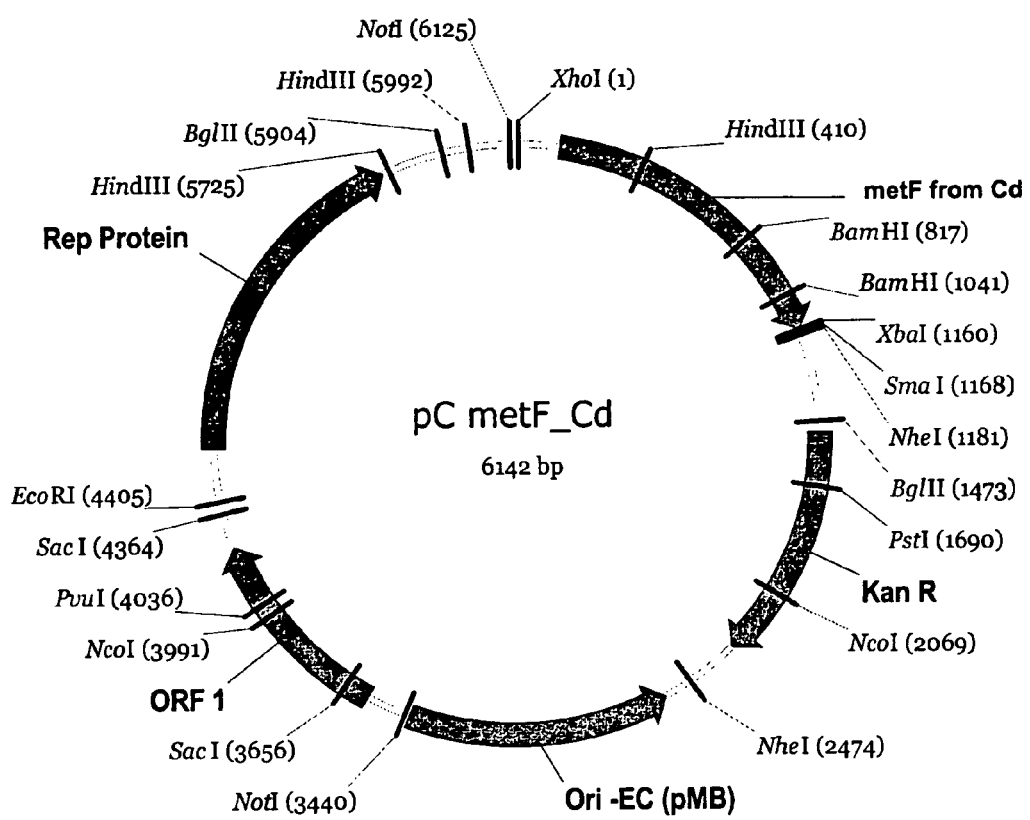
FIG. 3 shows the plasmid map of plasmid pC metF_Cd (*Corynebacterium diphteriae*).

The following nonlimiting examples and attached figures describe the invention in more detail:

FIG. 1 shows the plasmid map for plasmid pClysC;

FIG. 2 shows the plasmid map for plasmid pClSlysCthr311ile;

FIG. 3 shows the plasmid map for plasmid pC_metF_Cd.

Restriction cleavage sites together with their respective positions in brackets are shown in the plasmid maps. Essential sequence segments are printed in bold. KanR means kanamycin resistance gene; ask means aspartate kinase gene.

EXAMPLE 1

Construction of pCLiK5MCS

First, ampicillin resistance and origin of replication of the vector pBR322 were amplified using the oligonucleotides p1.3 (SEQ ID NO:55) and p2.3 (SEQ ID NO:56) with the aid of the polymerase chain reaction (PCR).

```
p1.3 (SEQ ID NO:55)
5'-CCCGGGATCCGCTAGCGGCGCGCCGGCCGGCCCGGTGTGAAATACCGCACAG-3' p2.3 (SEQ ID NO:56)
5'-TCTAGACTCGAGCGGCCGCGGCCGGCCTTTAAATTGAAGACGAAAGGGCCTCG-3'
```

In addition to sequences complementary to pBR322, the oligonucleotide p1.3 (SEQ ID NO:55) contains in 5'-3' direction the cleavage sites for the restriction nucleases SmaI, BamHI, NheI and AscI and the oligonucleotide p2.3 (SEQ ID NO:56) contains in 5'-3' direction the cleavage sites for the restriction endonucleases XbaI, XhoI, NotI and DraI. The PCR reaction was carried out according to a standard method such as that by Innis et al. (PCR Protocols. A Guide to Methods and Applications, Academic Press (1990)) using PfuTurbo polymerase (Stratagene, La Jolla, USA). The DNA fragment obtained of approximately 2.1 kb in size was purified using the GFX™PCR, DNA and gel band purification kit (Amersham Pharmacia, Freiburg) according to the manufacturer's instructions. The blunt ends of the DNA fragment were ligated to one another using the rapid DNA ligation kit (Roche Diagnostics, Mannheim) according to the manufacturer's instructions and the ligation mixture was transformed into competent E. coli XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK1.

Starting from plasmid pWLT1 (Liebl et al., 1992) as template for a PCR reaction, a kanamycin resistance cassette was amplified using the oligonucleotides neo1 (SEQ ID NO:57) and neo2 (SEQ ID NO:58).

```
neo1 (SEQ ID NO:57):
5'-GAGATCTAGACCCGGGGATCCGCTAGCGGGCTGCTAAAGGAAGCGGA-3' neo2 (SEQ ID NO:58):
5'-GAGAGGCGCGCCGCTAGCGTGGGCGAAGAACTCCAGCA-3'
```

Apart from the sequences complementary to pWLT1, the oligonucleotide neo1 contains in 5'-3' direction the cleavage sites for the restriction endonucleases XbaI, SmaI, BamHI, NheI and the oligonucleotide neo2 (SEQ ID NO:58) contains in 5'-3' direction the cleavage sites for the restriction endonucleases AscI and NheI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 1.3 kb in size was purified using the GFX™PCR, DNA and gel band purification kit (Amersham Pharmacia, Freiburg) according to the manufacturer's instructions. The DNA fragment was cleaved with restriction endonucleases XbaI and AscI (New England Biolabs, Beverly, USA) and, following that, again purified using the GFX™PCR, DNA and gel band purification kit (Amersham Pharmacia, Freiburg) according to the manufacturer's instructions. The vector pCLiK1 was likewise cleaved with the restriction endonucleases XbaI and AscI and dephosphorylated using alkaline phosphatase (Roche Diagnostics, Mannheim) according to the manufacturer's instructions. After electrophoresis in a 0.8% strength agarose gel, the linearized vector (approx. 2.1 kb) was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto ampicillin (50 µg/ml)- and kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK2.

The vector pCLiK2 was cleaved with the restriction endonuclease DraI (New England Biolabs, Beverly, USA). After electrophoresis in 0.8% strength agarose gel, an approx. 2.3 kb vector fragment was isolated using the GFX™PCR, DNA and gel band purification kit (Amersham Pharmacia, Freiburg) according to the manufacturer's instructions. This vector fragment was religated with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 µg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK3.

Starting from plasmid pWLQ2 (Liebl et al., 1992) as template for a PCR reaction, the origin of replication pHM1519 was amplified using the oligonucleotides cg1 (SEQ ID NO:59) and cg2 (SEQ ID NO:60).

```
cg1 (SEQ ID NO:59):
5'-GAGAGGGCGGCCGCGCAAAGTCCCGCTTCGTGAA-3' cg2 (SEQ ID NO:60):
5'-GAGAGGGCGGCCGCTCAAGTCGGTCAAGCCACGC-3'
```

Apart from the sequences complementary to pWLQ2, the oligonucleotides cg1 (SEQ ID NO:59) and cg2 (SEQ ID NO:60) contain cleavage sites for the restriction endonuclease NotI. The PCR reaction was carried out using PfuTurbo polymerase (Stratagene, La Jolla, USA) according to a standard method such as that of Innis et al. (PCR Protocols. A Guide to Methods and Applications, Academic Press (1990)). The DNA fragment obtained was approximately 2.7 kb in size and was purified using the GFX™PCR, DNA and gel band purification kit (Amersham Pharmacia, Freiburg) according to the manufacturer's instructions. The DNA fragment was cleaved with restriction endonuclease NotI (New England Biolabs, Beverly, USA) and, following that, again purified using the GFX™PCR, DNA and gel band purification kit (Amersham Pharmacia, Freiburg) according to the manufacturer's instructions. The vector pCLiK3 was likewise cleaved with the restriction endonuclease NotI and dephosphorylated using alkaline 0.8% strength agarose gel, the linearized vector (approx. 5.0 kb) was isolated using the GFX™PCR, DNA and gel band purification kit (Amersham Pharmacia, Freiburg) according to the manufacturer's instructions. This vector fragment was ligated with the synthetic double-stranded DNA fragment with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods as described Sambrook et al. (Molecular Cloning. A Laboratory Manual, Cold Spring Harbor (1989)). Plasmid-carrying cells were selected for by plating out onto kanamycin (20 μg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5MCS.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS is listed as SEQ ID NO: 65.

EXAMPLE 2

Construction of pCLiK5MCS Integrativ SacB

Starting from the plasmid pK19mob (Schäfer et al., Gene 145,69-73(1994)) as template for a PCR reaction, the *Bacillus subtilis* sacB gene (coding for levan sucrase) was amplified using the oligonucleotides BK1732 and BK1733.

```
BK1732 (SEQ ID NO:63):
5'-GAGAGCGGCCGCGATCCTTTTTAACCCATCAC-3'

BK1733 (SEQ ID NO:64):
5'-AGGAGCGGCCGCCATCGGCATTTTCTTTTGCG-3'
```

Apart from the sequences complementary to pEK19 mob-sac, the oligonucleotides BK1732 and BK1733 contain cleavage sites for the restriction endonuclease NotI. The PCR reaction was carried out using PfuTurbo polymerase (Stratagene, La Jolla, USA) using a standard method like that of Innis et al. (PCR Protocols. A Guide to Methods and Applications, Academic Press (1990)). The DNA fragment obtained of approximately 1.9 kb in size was purified using the GFX™PCR, DNA and gel band purification kit (Amersham Pharmacia, Freiburg) according to the manufacturer's instructions. The DNA fragment was cleaved with the restriction endonuclease NotI (New England Biolabs, Beverly, USA) and, following that, again purified using the GFX™PCR, DNA and gel band purification kit (Amersham Pharmacia, Freiburg) according to the manufacturer's instructions.

The vector pCLiK5MCS (prepared according to example 1) was likewise cleaved with the restriction endonuclease NotI and dephosphorylated using alkali phosphatase (I (Roche Diagnostics, Mannheim)) according to the manufacturer's instructions. After electrophoresis in a 0.8% strength agarose gel, an approximately 2.4 kb in size vector fragment was isolated using the GFX™PCR, DNA and gel band purification kit (Amersham Pharmacia, Freiburg) according to the manufacturer's instructions. This vector fragment was ligated with the cleaved PCR fragment with the aid of the rapid DNA ligation kit (Roche Diagnostics, Mannheim) according to the manufacturer's instructions and the ligation mixture was transformed into competent *E. coli* XL-1 Blue (Stratagene, La Jolla, USA) according to standard methods, as described in Sambrook et al. (Molecular Cloning. A Laboratory Manual, Cold Spring Harbor, (1989)). Plasmid-carrying cells were selected for by plating out onto kanamycin (20 μg/ml)-containing LB agar (Lennox, 1955, Virology, 1:190).

The plasmid DNA of an individual clone was isolated using the Qiaprep spin miniprep kit (Qiagen, Hilden) according to the manufacturer's instructions and checked by restriction digests. The plasmid obtained in this way is denoted pCLiK5MCS integrativ sacB.

Sequencing reactions were carried out according to Sanger et al. (1977) Proceedings of the National Academy of Sciences USA 74:5463-5467. The sequencing reactions were fractionated and analyzed by means of ABI Prism 377 (PE Applied Biosystems, Weiterstadt).

The resultant plasmid pCLiK5MCS integrativ sacB is listed as SEQ ID NO: 66.

It is possible to prepare in an analog manner further vectors which are suitable for the inventive expression or overproduction of metF genes.

EXAMPLE 3

Isolation of the lysC Gene from *C. glutamicum* Strain LU1479

The first step of the strain construction is intended to be an allelic substitution of the lysC wild-type gene encoding the enzyme aspartate kinase in *C. glutamicum* ATCC13032, hereinbelow referred to as LU1479. It is intended to carry out a nucleotide substitution in the LysC gene so that, in the resulting protein, the amino acid Thr at position 311 is exchanged for the amino acid Ile.

Starting with the chromosomal DNA from LU1479 as the template for a PCR reaction, an amplification was performed with the oligonucleotide primers SEQ ID NO:67 and SEQ ID NO:68 lysC with the aid of the Pfu-Turbo PCR system (Stratagene USA) following the manufacturer's instructions. Chromosomal DNA from *C. glutamicum* ATCC 13032 was prepared as described by Tauch et al. (1995) Plasmid 33:168-179 or Eikmanns et al. (1994) Microbiology 140: 1817-1828. The amplified fragment is flanked at its 5' end by an SalI restriction cleavage and at its 3' end by an MluI restriction cleavage. Prior to cloning, the amplified fragment was digested by these two restriction enzymes and purified with GFX™PCR, DNA and Gel Band Purification Kit (Amersham Pharmacia, Freiburg).

```
SEQ ID NO:67
5'-GAGAGAGAGACGCGTCCCAGTGGCTGAGACGCATC-3'

SEQ ID NO:68
5'-CTCTCTCTGTCGACGAATTCAATCTTACGGCCTG-3'
```

The resulting polynucleotide was cloned into pCLIK5 MCS integrativ SacB (hereinbelow referred to as pCIS; SEQ ID NO: 66 of Example 2) via the SalI and MluI restriction cleavages and transformed into *E.coli* XL-1 blue. Selection for plasmid-bearing cells was achieved by plating on kanamycin (20 μg/ml)-containing LB Agar (Lennox, 1955, Virology, 1:190). The plasmid was isolated and the expected nucleotide sequence was verified by sequencing. The plasmid DNA was prepared by methods of, and using materials from, Quiagen. Sequencing reactions were carried out as described by Sanger et al. (1977) Proceedings of the National Academy of Sciences USA 74:5463-5467. The sequencing reactions were separated using ABI Prism 377 (PE Applied Biosystems, Weiterstadt) and evaluated. The resulting plasmid pCIS lysC is shown as SEQ ID NO:69. The corresponding plasmid map is shown in FIG. 1.

Sequence SEQ ID NO:69 encompasses the following essential part-regions:

| LOCUS | pCIS\lysC 5860 bp DNA circular |
|---|---|
| FEATURES | Location/Qualifiers |
| CDS[1] | 155..1420 |
| | /vntifkey="4" |
| | /label=lysC |
| CDS | complement[2](3935..5356) |
| | /vntifkey="4" |
| | /label=sacB\(Bacillus\subtilis) |
| promoter | complement(5357..5819) |
| | /vntifkey="30" |
| | /label=Promoter\sacB |
| C_region | complement(3913..3934) |
| | /vntifkey="2" |
| | /label=sacB\downstream region |
| CDS | 1974..2765 |
| | /vntifkey="4" |
| | /label=Kan\R |
| CDS | complement(3032..3892) |
| | /vntifkey="4" |
| | /label=Ori\-EC\(pMB) |

[1]coding sequence
[2]on the complementary strand

EXAMPLE 4

Mutagenesis of the *C. glutamicum* lysC Gene

Site-specific mutagenesis of the *C. glutamicum* lysC gene (example 3) was carried out using the QuickChange Kit (Stratagene/USA) following the manufacturer's instructions. The mutagenesis was carried out in the plasmid pCIS lysC, SEQ ID NO:69. The following oligonucleotide primers were synthesized for the exchange of thr311 for 311ile with the aid of the Quickchange method (Stratagene):

```
SEQ ID NO:70
5'-CGGCACCACCGACATCATCTTCACCTGCCCTCGTTCCG-3'

SEQ ID NO:71
5'-CGGAACGAGGGCAGGTGAAGATGATGTCGGTGGTGCCG-3'
```

The use of these oligonucleotide primers in the Quickchange reaction leads to a substitution of the nucleotide in position 932 (T being substituted for C) in the lysC gene (cf. SEQ ID NO:72) and to an amino acid substitution in position 311 (Thr→Ile) in the corresponding enzyme (cf. SEQ ID NO:73). The resulting amino acid substitution Thr311Ile in the IysC gene was verified by sequencing after transformation into *E.coli* XL1-blue and plasmid preparation. The plasmid was named pCIS lysC thr311ile and is shown as SEQ ID NO:74. The corresponding plasmid map is shown in FIG. 2.

Sequence SEQ ID NO:74 encompasses the following essential part regions:

| LOCUS | pCIS\lysC\thr311ile 5860 bp DNA circular |
|---|---|
| FEATURES | Location/Qualifiers |
| CDS[1] | 155..1420 |
| | /vntifkey="4" |
| | /label=lysC |
| CDS | complement[2](3935..5356) |
| | /vntifkey="4" |
| | /label=sacB\(Bacillus\subtilis) |

-continued

| LOCUS | pCIS\lysC\thr311ile 5860 bp DNA circular |
|---|---|
| FEATURES | Location/Qualifiers |
| promoter | complement(5357..5819) |
| | /vntifkey="30" |
| | /label=Promoter\sacB |
| C_region | complement(3913..3934) |
| | /vntifkey="2" |
| | /label=sacB\downstream region |
| CDS | 1974..2765 |
| | /vntifkey="4" |
| | /label=Kan\R |
| CDS | complement(3032..3892) |
| | /vntifkey="4" |
| | /label=Ori\-EC\(pMB) |

[1]coding sequence
[2]on the complementary strand

The plasmid pCIS lysC thr311ile was transformed into *C. glutamicum* LU1479 by means of electroporation as described by Liebl, et al. (1989) FEMS Microbiology Letters 53:299-303. Modifications of the protocol are described in DE-A-10046870. The chromosomal arrangement of the lysC locus of individual transformants was checked using standard methods by Southern blot and hybridization as described by Sambrook et al. (1989), Molecular Cloning. A Laboratory Manual, Cold Spring Harbor. It was thus ensured that the transformants were those which have the transformed plasmid integrated at the lysC locus by homologous recombination. After such colonies had grown overnight in media without antibiotic, the cells were plated onto a sucrose—CM agar medium (10% sucrose) and incubated for 24 hours at 30° C.

Since the sacB gene which is present in the vector pCIS lysC thr311ile converts sucrose into a toxic product, only those colonies which have the sacB gene deleted between the wild-type lysC gene and the mutated gene lysC thr311ile by a second homologous recombination step are capable of growing. Either the wild-type gene or the mutated gene together with the sacB gene can be deleted during homologous recombination. When the sacB gene is removed together with the wild-type gene, a mutated transformant results.

Growing colonies were picked and examined for a kanamycin-sensitive phenotype. Clones with deleted SacB gene must simultaneously show kanamycin-sensitive growth behavior. Such Kan-sensitive clones were studied in a shake flask for their lysine productivity (see example 6). The untreated strain LU1479 was grown for comparison purposes. Clones whose lysine production was increased over that of the control were selected, chromosomal DNA was obtained, and the corresponding region of the lysC gene was amplified by a PCR reaction and sequenced. One such clone with the property of an increased lysine synthesis and confirmed mutation in lysC at position 932 was named LU1479 lysC 311ile.

EXAMPLE 5

Preparation of Ethionine-Resistant *C. glutamicum* Strains

In the second strain construction step, the resulting strain LU1479 lysC 311ile (example 4) was treated in order to induce resistance to ethionine (Kase, H. Nakayama K. Agr. Biol. Chem. 39 153-106 1975 L-methionine production by methionine analog-resistant mutants of *Corynebacterium*

*glutamicum*): an overnight culture in BHI medium (Difco) was washed in citrate buffer (50 mM pH 5.5) and treated for 20 min at 30° C. with N-methylnitrosoguanidine (10 mg/ml in 50 mM citrate pH 5.5). After treatment with the chemical mutagen N-methylnitrosoguanidine, the cells were washed (citrate buffer 50 mM pH 5.5) and plated out on a medium composed of the following components, based on 500 ml: 10 g $(NH_4)_2SO_4$, 0.5 g $KH_2PO_4$, 0.5 g $K_2HPO_4$, 0.125 g $MgSO_4.7H_2O$, 21 g MOPS, 50 mg $CaCl_2$, 15 mg proteocatechuate, 0.5 mg biotin, 1 mg thiamine, 5 g/l D,L-ethionine (Sigma Chemicals Germany), pH 7.0. In addition, the medium comprised 0.5 ml of a microsalt solution of: 10 g/l $FeSO_4.7H_2O$, 1 g/l $MnSO_4.H_2O$, 0.1 g/l $ZnSO_4.7H_2O$, 0.02 g/l $CuSO_4$, 0.002 g/l $NiCl_2.6H_2O$; all salts were dissolved in 0.1 M HCl. The finished medium was filter-sterilized and, after addition of 40 ml of sterile 50% glucose solution, liquid sterile agar was added in a final concentration of 1.5% agar and the mixture was poured into culture dishes.

Cells which had undergone mutagenic treatment were applied to plates containing the above-described medium and incubated for 3-7 days at 30° C. Resulting clones were isolated, and individual clones were isolated at least once on the selection medium and then analyzed for their methionine productivity in a shake flask in medium 11 (see example 6

EXAMPLE 6

Preparation of Methionine Using the Strain LU1479 lysC 311ile ET-16.

The strains generated in Example 5 were grown for 2 days at 30° C. on an agar plate comprising CM medium.

CM agar:

10.0 g/l D-glucose, 2.5 g/l NaCl, 2.0 g/l urea, 10.0 g/l Bacto peptone (Difco), 5.0 g/l yeast extract (Difco), 5.0 g/l beef extract (Difco), 22.0 g/l agar (Difco), autoclaved (20 min., 121° C.)

The cells were subsequently scraped from the plate and resuspended in saline. For the main culture, 10 ml of medium II and 0.5 g of autoclaved $CaCO_3$ (Riedel de Haen) in a 100 ml Erlenmeyer flask were inoculated with the cell suspension to an OD 600 nm of 1.5 and incubated for 72 h at 30° C. on an orbital shaker at 200 rpm.

| Medium II: | |
|---|---|
| 40 g/l | sucrose |
| 60 g/l | molasses (based on 100% sugar content) |
| 10 g/l | $(NH_4)_2SO_4$ |
| 0.4 g/l | $MgSO_4*7H_2O$ |
| 0.6 g/l | $KH_2PO_4$ |
| 0.3 mg/l | thiamine*HCl |
| 1 mg/l | biotin (from a 1 mg/ml filter-sterilized stock solution brought to pH 8.0 with $NH_4OH$) |
| 2 mg/l | $FeSO_4$ |
| 2 mg/l | $MnSO_4$ | a pH of 7.8 was established with $NH_4OH$ and the mixture was autoclaved (121° C., 20 min). In addition, vitamin B12 (hydroxycobalamin Sigma Chemicals) was added from a stock solution (200 µg/ml, filter-sterilized) to a final concentration of 100 µg/l Methionine formed, as well as other amino acids in the culture broth, were [lacuna] with the aid of the Agilent amino acid acid determination method on an Agilent 1100 Series LC System HPLC. The amino acid mixture was separated on a Hypersil M column (Agilent). Pre-column derivatization with ortho-phthalaldehyde allowed the quantification of the amino acids formed. The amino acid mixture was separated on a column.

Clones whose methionine productivity was at least twice as high as that of the original strain LU 1479 lysC 311 ile were isolated. One such clone was employed in the further experiments and was named LU 1479 lysC 311ile ET-16.

EXAMPLE 7

Cloning metF from *Corynebacterium diphtheriae* and Cloning into the Plasmid pC metF_Cd Chromosomal DNA of *Corynebacterium diphtheriae* was obtained from the American Type Strain Culture Collection (ATCC, Atlanta-USA), Cat. No. 700971D from strain ATCC 700971.

Using the oligonucleotide primers SEQ ID NO:75 and SEQ ID NO:76, the *C. diphtheriae* chromosomal DNA as template and Pfu Turbo polymerase (Stratagene), a DNA fragment of approx. 1.2 kb, which comprises the metF gene including a noncoding 5' region (promoter region), was amplified with the aid of the polymerase chain reaction (PCR) following standard methods such as Innis et al. (1990) PCR Protocols. A Guide to Methods and Applications, Academic Press. The amplified fragment is flanked at its 5' end by an XhoI restriction cleavage site and at the 3' end by an XbaI restriction cleavage site, which had been introduced via the oligonucleotide primers.

```
SEQ ID NO:75
5'-GAGACTCGAGGTAGACTTTAAACCCATATTAG-3'
and

SEQ ID NO:76
5'-GAAGTCTAGATTAGCGAATAGCGTCGTGG-3'
```

The resulting DNA fragment was purified with the GFX™PCR, DNA and Gel Band Purification Kit (Amersham Pharmacia, Freiburg) following the manufacturer's instructions. Thereafter, it was cleaved with the restriction enzymes XhoI and XbaI (Roche Diagnostics, Mannheim) and separated by gel electrophoresis. The approximately 1.2 kb DNA fragment was subsequently isolated from the agarose using the GFX™PCR, DNA and Gel Band Purification Kit (Amersham Pharmacia, Freiburg).

The vector pClik5MCS SEQ ID NO: 65, hereinbelow referred to as pC, was cut with the restriction enzymes XhoI and XbaI (Roche Diagnostics, Mannheim), and an approximately 5 kb fragment was separated by electrophoresis and then isolated using the GFX™PCR, DNA and Gel Band Purification Kit.

The vector fragment was ligated together with the PCR fragment with the aid of the Rapid DNA Ligation Kit (Roche Diagnostics, Mannheim) following the manufacturer's instructions, and the ligation reaction was transformed into competent *E.coli* XL-1 Blue (Stratagene, La Jolla, USA) using standard methods as described in Sambrook et al. (Molecular Cloning. A Laboratory Manual, Cold Spring Harbor, (1989)). A selection for plasmid-bearing cells was achieved by plating onto kanamycin (20 μg/ml)-containing LB agar (Lennox, 1955, Virology, 1:190).

The plasmid DNA was prepared using methods of, and materials from, Quiagen. Sequencing reactions were carried out as described by Sanger et al. (1977) Proceedings of the National Academy of Sciences USA 74:5463-5467. The sequencing reactions were separated and evaluated by means of ABI Prism 377 (PE Applied Biosystems, Weiterstadt).

The resulting plasmid pC metF_Cd (*Corynebacterium diphtheriae*) is shown as SEQ ID NO:77. The corresponding plasmid map is shown in FIG. 3.

| pC_metF_Cd 6142 bp DNA circular | |
|---|---|
| FEATURE | Location/Qualifiers |
| CDS | 136..1158 |
|  | =metF_Coryne\diphtheriae |
| CDS | 1508..2299 |
|  | =Kan\R |
| CDS | 4580..5701 |
|  | =Rep\Protein |
| CDS | 3572..4246 |
|  | =ORF\1 |
| CDS | complement(2566..3426) |
|  | =Ori\-EC\(pMB) |

EXAMPLE 8

Transformation of the Strain LU1479 lysC 311ile ET-16 with the plasmid pC metF_Cd The strain LU1479 lysC 311ile ET-16 was transformed with the plasmid pC metF_Cd by the above-described method (Liebl, et al. (1989) FEMS Microbiology Letters 53:299-303). The transformation mixture was plated onto CM plates which additionally comprised 20 mg/l kanamycin in order to obtain a selection for plasmid-containing cells. Resulting Kan-resistant clones were picked and individual clones were isolated. The methionine productivity of the clones was studied in a shake-flask experiment (see Example 6). The strain LU1479 lysC 311ile ET-16 pC metF_Cd produced significantly more methionine in comparison with LU1479 lysC 311ile ET-16.

We claim:

1. A method for the fermentative production of L-methionine, which comprises the following steps:
    a) fermenting in a medium cells of a coryneform bacterium for producing L-methionine, the coryneform bacteria expressing at least one heterologous nucleotide sequence which codes for a protein with methylenetetrahydrofolate reductase (metF) activity, wherein said heterologous nucleotide sequence comprises a nucleotide sequence encoding a metF protein having an amino acid sequence as set forth in SEQ ID NO: 2 or comprises a nucleotide sequence encoding a metF protein having an amino acid sequence with 95% homology or more to the sequence as set forth in SEQ ID NO: 2;
    b) concentrating L-methionine in the medium or in the bacterial cells, and
    c) isolating L-methionine.

2. The method as claimed in claim 1, wherein the metF-encoding sequence comprises a coding sequence as set forth in SEQ ID NO:1.

3. The method as claimed in claim 1, wherein the metF-encoding sequence codes for a protein with metF activity, said protein comprising an amino acid sequence as set forth in SEQ ID NO:2.

4. The method as claimed in claim 1, wherein the coding metF sequence is a DNA or RNA which can be replicated in coryneform bacteria or is stably integrated into the chromosome.

5. The method as claimed in claim 4, wherein
    a) a bacteria strain transformed with a plasmid vector carrying at least one copy of the coding metF sequence under the control of regulatory sequences is used, or
    b) a strain in which the coding metF sequence has been integrated into the bacteria chromosome is used.

6. The method as claimed in claim 1, wherein the coding metF sequence is overexpressed.

7. The method as claimed in claim 1, wherein bacteria are fermented in which additionally at least one further gene of the biosynthetic pathway of L-methionine has been overexpressed.

8. The method as claimed in claim 1, wherein coryneform bacteria are fermented in which, at the same time, at least one of the genes from among
    a) a lysC gene derived from a coryneform bacterium, which encodes an aspartate kinase,
    b) the glyceraldehyde-3-phosphate dehydrogenase-encoding gene gap,
    c) the 3-phosphoglycerate kinase-encoding gene pgk,
    d) the pyruvate carboxylase-encoding gene pyc,
    e) the triose phosphate isomerase-encoding gene tpi,
    f) the homoserine O-acetyltransferase-encoding gene metA,
    g) the cystathionine gamma-synthase-encoding gene metB,
    h) the cystathionine gamma-lyase-encoding gene metC,
    i) the serine hydroxymethyltransferase-encoding gene glyA,
    j) the O-acetylhomoserine sulfhydrylase-encoding gene metY,
    k) the vitamin B12-dependent methionine synthase-encoding gene metH,
    l) the phosphoserine aminotransferase-encoding gene serC,
    m) the phosphoserine phosphatase-encoding gene serB,
    n) the serine acetyltransferase-encoding gene cysE, or
    o) the hom gene, which encodes a homoserine dehydrogenase, is overexpressed.

9. The method as claimed in claim 1, wherein the coryneform bacterium is of the species *Corynebacterium glutamicum*.

10. A method for the production of L-methionine, which comprises the following steps:
    a) fermenting in a medium cells of a coryneform bacterium fur producing of L-methionine, said coryneform bacteria expressing at least one heterologous nucleotide sequence which codes for a protein with methylenetetrahydrofolate reductase (metF) activity, wherein the heterologous nucleotide sequence comprises a nucleotide sequence having 95% identity or more to the sequence as set forth in SEQ ID NO; 1;
    b) concentrating L-methionine in the medium or in the bacterial cells; and
    c) isolating L-methionine.

11. The method of claim 10, wherein the coding metF sequence is a DNA or RNA which can be replicated in coryneform bacteria or is stably integrated into the chromosome.

12. The method of claim 10, wherein
    a) a bacteria strain transformed with a plasmid vector carrying at least one copy of the coding metF sequence under the control of regulatory sequences is used, or b) a strain in which the coding metF sequence has been integrated into the bacteria chromosome is used.

13. The method of claim 10, wherein the coding metF sequence is overexpressed.

14. The method of claim 10, wherein bacteria are fermented in which additionally at least one further gene of the biosynthetic pathway of L-methionine has been overexpressed.

15. The method of claim 10, wherein the coryneform bacterium is of the species *Corynebacterium glutamicum*.

16. The method as claimed in claim 1, wherein coryneform bacteria are fermented in which, at the same time, a lysC gene derived from a coryneform bacterium, which encodes an aspartate kinase, is overexpressed.

17. The method as claimed in claim 16, wherein the lysC gene is derived from *C. glutamicum*.

* * * * *

UNITED STATES PATENT AND TRADEMARK OFFICE
CERTIFICATE OF CORRECTION

PATENT NO.        : 7,282,357 B2
APPLICATION NO.   : 10/525907
DATED             : October 16, 2007
INVENTOR(S)       : Burkhard Kröger et al.

It is certified that error appears in the above-identified patent and that said Letters Patent is hereby corrected as shown below:

On the Title Page, item [75]:

In the Inventors, "Corinna Kolpprogge" should read -- Corinna Klopprogge --.

On the Title Page, item [56]:

In the Reference Cited:

starting with Matthews, R. G., "methlonine" should read -- methionine --.

starting with Matthews, R. G., "Methods in Enzym, 122, 372, 1986, Enzymology, vol. 122," should read -- Methods in Enzymology, vol. 122, 1986 --.

in Page 2 under OTHER PUBLICATIONS, left Column, starting with O'Regan, M., "phosphoenolpyruvate, Gene, 1989, 77:237, carboxylase-coding" should read -- phosphoenolpyruvate carboxylase-coding --.

starting with Schwarzer, A., "glutemicum" should read -- glutamicum --.

in Page 2 under OTHER PUBLICATIONS, right Column, starting with SchÅfer, A., "SchÅfer" should read -- Schäfer --.

starting with Spratt, B. G., "pUC9, Gene 1986, 41: 337 pEMBL8" should read -- pUC9, pEMBL8 --.

in Page 3 under OTHER PUBLICATIONS, right Column, starting with Eikmanns, B. J., "glutemicum" should read -- glutamicum --.

UNITED STATES PATENT AND TRADEMARK OFFICE
CERTIFICATE OF CORRECTION

PATENT NO. : 7,282,357 B2
APPLICATION NO. : 10/525907
DATED : October 16, 2007
INVENTOR(S) : Burkhard Kröger et al.

It is certified that error appears in the above-identified patent and that said Letters Patent is hereby corrected as shown below:

In the Claims:

In Claim 8, in column 178 and on line 42, "horn" should read -- hom --.

In Claim 10, in column 178 and on line 50, "fur" should read -- for --.

Signed and Sealed this

Twenty-fourth Day of November, 2009

David J. Kappos
*Director of the United States Patent and Trademark Office*

SEQUENCE LISTING

<160> NUMBER OF SEQ ID NOS: 77

<210> SEQ ID NO 1
<211> LENGTH: 984
<212> TYPE: DNA
<213> ORGANISM: corynebacterium diphteriae
<220> FEATURE:
<221> NAME/KEY: CDS
<222> LOCATION: (1)..(981)
<223> OTHER INFORMATION: RDI01260

<400> SEQUENCE: 1

```
atg tct gca caa ccg cta cct gct gcg tat cag cgc aca atc acc gat      48
Met Ser Ala Gln Pro Leu Pro Ala Ala Tyr Gln Arg Thr Ile Thr Asp
 1               5                  10                  15 gtc att tcc atg cca aca ccg ggc cag gtt ccg ttt tct gta gag ttt      96
Val Ile Ser Met Pro Thr Pro Gly Gln Val Pro Phe Ser Val Glu Phe
             20                  25                  30 atg ccg cca cga gat gag gca gca gaa gag cga ctc tgg aaa gcc gcc     144
Met Pro Pro Arg Asp Glu Ala Ala Glu Glu Arg Leu Trp Lys Ala Ala
         35                  40                  45 gaa gca ttt cac gac tta gga gcc tct ttt gtc tcc gtt act tat ggt     192
Glu Ala Phe His Asp Leu Gly Ala Ser Phe Val Ser Val Thr Tyr Gly
     50                  55                  60 gca ggc gga tct agc cgc gag cgc aca atg cgt gtc gcg cac aag ctt     240
Ala Gly Gly Ser Ser Arg Glu Arg Thr Met Arg Val Ala His Lys Leu
 65                  70                  75                  80 tct cgt cat ccg ttg acc acg ctc gtt cat ctc acg ctt gtg gaa cac     288
Ser Arg His Pro Leu Thr Thr Leu Val His Leu Thr Leu Val Glu His
                 85                  90                  95 acc caa gaa gaa tta gaa gaa att ctg tgc act tat gcg tcc cac ggg     336
Thr Gln Glu Glu Leu Glu Glu Ile Leu Cys Thr Tyr Ala Ser His Gly
            100                 105                 110 ttg tct aac tta ctt gcc ttg cga ggc gat ccc cct ggc act gac ccg     384
Leu Ser Asn Leu Leu Ala Leu Arg Gly Asp Pro Pro Gly Thr Asp Pro
```

```
                115                 120                 125
atg gct ccg tgg gtc cct acc gca ggc ggc cta gat tat gcc aaa gat     432
Met Ala Pro Trp Val Pro Thr Ala Gly Gly Leu Asp Tyr Ala Lys Asp
    130                 135                 140 ttg atc gac ctc gtg cgc aag act gag cag acc tcg cac ttt cag gta     480
Leu Ile Asp Leu Val Arg Lys Thr Glu Gln Thr Ser His Phe Gln Val
145                 150                 155                 160 gga att gct agt ttc cca gaa ggg cac tac cga gcg cct agc att gag     528
Gly Ile Ala Ser Phe Pro Glu Gly His Tyr Arg Ala Pro Ser Ile Glu
                165                 170                 175 gcg gat acg caa ttt aca ttg gaa aag ctg cga gct ggc gca gag ttt     576
Ala Asp Thr Gln Phe Thr Leu Glu Lys Leu Arg Ala Gly Ala Glu Phe
            180                 185                 190 tcg att acc cag atg ttt ttt gat gtc gat cac tat tta cga ctg cga     624
Ser Ile Thr Gln Met Phe Phe Asp Val Asp His Tyr Leu Arg Leu Arg
        195                 200                 205 gat cgc ttg gtt aag gcg gat cct gaa cat gga tca aag ccg atc atc     672
Asp Arg Leu Val Lys Ala Asp Pro Glu His Gly Ser Lys Pro Ile Ile
    210                 215                 220 cca gga ctt atg ccc att acc agc ttg agg tcg gtt cgt agg cag atg     720
Pro Gly Leu Met Pro Ile Thr Ser Leu Arg Ser Val Arg Arg Gln Met
225                 230                 235                 240 gaa tta gca ggt gcc acc ttg cct aag gct tta gaa aaa cgg ctt ctc     768
Glu Leu Ala Gly Ala Thr Leu Pro Lys Ala Leu Glu Lys Arg Leu Leu
                245                 250                 255 gac gca gcg cgc ggc gat gag gaa gct cat cgc ggc gat att cgc aaa     816
Asp Ala Ala Arg Gly Asp Glu Glu Ala His Arg Gly Asp Ile Arg Lys
            260                 265                 270 gta gga atc gaa gtc act act gag atg gca cag cgt ctt att tct gaa     864
Val Gly Ile Glu Val Thr Thr Glu Met Ala Gln Arg Leu Ile Ser Glu
        275                 280                 285 ggg atc cca gac atc cat ttc atg acc atg aat tat gtt cga gcg acc     912
Gly Ile Pro Asp Ile His Phe Met Thr Met Asn Tyr Val Arg Ala Thr
    290                 295                 300 caa gaa gta ctc cat aat ctc ggc atg gcg ccc gcg tgg gga aca cag     960
Gln Glu Val Leu His Asn Leu Gly Met Ala Pro Ala Trp Gly Thr Gln
305                 310                 315                 320 caa ggc cac gac gct att cgc taa                                     984
Gln Gly His Asp Ala Ile Arg
                325

<210> SEQ ID NO 2
<211> LENGTH: 327
<212> TYPE: PRT
<213> ORGANISM: corynebacterium diphteriae

<400> SEQUENCE: 2

Met Ser Ala Gln Pro Leu Pro Ala Ala Tyr Gln Arg Thr Ile Thr Asp
1               5                   10                  15

Val Ile Ser Met Pro Thr P

```
Thr Gln Glu Glu Leu Glu Ile Leu Cys Thr Tyr Ala Ser His Gly
            100                 105                 110

Leu Ser Asn Leu Leu Ala Leu Arg Gly Asp Pro Gly Thr Asp Pro
        115                 120                 125

Met Ala Pro Trp Val Pro Thr Ala Gly Gly Leu Asp Tyr Ala Lys Asp
    130                 135                 140

Leu Ile Asp Leu Val Arg Lys Thr Glu Gln Thr Ser His Phe Gln Val
145                 150                 155                 160

Gly Ile Ala Ser Phe Pro Glu Gly His Tyr Arg Ala Pro Ser Ile Glu
                165                 170                 175

Ala Asp Thr Gln Phe Thr Leu Glu Lys Leu Arg Ala Gly Ala Glu Phe
            180                 185                 190

Ser Ile Thr Gln Met Phe Phe Asp Val Asp His Tyr Leu Arg Leu Arg
        195                 200                 205

Asp Arg Leu Val Lys Ala Asp Pro Glu His Gly Ser Lys Pro Ile Ile
    210                 215                 220

Pro Gly Leu Met Pro Ile Thr Ser Leu Arg Ser Val Arg Arg Gln Met
225                 230                 235                 240

Glu Leu Ala Gly Ala Thr Leu Pro Lys Ala Leu Glu Lys Arg Leu Leu
                245                 250                 255

Asp Ala Ala Arg Gly Asp Glu Glu Ala His Arg Gly Asp Ile Arg Lys
            260                 265                 270

Val Gly Ile Glu Val Thr Thr Glu Met Ala Gln Arg Leu Ile Ser Glu
        275                 280                 285

Gly Ile Pro Asp Ile His Phe Met Thr Met Asn Tyr Val Arg Ala Thr
    290                 295                 300

Gln Glu Val Leu His Asn Leu Gly Met Ala Pro Ala Trp Gly Thr Gln
305                 310                 315                 320

Gln Gly His Asp Ala Ile Arg
                325

<210> SEQ ID NO 3
<211> LENGTH: 924
<212> TYPE: DNA
<213> ORGANISM: Streptomyces lividans
<220> FEATURE:
<221> NAME/KEY: CDS
<222> LOCATION: (1)..(921)
<223> OTHER INFORMATION: RSV00084

<400> SEQUENCE: 3 atg gcc ctc gga acc gca agc acg agg acg gat cgc gcc cgc acg gtg     48
Met Ala Leu Gly Thr Ala Ser Thr Arg Thr Asp Arg Ala Arg Thr Val
 1               5                  10                  15 cgt gac atc ctc gcc acc ggc aag acg acg tac tcg ttc gag ttc tcg     96
Arg Asp Ile Leu Ala Thr Gly Lys Thr Thr Tyr Ser Phe Glu Phe Ser
            20                  25                  30 gcg ccg aag acg ccc aag ggc gag aag aac ctc tgg agc gcg ctg cgg    144
Ala Pro Lys Thr Pro Lys Gly Glu Lys Asn Leu Trp Ser Ala Leu Arg
        35                  40                  45 cgg gtc gag gcc gtg gcc ccg gac ttc gtc tcc gtg acc tac ggc gcc    192
Arg Val Glu Ala Val Ala Pro Asp Phe Val Ser Val Thr Tyr Gly Ala
    50                  55                  60 ggc ggc tcc acg cgc gcc ggc acg gtc cgc gag acc cag cag atc gtc    240
Gly Gly Ser Thr Arg Ala Gly Thr Val Arg Glu Thr Gln Gln Ile Val
65                  70                  75                  80 gcc gac acc acg ctg acc ccg gtg gcc cac ctc acc gcc gtc gac cac    288
```

-continued

```
Ala Asp Thr Thr Leu Thr Pro Val Ala His Leu Thr Ala Val Asp His
                 85                  90                  95 tcc gtc gcc gag ctg cgc aac atc atc ggc cag tac gcc gac gcc ggg    336
Ser Val Ala Glu Leu Arg Asn Ile Ile Gly Gln Tyr Ala Asp Ala Gly
            100                 105                 110 atc cgc aac atg ctg gcc gtg cgc ggc gac ccg ccc ggc gac ccg aac    384
Ile Arg Asn Met Leu Ala Val Arg Gly Asp Pro Pro Gly Asp Pro Asn
        115                 120                 125 gcc gac tgg atc gcg cac ccc gag ggc ctg acc tac gcg gcc gaa ctg    432
Ala Asp Trp Ile Ala His Pro Glu Gly Leu Thr Tyr Ala Ala Glu Leu
    130                 135                 140 gtc agg ctc atc aag gag tcg gga gac ttc tgc gtc ggc gtc gcc gcc    480
Val Arg Leu Ile Lys Glu Ser Gly Asp Phe Cys Val Gly Val Ala Ala
145                 150                 155                 160 ttc ccc gag atg cac ccg cgc tcc gcc gac tgg gac acg gac gtc acg    528
Phe Pro Glu Met His Pro Arg Ser Ala Asp Trp Asp Thr Asp Val Thr
                165                 170                 175 aac ttc gtc gac aag tgc cgg gcc ggc gcc gac tac gcc atc acc cag    576
Asn Phe Val Asp Lys Cys Arg Ala Gly Ala Asp Tyr Ala Ile Thr Gln
            180                 185                 190 atg ttc ttc cag ccc gac tcc tac ctc cgg ctg cgc gac cgg gtc gcc    624
Met Phe Phe Gln Pro Asp Ser Tyr Leu Arg Leu Arg Asp Arg Val Ala
        195                 200                 205 gcg gcc ggc tgc gcg acc ccg gtc att ccc gag gtc atg ccg gtg acc    672
Ala Ala Gly Cys Ala Thr Pro Val Ile Pro Glu Val Met Pro Val Thr
    210                 215                 220 agt gtg aag atg ctg gag agg ttg cca aag ctc agc aac gcc tcg ttc    720
Ser Val Lys Met Leu Glu Arg Leu Pro Lys Leu Ser Asn Ala Ser Phe
225                 230                 235                 240 ccg gcg gag ctg aaa gag cgg atc ctc aca gcc aag gac gat ccg gcg    768
Pro Ala Glu Leu Lys Glu Arg Ile Leu Thr Ala Lys Asp Asp Pro Ala
                245                 250                 255 gct gta cgc tcg atc ggc atc gag ttc gcc acg gag ttc tgc gcg cgg    816
Ala Val Arg Ser Ile Gly Ile Glu Phe Ala Thr Glu Phe Cys Ala Arg
            260                 265                 270 ctg ctg gcc gag gga gtg cca gga ctg cac ttc atc acg ctc aac aac    864
Leu Leu Ala Glu Gly Val Pro Gly Leu His Phe Ile Thr Leu Asn Asn
        275                 280                 285 tcc acg gcg acg ctg gaa atc tac gag aac ctg ggc ctg cac cac cca    912
Ser Thr Ala Thr Leu Glu Ile Tyr Glu Asn Leu Gly Leu His His Pro
    290                 295                 300 ccg cgg gcc tag                                                    924
Pro Arg Ala
305

<210> SEQ ID NO 4
<211> LENGTH: 307
<212> TYPE: PRT
<213> ORGANISM: Streptomyces lividans

<400> SEQUENCE: 4

Met Ala Leu Gly Thr Ala Ser Thr Arg Thr Asp Arg Ala Arg Thr Val
  1               5                  10                  15

Arg Asp Ile Leu Ala Thr Gly Lys Thr Thr Tyr Ser Phe Glu Phe Ser
             20                  25                  30

Ala Pro Lys Thr Pro Lys Gly Glu Lys Asn Leu Trp Ser Ala Leu Arg
         35                  40                  45

Arg Val Glu Ala Val Ala Pro Asp Phe Val Ser Val Thr Tyr Gly Ala
     50                  55                  60
```

```
Gly Gly Ser Thr Arg Ala Gly Thr Val Arg Glu Thr Gln Gln Ile Val
 65                  70                  75                  80

Ala Asp Thr Thr Leu Thr Pro Val Ala His Leu Thr Ala Val Asp His
                 85                  90                  95

Ser Val Ala Glu Leu Arg Asn Ile Ile Gly Gln Tyr Ala Asp Ala Gly
            100                 105                 110

Ile Arg Asn Met Leu Ala Val Arg Gly Asp Pro Pro Gly Asp Pro Asn
        115                 120                 125

Ala Asp Trp Ile Ala His Pro Glu Gly Leu Thr Tyr Ala Ala Glu Leu
    130                 135                 140

Val Arg Leu Ile Lys Glu Ser Gly Asp Phe Cys Val Gly Val Ala Ala
145                 150                 155                 160

Phe Pro Glu Met His Pro Arg Ser Ala Asp Trp Asp Thr Asp Val Thr
                165                 170                 175

Asn Phe Val Asp Lys Cys Arg Ala Gly Ala Asp Tyr Ala Ile Thr Gln
            180                 185                 190

Met Phe Phe Gln Pro Asp Ser Tyr Leu Arg Leu Arg Asp Arg Val Ala
        195                 200                 205

Ala Ala Gly Cys Ala Thr Pro Val Ile Pro Glu Val Met Pro Val Thr
    210                 215                 220

Ser Val Lys Met Leu Glu Arg Leu Pro Lys Leu Ser Asn Ala Ser Phe
225                 230                 235                 240

Pro Ala Glu Leu Lys Glu Arg Ile Leu Thr Ala Lys Asp Asp Pro Ala
                245                 250                 255

Ala Val Arg Ser Ile Gly Ile Glu Phe Ala Thr Glu Phe Cys Ala Arg
            260                 265                 270

Leu Leu Ala Glu Gly Val Pro Gly Leu His Phe Ile Thr Leu Asn Asn
        275                 280                 285

Ser Thr Ala Thr Leu Glu Ile Tyr Glu Asn Leu Gly Leu His His Pro
    290                 295                 300

Pro Arg Ala
305

<210> SEQ ID NO 5
<211> LENGTH: 924
<212> TYPE: DNA
<213> ORGANISM: Streptomyces coelicolor
<220> FEATURE:
<221> NAME/KEY: CDS
<222> LOCATION: (1)..(921)
<223> OTHER INFORMATION: RSX01699

<400> SEQUENCE: 5 atg gcc ctc gga acc gca agc acg agg acg gat cgc gcc cgc acg gtg      48
Met Ala Leu Gly Thr Ala Ser Thr Arg Thr Asp Arg Ala Arg Thr Val
  1               5                  10                  15 cgt gac atc ctc gcc acc ggc aag acg acg tac tcg ttc gag ttc tcg      96
Arg Asp Ile Leu Ala Thr Gly Lys Thr Thr Tyr Ser Phe Glu Phe Ser
             20                  25                  30 gcg ccg aag acg ccc aag ggc gag agg aac ctc tgg agc gcg ctg cgg     144
Ala Pro Lys Thr Pro Lys Gly Glu Arg Asn Leu Trp Ser Ala Leu Arg
         35                  40                  45 cgg gtc gag gcc gtg gcc ccg gac ttc gtc tcc gtg acc tac ggc gcc     192
Arg Val Glu Ala Val Ala Pro Asp Phe Val Ser Val Thr Tyr Gly Ala
     50                  55                  60 ggc ggc tcc acg cgc gcc ggc acg gtc cgc gag acc cag cag atc gtc     240
Gly Gly Ser Thr Arg Ala Gly Thr Val Arg Glu Thr Gln Gln Ile Val
 65                  70                  75                  80
```

| | |
|---|---|
| gcc gac acc acg ctg acc ccg gtg gcc cac ctc acc gcc gtc gac cac<br>Ala Asp Thr Thr Leu Thr Pro Val Ala His Leu Thr Ala Val Asp His<br>                            85                                    90                                    95 | 288 |
| tcc gtc gcc gag ctg cgc aac atc atc ggc cag tac gcc gac gcc ggg<br>Ser Val Ala Glu Leu Arg Asn Ile Ile Gly Gln Tyr Ala Asp Ala Gly<br>                         100                                 105                                110 | 336 |
| atc cgc aac atg ctg gcc gtg cgc ggc gac ccg ccc ggc gac ccg aac<br>Ile Arg Asn Met Leu Ala Val Arg Gly Asp Pro Pro Gly Asp Pro Asn<br>                     115                                 120                               125 | 384 |
| gcc gac tgg atc gcg cac ccc gag ggc ctg acc tac gcg gcc gaa ctg<br>Ala Asp Trp Ile Ala His Pro Glu Gly Leu Thr Tyr Ala Ala Glu Leu<br>130                                    135                                 140 | 432 |
| gtc agg ctc atc aag gag tcg ggc gac ttc tgc gtc ggc gtc gcg gcc<br>Val Arg Leu Ile Lys Glu Ser Gly Asp Phe Cys Val Gly Val Ala Ala<br>145                                    150                               155                         160 | 480 |
| ttc ccc gag atg cac ccg cgc tcc gcc gac tgg gac acg gac gtc acg<br>Phe Pro Glu Met His Pro Arg Ser Ala Asp Trp Asp Thr Asp Val Thr<br>                          165                                 170                               175 | 528 |
| aac ttc gtc gac aag tgc cgg gcc ggc gcc gac tac gcc atc acc cag<br>Asn Phe Val Asp Lys Cys Arg Ala Gly Ala Asp Tyr Ala Ile Thr Gln<br>                     180                                 185                               190 | 576 |
| atg ttc ttc cag ccc gac tcc tat ctc cgg ctg cgc gac cgg gtc gcc<br>Met Phe Phe Gln Pro Asp Ser Tyr Leu Arg Leu Arg Asp Arg Val Ala<br>                   195                                 200                              205 | 624 |
| gcg gcc ggc tgc gcg acc ccg gtc atc ccc gag gtc atg ccg gtg acc<br>Ala Ala Gly Cys Ala Thr Pro Val Ile Pro Glu Val Met Pro Val Thr<br>210                                    215                                 220 | 672 |
| agt gtg aag atg ctg gag agg ttg ccg aag ctc agc aac gcc tcg ttc<br>Ser Val Lys Met Leu Glu Arg Leu Pro Lys Leu Ser Asn Ala Ser Phe<br>225                                  230                               235                         240 | 720 |
| ccg gcg gag ttg aaa gag cgg atc ctc aca gcc aag gac gat ccg gcg<br>Pro Ala Glu Leu Lys Glu Arg Ile Leu Thr Ala Lys Asp Asp Pro Ala<br>                   245                                 250                              255 | 768 |
| gct gta cgc tcg atc ggc atc gag ttc gcc acg gag ttc tgc gcg cgg<br>Ala Val Arg Ser Ile Gly Ile Glu Phe Ala Thr Glu Phe Cys Ala Arg<br>                     260                                 265                               270 | 816 |
| ctg ctg gcc gag gga gtg cca gga ctg cac ttc atc acg ctc aac aac<br>Leu Leu Ala Glu Gly Val Pro Gly Leu His Phe Ile Thr Leu Asn Asn<br>275                                  280                               285 | 864 |
| tcc acg gcg acg ctg gaa atc tac gag aac ctg ggc ctg cac cac cca<br>Ser Thr Ala Thr Leu Glu Ile Tyr Glu Asn Leu Gly Leu His His Pro<br>290                                  295                               300 | 912 |
| ccg cgg gcc tag<br>Pro Arg Ala<br>305 | 924 |

<210> SEQ ID NO 6
<211> LENGTH: 307
<212> TYPE: PRT
<213> ORGANISM: Streptomyces coelicolor

<400> SEQUENCE: 6

Met Ala Leu Gly Thr Ala Ser Thr Arg Thr Asp Arg Ala Arg Thr Val
1               5                   10                  15

Arg Asp Ile Leu Ala Thr Gly Lys Thr Thr Tyr Ser Phe Glu Phe Ser
                20                  25                  30

Ala Pro Lys Thr Pro Lys Gly Glu Arg Asn Leu Trp Ser Ala Leu Arg
            35                  40                  45

Arg Val Glu Ala Val Ala Pro Asp Phe Val Ser Val Thr Tyr Gly Ala

```
                    50                  55                  60
Gly Gly Ser Thr Arg Ala Gly Thr Val Arg Glu Thr Gln Gln Ile Val
 65                  70                  75                  80

Ala Asp Thr Thr Leu Thr Pro Val Ala His Leu Thr Ala Val Asp His
                 85                  90                  95

Ser Val Ala Glu Leu Arg Asn Ile Ile Gly Gln Tyr Ala Asp Ala Gly
                100                 105                 110

Ile Arg Asn Met Leu Ala Val Arg Gly Asp Pro Gly Asp Pro Asn
            115                 120                 125

Ala Asp Trp Ile Ala His Pro Glu Gly Leu Thr Tyr Ala Ala Glu Leu
130                 135                 140

Val Arg Leu Ile Lys Glu Ser Gly Asp Phe Cys Val Gly Val Ala Ala
145                 150                 155                 160

Phe Pro Glu Met His Pro Arg Ser Ala Asp Trp Asp Thr Asp Val Thr
                165                 170                 175

Asn Phe Val Asp Lys Cys Arg Ala Gly Ala Asp Tyr Ala Ile Thr Gln
            180                 185                 190

Met Phe Phe Gln Pro Asp Ser Tyr Leu Arg Leu Arg Asp Arg Val Ala
            195                 200                 205

Ala Ala Gly Cys Ala Thr Pro Val Ile Pro Glu Val Met Pro Val Thr
210                 215                 220

Ser Val Lys Met Leu Glu Arg Leu Pro Lys Leu Ser Asn Ala Ser Phe
225                 230                 235                 240

Pro Ala Glu Leu Lys Glu Arg Ile Leu Thr Ala Lys Asp Asp Pro Ala
                245                 250                 255

Ala Val Arg Ser Ile Gly Ile Glu Phe Ala Thr Glu Phe Cys Ala Arg
            260                 265                 270

Leu Leu Ala Glu Gly Val Pro Gly Leu His Phe Ile Thr Leu Asn Asn
            275                 280                 285

Ser Thr Ala Thr Leu Glu Ile Tyr Glu Asn Leu Gly Leu His His Pro
    290                 295                 300

Pro Arg Ala
305

<210> SEQ ID NO 7
<211> LENGTH: 891
<212> TYPE: DNA
<213> ORGANISM: Aquifex aeolicus
<220> FEATURE:
<221> NAME/KEY: CDS
<222> LOCATION: (1)..(888)
<223> OTHER INFORMATION: RAA00346

<400> SEQUENCE: 7 atg aaa ata gga gat ata ctg agg aaa gga gtt ttc agt att tct ttt      48
Met Lys Ile Gly Asp Ile Leu Arg Lys Gly Val Phe Ser Ile Ser Phe
 1               5                  10                  15 gag ttc ttt cca ccg aag act gaa gag gga gaa aga cag ctc ttt gaa      96
Glu Phe Phe Pro Pro Lys Thr Glu Glu Gly Glu Arg Gln Leu Phe Glu
                20                  25                  30 act ata agg aaa ctt gag aaa tta aat cct act ttt gta tcc gtt act     144
Thr Ile Arg Lys Leu Glu Lys Leu Asn Pro Thr Phe Val Ser Val Thr
        35                  40                  45 tac ggg gca ggt ggt tcg act aga gat aga act agg aat ata gta cag     192
Tyr Gly Ala Gly Gly Ser Thr Arg Asp Arg Thr Arg Asn Ile Val Gln
    50                  55                  60 aaa ata cac gag gaa act aac ctc acc gtt atg gca cac ctc acc tgt     240
```

-continued

| | | |
|---|---|---|
| Lys Ile His Glu Glu Thr Asn Leu Thr Val Met Ala His Leu Thr Cys<br>65                              70                        75                        80 | | |
| ata gca cac acg aga gag gag ctt att gat atc ctt caa gat tac aaa<br>Ile Ala His Thr Arg Glu Glu Leu Ile Asp Ile Leu Gln Asp Tyr Lys<br>                    85                        90                        95 | 288 | |
| aac ata ggt ata gag aac att ctc gct ttg agg ggg gac gtt ccg agg<br>Asn Ile Gly Ile Glu Asn Ile Leu Ala Leu Arg Gly Asp Val Pro Arg<br>                  100                     105                     110 | 336 | |
| gac aaa ccg gac tgg aga ccg ccg aag ggt gcg tgc aag tat gca aaa<br>Asp Lys Pro Asp Trp Arg Pro Pro Lys Gly Ala Cys Lys Tyr Ala Lys<br>           115                     120                     125 | 384 | |
| gag ctc gta gaa ctg atc agg aag gag ttc gga gac tgg ttt tct atc<br>Glu Leu Val Glu Leu Ile Arg Lys Glu Phe Gly Asp Trp Phe Ser Ile<br>130                           135                     140 | 432 | |
| gga gtg gct tct tat cct gaa gga cat ccg gaa tca ccg aac ctc gag<br>Gly Val Ala Ser Tyr Pro Glu Gly His Pro Glu Ser Pro Asn Leu Glu<br>145                         150                     155                   160 | 480 | |
| tgg gaa gtg aag tac ttt aag gaa aag gta gag gca ggt gca gac ttc<br>Trp Glu Val Lys Tyr Phe Lys Glu Lys Val Glu Ala Gly Ala Asp Phe<br>                  165                     170                     175 | 528 | |
| tcg att act cag atg ttt ttc gtg aac gat tac tac tac agg ttt gtg<br>Ser Ile Thr Gln Met Phe Phe Val Asn Asp Tyr Tyr Tyr Arg Phe Val<br>           180                     185                     190 | 576 | |
| gaa atg tgc aaa aat gca ggg ata gat ata tct ata att ccg gga att<br>Glu Met Cys Lys Asn Ala Gly Ile Asp Ile Ser Ile Ile Pro Gly Ile<br>                  195                     200                     205 | 624 | |
| atg cct att act aac ttc aaa cag ata aga aag ttt gct tct ctt tgc<br>Met Pro Ile Thr Asn Phe Lys Gln Ile Arg Lys Phe Ala Ser Leu Cys<br>210                         215                     220 | 672 | |
| gga gcg acg att cca cag agt ctt ata gaa aag ctt gaa aaa gtg gag<br>Gly Ala Thr Ile Pro Gln Ser Leu Ile Glu Lys Leu Glu Lys Val Glu<br>225                         230                     235                   240 | 720 | |
| gat aaa ccg gaa gaa gta aaa aag ata ggg att gag ttt gcc ata aat<br>Asp Lys Pro Glu Glu Val Lys Lys Ile Gly Ile Glu Phe Ala Ile Asn<br>                  245                     250                     255 | 768 | |
| cag tgt ttg gat ctc ata gaa cac gga gtt ccg ggg ctt cac ttc tac<br>Gln Cys Leu Asp Leu Ile Glu His Gly Val Pro Gly Leu His Phe Tyr<br>           260                     265                     270 | 816 | |
| act ctg aac aag tcc gac gca act ttg aag ata tac gag gct ata aag<br>Thr Leu Asn Lys Ser Asp Ala Thr Leu Lys Ile Tyr Glu Ala Ile Lys<br>        275                     280                     285 | 864 | |
| gat aaa ata ccg gcc cgt tca act taa<br>Asp Lys Ile Pro Ala Arg Ser Thr<br>     290                     295 | 891 | |

<210> SEQ ID NO 8
<211> LENGTH: 296
<212> TYPE: PRT
<213> ORGANISM: Aquifex aeolicus

<400> SEQUENCE: 8

Met Lys Ile Gly Asp Ile Leu Arg Lys Gly Val Phe Ser Ile Ser Phe
1                  5                         10                      15

Glu Phe Phe Pro Pro Lys Thr Glu Glu Gly Glu Arg Gln Leu Phe Glu
                 20                     25                     30

Thr Ile Arg Lys Leu Glu Lys Leu Asn Pro Thr Phe Val Ser Val Thr
          35                     40                     45

Tyr Gly Ala Gly Gly Ser Thr Arg Asp Arg Thr Arg Asn Ile Val Gln
    50                     55                     60

-continued

```
Lys Ile His Glu Glu Thr Asn Leu Thr Val Met Ala His Leu Thr Cys
 65                  70                  75                  80

Ile Ala His Thr Arg Glu Leu Ile Asp Ile Leu Gln Asp Tyr Lys
             85                  90                  95

Asn Ile Gly Ile Glu Asn Ile Leu Ala Leu Arg Gly Asp Val Pro Arg
            100                 105                 110

Asp Lys Pro Asp Trp Arg Pro Lys Gly Ala Cys Lys Tyr Ala Lys
        115                 120                 125

Glu Leu Val Glu Leu Ile Arg Lys Glu Phe Gly Asp Trp Phe Ser Ile
    130                 135                 140

Gly Val Ala Ser Tyr Pro Glu Gly His Pro Glu Ser Pro Asn Leu Glu
145                 150                 155                 160

Trp Glu Val Lys Tyr Phe Lys Glu Lys Val Glu Ala Gly Ala Asp Phe
                165                 170                 175

Ser Ile Thr Gln Met Phe Phe Val Asn Asp Tyr Tyr Arg Phe Val
            180                 185                 190

Glu Met Cys Lys Asn Ala Gly Ile Asp Ile Ser Ile Ile Pro Gly Ile
        195                 200                 205

Met Pro Ile Thr Asn Phe Lys Gln Ile Arg Lys Phe Ala Ser Leu Cys
    210                 215                 220

Gly Ala Thr Ile Pro Gln Ser Leu Ile Glu Lys Leu Glu Lys Val Glu
225                 230                 235                 240

Asp Lys Pro Glu Glu Val Lys Lys Ile Gly Ile Glu Phe Ala Ile Asn
                245                 250                 255

Gln Cys Leu Asp Leu Ile Glu His Gly Val Pro Gly Leu His Phe Tyr
            260                 265                 270

Thr Leu Asn Lys Ser Asp Ala Thr Leu Lys Ile Tyr Glu Ala Ile Lys
        275                 280                 285

Asp Lys Ile Pro Ala Arg Ser Thr
    290                 295
```

<210> SEQ ID NO 9
<211> LENGTH: 831
<212> TYPE: DNA
<213> ORGANISM: Burkholderia cepacia
<220> FEATURE:
<221> NAME/KEY: CDS
<222> LOCATION: (1)..(828)
<223> OTHER INFORMATION: RBU14992

<400> SEQUENCE: 9

```
atg aac ccg atc gaa ctt tca ttc gaa ttc ttc ccg ccg aaa acg cag        48
Met Asn Pro Ile Glu Leu Ser Phe Glu Phe Phe Pro Pro Lys Thr Gln
  1               5                  10                  15 gaa ggc gtg gac aag ctg cgc gcc acg cgc gcc cag ctc gcc acg ctc        96
Glu Gly Val Asp Lys Leu Arg Ala Thr Arg Ala Gln Leu Ala Thr Leu
             20                  25                  30 aag ccc aag ttc gtg tcc gtc acg ttc ggc gcc ggc ggc tcg acg caa       144
Lys Pro Lys Phe Val Ser Val Thr Phe Gly Ala Gly Gly Ser Thr Gln
         35                  40                  45 cag ggc acg ctc gac acc gtc gtc gat atg gcg aag gaa ggg ctc gaa       192
Gln Gly Thr Leu Asp Thr Val Val Asp Met Ala Lys Glu Gly Leu Glu
     50                  55                  60 gcg gcg ccg cac gtg tcg tgc atc ggc tcg tcg aaa gag agc ctg cgc       240
Ala Ala Pro His Val Ser Cys Ile Gly Ser Ser Lys Glu Ser Leu Arg
 65                  70                  75                  80 gcc att ctc aac gag tac cgc gca cat ggc atc cgc cat atc gtc gcg       288
Ala Ile Leu Asn Glu Tyr Arg Ala His Gly Ile Arg His Ile Val Ala
                 85                  90                  95
```

-continued

```
                 85                  90                  95
ctg cgc ggc gat ctg ccg tcc ggc atg ggc gaa gtc ggc gag ctg cgc       336
Leu Arg Gly Asp Leu Pro Ser Gly Met Gly Glu Val Gly Glu Leu Arg
            100                 105                 110 tat gcg tcg gaa ctg gtg agc ttt atc cgc gcc gaa ttc ggc gac tgg       384
Tyr Ala Ser Glu Leu Val Ser Phe Ile Arg Ala Glu Phe Gly Asp Trp
        115                 120                 125 ttc tgc atc gag gtg gcc ggc tat ccg gaa tac cac ccg cag tcg cgc       432
Phe Cys Ile Glu Val Ala Gly Tyr Pro Glu Tyr His Pro Gln Ser Arg
    130                 135                 140 tcg ccg cgt cag gat ctg gaa aac ttc gcc cgc aag gtg aag gcc ggc       480
Ser Pro Arg Gln Asp Leu Glu Asn Phe Ala Arg Lys Val Lys Ala Gly
145                 150                 155                 160 gcc aat tcg gcg atc aca cag tac ttc ttc aat gca gac gcg tat ttc       528
Ala Asn Ser Ala Ile Thr Gln Tyr Phe Phe Asn Ala Asp Ala Tyr Phe
                165                 170                 175 cgt ttc gtc gac gac gcg aga aag ctc ggc gtg gac gtg ccg atc gtg       576
Arg Phe Val Asp Asp Ala Arg Lys Leu Gly Val Asp Val Pro Ile Val
            180                 185                 190 ccg ggc atc atg ccg atc acg aac ttc tcg cag ctg atg cgt ttc tcg       624
Pro Gly Ile Met Pro Ile Thr Asn Phe Ser Gln Leu Met Arg Phe Ser
        195                 200                 205 gag atg tgc ggc gct gaa gtg cca cgc tgg atc gcg cgc cgg ctg gaa       672
Glu Met Cys Gly Ala Glu Val Pro Arg Trp Ile Ala Arg Arg Leu Glu
    210                 215                 220 agc ttc ggc gac gat cgc gag tca att cgc gcg ttc ggg ctg gat gtg       720
Ser Phe Gly Asp Asp Arg Glu Ser Ile Arg Ala Phe Gly Leu Asp Val
225                 230                 235                 240 gtg acg gac ctg tgc agg cgt ctg atc gat gcg aag gtg ccg ggc ctg       768
Val Thr Asp Leu Cys Arg Arg Leu Ile Asp Ala Lys Val Pro Gly Leu
                245                 250                 255 cac ttc tac acg cta aac ggc gca gcg gcg acc aag gcg atc tgc gaa       816
His Phe Tyr Thr Leu Asn Gly Ala Ala Ala Thr Lys Ala Ile Cys Glu
            260                 265                 270 cgg ttg aac gtt taa                                                    831
Arg Leu Asn Val
        275
```

<210> SEQ ID NO 10
<211> LENGTH: 276
<212> TYPE: PRT
<213> ORGANISM: Burkholderia cepacia

<400> SEQUENCE: 10

```
Met Asn Pro Ile Glu Leu Ser Phe Glu Phe Pro Pro Lys Thr Gln
  1               5                  10                  15

Glu Gly Val Asp Lys Leu Arg Ala Thr Arg Ala Gln Leu Ala Thr Leu
                 20                  25                  30

Lys Pro Lys Phe Val Ser Val Thr Phe Gly Ala Gly Ser Thr Gln
            35                  40                  45

Gln Gly Thr Leu Asp Thr Val Asp Met Ala Lys Glu Gly Leu Glu
        50                  55                  60

Ala Ala Pro His Val Ser Cys Ile Gly Ser Ser Lys Glu Ser Leu Arg
 65                  70                  75                  80

Ala Ile Leu Asn Glu Tyr Arg Ala His Gly Ile Arg His Ile Val Ala
                 85                  90                  95

Leu Arg Gly Asp Leu Pro Ser Gly Met Gly Glu Val Gly Glu Leu Arg
            100                 105                 110
```

```
                                            -continued

Tyr Ala Ser Glu Leu Val Ser Phe Ile Arg Ala Glu Phe Gly Asp Trp
        115                 120                 125

Phe Cys Ile Glu Val Ala Gly Tyr Pro Glu Tyr His Pro Gln Ser Arg
    130                 135                 140

Ser Pro Arg Gln Asp Leu Glu Asn Phe Ala Arg Lys Val Lys Ala Gly
145                 150                 155                 160

Ala Asn Ser Ala Ile Thr Gln Tyr Phe Phe Asn Ala Asp Ala Tyr Phe
                165                 170                 175

Arg Phe Val Asp Asp Ala Arg Lys Leu Gly Val Asp Val Pro Ile Val
            180                 185                 190

Pro Gly Ile Met Pro Ile Thr Asn Phe Ser Gln Leu Met Arg Phe Ser
        195                 200                 205

Glu Met Cys Gly Ala Glu Val Pro Arg Trp Ile Ala Arg Arg Leu Glu
    210                 215                 220

Ser Phe Gly Asp Asp Arg Glu Ser Ile Arg Ala Phe Gly Leu Asp Val
225                 230                 235                 240

Val Thr Asp Leu Cys Arg Arg Leu Ile Asp Ala Lys Val Pro Gly Leu
                245                 250                 255

His Phe Tyr Thr Leu Asn Gly Ala Ala Thr Lys Ala Ile Cys Glu
            260                 265                 270

Arg Leu Asn Val
        275

<210> SEQ ID NO 11
<211> LENGTH: 846
<212> TYPE: DNA
<213> ORGANISM: Nitrosomonas europaea
<220> FEATURE:
<221> NAME/KEY: CDS
<222> LOCATION: (1)..(843)
<223> OTHER INFORMATION: RNE02657

<400> SEQUENCE: 11 atg caa tcc cag aaa aaa ttt acc ccc aca ttc agt ttt gaa ttt ttc      48
Met Gln Ser Gln Lys Lys Phe Thr Pro Thr Phe Ser Phe Glu Phe Phe
  1               5                  10                  15 ccg ccg cag aca ccg gaa ggc atg gaa aag ctg cgg gca acg cgc ata      96
Pro Pro Gln Thr Pro Glu Gly Met Glu Lys Leu Arg Ala Thr Arg Ile
             20                  25                  30 cag ctt gct cag ttc aat ccg aag ttt ttt tcg gtg acg ttt ggt gcc     144
Gln Leu Ala Gln Phe Asn Pro Lys Phe Phe Ser Val Thr Phe Gly Ala
         35                  40                  45 ggc gga tcc act cgt gaa cgc acg ctc gaa acc gtg ctg gaa att cag     192
Gly Gly Ser Thr Arg Glu Arg Thr Leu Glu Thr Val Leu Glu Ile Gln
     50                  55                  60 gca gaa ggc tat ccg gta gcg ccc cat ctt tcc tgt atc ggc tcc acg     240
Ala Glu Gly Tyr Pro Val Ala Pro His Leu Ser Cys Ile Gly Ser Thr
 65                  70                  75                  80 cgt gac aat atc cgt tcg atc ctt gag aaa tat cac agt cac ggt atc     288
Arg Asp Asn Ile Arg Ser Ile Leu Glu Lys Tyr His Ser His Gly Ile
                 85                  90                  95 agc cgc att gtg gcg cta cgt ggt gat tta ccc tcc ggc atg gcg cag     336
Ser Arg Ile Val Ala Leu Arg Gly Asp Leu Pro Ser Gly Met Ala Gln
            100                 105                 110 gcg gga gaa ttc cgc tac gcc aac gag ctg gta gca ttt atc cgc aag     384
Ala Gly Glu Phe Arg Tyr Ala Asn Glu Leu Val Ala Phe Ile Arg Lys
        115                 120                 125 gag ttc ggt gat acc ttc tgg atc gaa gtg gcg gct tat ccg gaa tat     432
Glu Phe Gly Asp Thr Phe Trp Ile Glu Val Ala Ala Tyr Pro Glu Tyr
    130                 135                 140
```

```
                    130                  135                  140
cat cca caa gcc cgc tcc gct ctg gag gat ttc acc aat ttc aga cga        480
His Pro Gln Ala Arg Ser Ala Leu Glu Asp Phe Thr Asn Phe Arg Arg
145                 150                 155                 160 aaa gtc gaa gca ggt tcc aat gca gcg att acc cag ttt ttc tat aac        528
Lys Val Glu Ala Gly Ser Asn Ala Ala Ile Thr Gln Phe Phe Tyr Asn
                165                 170                 175 gtg gat gcc tat ctg cat ttc gta gag atg tgt gaa gct gcg gat ctg        576
Val Asp Ala Tyr Leu His Phe Val Glu Met Cys Glu Ala Ala Asp Leu
            180                 185                 190 aat atc ccg atc gtt ccc ggc atc atg ccg atc agc aaa ttt tct caa        624
Asn Ile Pro Ile Val Pro Gly Ile Met Pro Ile Ser Lys Phe Ser Gln
        195                 200                 205 ctg gca aga ttt tcg gat ggc tgt gga gca gaa att cca cgc tgg att        672
Leu Ala Arg Phe Ser Asp Gly Cys Gly Ala Glu Ile Pro Arg Trp Ile
    210                 215                 220 cgc aga aaa ctg gaa agc ttc ggt gat gat att ccg tct atc cag gca        720
Arg Arg Lys Leu Glu Ser Phe Gly Asp Asp Ile Pro Ser Ile Gln Ala
225                 230                 235                 240 ttc ggg ctg gat gtc gtc aca gcg tta tgt gct cgt ctg ctg gaa gcc        768
Phe Gly Leu Asp Val Val Thr Ala Leu Cys Ala Arg Leu Leu Glu Ala
                245                 250                 255 ggc gca ccc ggc ctg cat ttc tac aca ctc aac tcc gcc gta cta ccc        816
Gly Ala Pro Gly Leu His Phe Tyr Thr Leu Asn Ser Ala Val Leu Pro
            260                 265                 270 aca aaa atc tgg caa cgc ctg ggg tta tag                                846
Thr Lys Ile Trp Gln Arg Leu Gly Leu
        275                 280

<210> SEQ ID NO 12
<211> LENGTH: 281
<212> TYPE: PRT
<213> ORGANISM: Nitrosomonas europaea

<400> SEQUENCE: 12

Met Gln Ser Gln Lys Lys Phe Thr Pro Thr Phe Ser Phe Glu Phe Phe
1               5                   10                  15

Pro Pro Gln Thr Pro Glu Gly Met Glu Lys Leu Arg Ala Thr Arg Ile
            20                  25                  30

Gln Leu Ala Gln Phe Asn Pro Lys Phe Ser Val Thr Phe Gly Ala
        35                  40                  45

Gly Gly Ser Thr Arg Glu Arg Thr Leu Glu Thr Val Leu Glu Ile Gln
    50                  55                  60

Ala Glu Gly Tyr Pro Val Ala Pro His Leu Ser Cys Ile Gly Ser Thr
65                  70                  75                  80

Arg Asp Asn Ile Arg Ser Ile Leu Glu Lys Tyr His Ser His Gly Ile
                85                  90                  95

Ser Arg Ile Val Ala Leu Arg Gly Asp Leu Pro Ser Gly Met Ala Gln
            100                 105                 110

Ala Gly Glu Phe Arg Tyr Ala Asn Glu Leu Val Ala Phe Ile Arg Lys
        115                 120                 125

Glu Phe Gly Asp Thr Phe Trp Ile Glu Val Ala Ala Tyr Pro Glu Tyr
    130                 135                 140

His Pro Gln Ala Arg Ser Ala Leu Glu Asp Phe Thr Asn Phe Arg Arg
145                 150                 155                 160

Lys Val Glu Ala Gly Ser Asn Ala Ala Ile Thr Gln Phe Phe Tyr Asn
                165                 170                 175
```

-continued

```
Val Asp Ala Tyr Leu His Phe Val Glu Met Cys Glu Ala Ala Asp Leu
            180                 185                 190
Asn Ile Pro Ile Val Pro Gly Ile Met Pro Ile Ser Lys Phe Ser Gln
        195                 200                 205
Leu Ala Arg Phe Ser Asp Gly Cys Gly Ala Glu Ile Pro Arg Trp Ile
    210                 215                 220
Arg Arg Lys Leu Glu Ser Phe Gly Asp Asp Ile Pro Ser Ile Gln Ala
225                 230                 235                 240
Phe Gly Leu Asp Val Val Thr Ala Leu Cys Ala Arg Leu Leu Glu Ala
                245                 250                 255
Gly Ala Pro Gly Leu His Phe Tyr Thr Leu Asn Ser Ala Val Leu Pro
            260                 265                 270
Thr Lys Ile Trp Gln Arg Leu Gly Leu
        275                 280
```

<210> SEQ ID NO 13
<211> LENGTH: 873
<212> TYPE: DNA
<213> ORGANISM: Pseudomonas aeruginosa
<220> FEATURE:
<221> NAME/KEY: CDS
<222> LOCATION: (1)..(870)
<223> OTHER INFORMATION: RPA03308

<400> SEQUENCE: 13

```
gtg gtc gcg tcc aag gaa ccg atc atg agt cag agc gaa cgc cgt ttc      48
Val Val Ala Ser Lys Glu Pro Ile Met Ser Gln Ser Glu Arg Arg Phe
  1               5                  10                  15 agc ttc gag ttc ttc ccg gcg aag acc gag gcc ggc cat gaa aag ctg      96
Ser Phe Glu Phe Phe Pro Ala Lys Thr Glu Ala Gly His Glu Lys Leu
             20                  25                  30 ttg gcc acc gcc cgc aac ctg gcg ggc tac aag ccc gac ttc ttc tcc     144
Leu Ala Thr Ala Arg Asn Leu Ala Gly Tyr Lys Pro Asp Phe Phe Ser
         35                  40                  45 tgc acc tac ggc gcc ggc gga tcc acc cgc gac cgc acg ttg agt acc     192
Cys Thr Tyr Gly Ala Gly Gly Ser Thr Arg Asp Arg Thr Leu Ser Thr
     50                  55                  60 gtg ctg caa ctg gac ggc gag gtg aag gtg ccg acc gcg ccg cac ctg     240
Val Leu Gln Leu Asp Gly Glu Val Lys Val Pro Thr Ala Pro His Leu
 65                  70                  75                  80 tcc tgt gtc ggc gac tcg aaa gcc gag ttg cgc gaa ctg ctc ggc cgc     288
Ser Cys Val Gly Asp Ser Lys Ala Glu Leu Arg Glu Leu Leu Gly Arg
                 85                  90                  95 tac cgc gag gcc ggc atc cgc cgc atc gtc gcc ctg cgc ggc gac ctg     336
Tyr Arg Glu Ala Gly Ile Arg Arg Ile Val Ala Leu Arg Gly Asp Leu
            100                 105                 110 ccg tcg ggc atg ggc atg gcc agc ggc gaa ctg cgc tac gcc aac gaa     384
Pro Ser Gly Met Gly Met Ala Ser Gly Glu Leu Arg Tyr Ala Asn Glu
        115                 120                 125 ctg gtg gac ttc atc cgc acc gag acc ggc gac cac ttc cac atc gag     432
Leu Val Asp Phe Ile Arg Thr Glu Thr Gly Asp His Phe His Ile Glu
    130                 135                 140 gtc gcc gcc tat ccg gag gtc cac ccc cag gcg cgc agc ttc gag gat     480
Val Ala Ala Tyr Pro Glu Val His Pro Gln Ala Arg Ser Phe Glu Asp
145                 150                 155                 160 gac ctg gcg aac ttc gtg cgc aag gtg aag gcc ggc gcc agc agc gcc     528
Asp Leu Ala Asn Phe Val Arg Lys Val Lys Ala Gly Ala Ser Ser Ala
                165                 170                 175 atc acc cag tac ttc ttc aac gcc gat gcc tat ttc tac ttc gtc gag     576
Ile Thr Gln Tyr Phe Phe Asn Ala Asp Ala Tyr Phe Tyr Phe Val Glu
```

-continued

```
            180                 185                 190
cgg gtc gcc aag ctc ggc gtg gac atc ccg gtg gtc ccc ggc atc atg       624
Arg Val Ala Lys Leu Gly Val Asp Ile Pro Val Val Pro Gly Ile Met
            195                 200                 205 ccg atc acc aac tac tcc aag ctg gcg cgc ttc tcc gac gcc tgc ggc       672
Pro Ile Thr Asn Tyr Ser Lys Leu Ala Arg Phe Ser Asp Ala Cys Gly
    210                 215                 220 gcc gaa ctg ccg cgc tgg atc cgc aag caa ctg gaa gcc tac ggc gac       720
Ala Glu Leu Pro Arg Trp Ile Arg Lys Gln Leu Glu Ala Tyr Gly Asp
225                 230                 235                 240 gac agc cgc agc atc cag gcc ttc ggc gag cag gtc atc agc gag atg       768
Asp Ser Arg Ser Ile Gln Ala Phe Gly Glu Gln Val Ile Ser Glu Met
                245                 250                 255 tgc gaa cgc ctg ctg gag ggc ggc gca ccg gga ctg cat ttc tat act       816
Cys Glu Arg Leu Leu Glu Gly Gly Ala Pro Gly Leu His Phe Tyr Thr
            260                 265                 270 ttg aac cag gcc gat ccg agc ctg gcg atc tgg aag aat ctc cag ctg       864
Leu Asn Gln Ala Asp Pro Ser Leu Ala Ile Trp Lys Asn Leu Gln Leu
        275                 280                 285 cca cgc tga                                                            873
Pro Arg
    290

<210> SEQ ID NO 14
<211> LENGTH: 290
<212> TYPE: PRT
<213> ORGANISM: Pseudomonas aeruginosa

<400> SEQUENCE: 14

Val Val Ala Ser Lys Glu Pro Ile Met Ser Gln Ser Glu Arg Arg Phe
 1               5                  10                  15

Ser Phe Glu Phe Phe Pro Ala Lys Thr Glu Ala Gly His Glu Lys Leu
                20                  25                  30

Leu Ala Thr Ala Arg Asn Leu Ala Gly Tyr Lys Pro Asp Phe Phe Ser
            35                  40                  45

Cys Thr Tyr Gly Ala Gly Gly Ser Thr Arg Asp Arg Thr Leu Ser Thr
        50                  55                  60

Val Leu Gln Leu Asp Gly Glu Val Lys Val Pro Thr Ala Pro His Leu
65                  70                  75                  80

Ser Cys Val Gly Asp Ser Lys Ala Glu Leu Arg Glu Leu Leu Gly Arg
                85                  90                  95

Tyr Arg Glu Ala Gly Ile Arg Arg Ile Val Ala Leu Arg Gly Asp Leu
            100                 105                 110

Pro Ser Gly Met Gly Met Ala Ser Gly Glu Leu Arg Tyr Ala Asn Glu
        115                 120                 125

Leu Val Asp Phe Ile Arg Thr Glu Thr Gly Asp His Phe His Ile Glu
    130                 135                 140

Val Ala Ala Tyr Pro Glu Val His Pro Gln Ala Arg Ser Phe Glu Asp
145                 150                 155                 160

Asp Leu Ala Asn Phe Val Arg Lys Val Lys Ala Gly Ala Ser Ser Ala
                165                 170                 175

Ile Thr Gln Tyr Phe Phe Asn Ala Asp Ala Tyr Phe Tyr Phe Val Glu
            180                 185                 190

Arg Val Ala Lys Leu Gly Val Asp Ile Pro Val Val Pro Gly Ile Met
        195                 200                 205

Pro Ile Thr Asn Tyr Ser Lys Leu Ala Arg Phe Ser Asp Ala Cys Gly
    210                 215                 220
```

```
Ala Glu Leu Pro Arg Trp Ile Arg Lys Gln Leu Glu Ala Tyr Gly Asp
225                 230                 235                 240

Asp Ser Arg Ser Ile Gln Ala Phe Gly Glu Gln Val Ile Ser Glu Met
                245                 250                 255

Cys Glu Arg Leu Leu Glu Gly Gly Ala Pro Gly Leu His Phe Tyr Thr
            260                 265                 270

Leu Asn Gln Ala Asp Pro Ser Leu Ala Ile Trp Lys Asn Leu Gln Leu
        275                 280                 285

Pro Arg
    290

<210> SEQ ID NO 15
<211> LENGTH: 828
<212> TYPE: DNA
<213> ORGANISM: Xylella almond
<220> FEATURE:
<221> NAME/KEY: CDS
<222> LOCATION: (1)..(825)
<223> OTHER INFORMATION: RXFX00359

<400> SEQUENCE: 15 atg att cca atc agc ttc gag ttt tat cca ccc aaa aac gac gat caa      48
Met Ile Pro Ile Ser Phe Glu Phe Tyr Pro Pro Lys Asn Asp Asp Gln
1               5                   10                  15 cgc gca cag ttg gac agg aca gca aac cgg cta cgc gca ttc gca cca      96
Arg Ala Gln Leu Asp Arg Thr Ala Asn Arg Leu Arg Ala Phe Ala Pro
            20                  25                  30 gaa tac gtc tcc tgc acc ttc ggc gcc ggt ggc tcc aca ctc agt tac     144
Glu Tyr Val Ser Cys Thr Phe Gly Ala Gly Gly Ser Thr Leu Ser Tyr
        35                  40                  45 acc tca gaa aca gtg cgc cat ctc agc caa cac cac ggc ttt gac gcc     192
Thr Ser Glu Thr Val Arg His Leu Ser Gln His His Gly Phe Asp Ala
    50                  55                  60 gca ccg cat ctg tcc tgt gtg ggc ggc agt cgc caa gaa atc cgc gaa     240
Ala Pro His Leu Ser Cys Val Gly Gly Ser Arg Gln Glu Ile Arg Glu
65                  70                  75                  80 ctt ctc aaa ctg tac cgc gcg att ggc tgc caa cgc atc gtg gcg cta     288
Leu Leu Lys Leu Tyr Arg Ala Ile Gly Cys Gln Arg Ile Val Ala Leu
                85                  90                  95 cgc ggc gat ctc ccc tcg ggc atg ggc cac ccc ggc gac ctc cgc tac     336
Arg Gly Asp Leu Pro Ser Gly Met Gly His Pro Gly Asp Leu Arg Tyr
            100                 105                 110 gca gct gac ctg att acc ttc atc cgt acc gag cat ggc gat cac ttc     384
Ala Ala Asp Leu Ile Thr Phe Ile Arg Thr Glu His Gly Asp His Phe
        115                 120                 125 cac cta gag atc ggc gca tac ccg gaa acc cac cca caa gcc agc aac     432
His Leu Glu Ile Gly Ala Tyr Pro Glu Thr His Pro Gln Ala Ser Asn
    130                 135                 140 aca ctg aac gac ctt cac tat ttc aaa gcc aaa gcc gat gca ggc gcc     480
Thr Leu Asn Asp Leu His Tyr Phe Lys Ala Lys Ala Asp Ala Gly Ala
145                 150                 155                 160 gat gcg gca atc act caa tac ttt tat aac cca gac gcc tat ttc cac     528
Asp Ala Ala Ile Thr Gln Tyr Phe Tyr Asn Pro Asp Ala Tyr Phe His
                165                 170                 175 ttc gtc gac gca gtg cag cgc ctg ggc gtc acc atc ccc att gtt gcc     576
Phe Val Asp Ala Val Gln Arg Leu Gly Val Thr Ile Pro Ile Val Ala
            180                 185                 190 gga gtc atg ccc atc tcc aac ttt gac cag ttg cgc cat ttc tcc gaa     624
Gly Val Met Pro Ile Ser Asn Phe Asp Gln Leu Arg His Phe Ser Glu
        195                 200                 205
```

```
caa tgc ggc gcc gaa ata ccc cgc tgg att aca aaa aaa atg cag gct    672
Gln Cys Gly Ala Glu Ile Pro Arg Trp Ile Thr Lys Lys Met Gln Ala
    210                 215                 220 tac ggc gac gac acc aaa tcg ata cgc gcg ttc ggt gcc gac gtc gtg    720
Tyr Gly Asp Asp Thr Lys Ser Ile Arg Ala Phe Gly Ala Asp Val Val
225                 230                 235                 240 acc gca tta tgt gag cgg cta atc gct ggc ggc gca ccg ggg ctg cac    768
Thr Ala Leu Cys Glu Arg Leu Ile Ala Gly Gly Ala Pro Gly Leu His
                245                 250                 255 ttc tac acg ctc aac cta gcc aaa cca agc acc caa gtg ctg caa cgc    816
Phe Tyr Thr Leu Asn Leu Ala Lys Pro Ser Thr Gln Val Leu Gln Arg
            260                 265                 270 tta ggc tat tga                                                    828
Leu Gly Tyr
        275

<210> SEQ ID NO 16
<211> LENGTH: 275
<212> TYPE: PRT
<213> ORGANISM: Xylella almond

<400> SEQUENCE: 16

Met Ile Pro Ile Ser Phe Glu Phe Tyr Pro Pro Lys Asn Asp Asp Gln
1               5                   10                  15

Arg Ala Gln Leu Asp Arg Thr Ala Asn Arg Leu Arg Ala Phe Ala Pro
            20                  25                  30

Glu Tyr Val Ser Cys Thr Phe Gly Ala Gly Ser Thr Leu Ser T

Leu Gly Tyr
        275

<210> SEQ ID NO 17
<211> LENGTH: 828
<212> TYPE: DNA
<213> ORGANISM: Xylella oleander
<220> FEATURE:
<221> NAME/KEY: CDS
<222> LOCATION: (1)..(825)
<223> OTHER INFORMATION: RXFY01676

```
ttc tac acg ctc aac cta gcc aaa cca agc acc caa gtg ctg caa cgc         816
Phe Tyr Thr Leu Asn Leu Ala Lys Pro Ser Thr Gln Val Leu Gln Arg
        260                 265                 270 tta ggc tat tga                                                          828
Leu Gly Tyr
        275

<210> SEQ ID NO 18
<211> LENGTH: 275
<212> TYPE: PRT
<213> ORGANISM: Xylella oleander

<400

<223> OTHER INFORMATION: RPU04845

<400> SEQUENCE: 19

```
atg tcc caa gac cgt cgc tac agc ttc gag ttc ttc ccg acc aag acc    48
Met Ser Gln Asp Arg Arg Tyr Ser Phe Glu Phe Phe Pro Thr Lys Thr
1               5                   10                  15 gat gct ggg cat gaa aaa ctg ctc gcc act gcc cgt cag ctg gcc acc    96
Asp Ala Gly His Glu Lys Leu Leu Ala Thr Ala Arg Gln Leu Ala Thr
            20                  25                  30 tat aag cct gac ttc ttt tcc tgc acc tac ggc gct ggc ggt tcg acc   144
Tyr Lys Pro Asp Phe Phe Ser Cys Thr Tyr Gly Ala Gly Gly Ser Thr
        35                  40                  45 cgt gac cgc acg ctg aac acc gtt ctg cag ctg gaa agc gaa gtc aaa   192
Arg Asp Arg Thr Leu Asn Thr Val Leu Gln Leu Glu Ser Glu Val Lys
50                  55                  60 atc ccc gcc gca ccg cac ctg tcg tgc gtc ggc gac agc aag gac gac   240
Ile Pro Ala Ala Pro His Leu Ser Cys Val Gly Asp Ser Lys Asp Asp
65                  70                  75                  80 ctg cgc ggc ctg ctg aac gag tac aag gcc gcc ggc atc aag cgc atc   288
Leu Arg Gly Leu Leu Asn Glu Tyr Lys Ala Ala Gly Ile Lys Arg Ile
                85                  90                  95 gtc gcc ctg cgc ggt gac ctg ccg tcc ggc atg ggc atg acc agc ggc   336
Val Ala Leu Arg Gly Asp Leu Pro Ser Gly Met Gly Met Thr Ser Gly
            100                 105                 110 gag ctg cgt cac gcc aat gaa ctg gtt gaa ttc att cgt gaa gaa acc   384
Glu Leu Arg His Ala Asn Glu Leu Val Glu Phe Ile Arg Glu Glu Thr
        115                 120                 125 ggc aat cat ttc cac atc gaa gtc gcc gcc tac ccg gag atg cat ccg   432
Gly Asn His Phe His Ile Glu Val Ala Ala Tyr Pro Glu Met His Pro
    130                 135                 140 caa gcg cgc aac tac gaa gac gat ctc gcc aac ttc gtg cgc aag gcc   480
Gln Ala Arg Asn Tyr Glu Asp Asp Leu Ala Asn Phe Val Arg Lys Ala
145                 150                 155                 160 cgt gcc ggc gcc gac agc gcg atc acc cag tac ttc ttc aac gcc gac   528
Arg Ala Gly Ala Asp Ser Ala Ile Thr Gln Tyr Phe Phe Asn Ala Asp
                165                 170                 175 agc tac ttc tac ttc gtc gac cgt ttg cag gcg ctg ggc gtg gac att   576
Ser Tyr Phe Tyr Phe Val Asp Arg Leu Gln Ala Leu Gly Val Asp Ile
            180                 185                 190 ccg gtg gta ccg ggg atc atg ccg atc acc aac tac agc aaa ctc gcg   624
Pro Val Val Pro Gly Ile Met Pro Ile Thr Asn Tyr Ser Lys Leu Ala
        195                 200                 205 cgc ttc tcc gat gcc tgc ggt gcg gaa atc ccg cgc tgg atc cgc aag   672
Arg Phe Ser Asp Ala Cys Gly Ala Glu Ile Pro Arg Trp Ile Arg Lys
    210                 215                 220 cag ctg gaa gcc tac ggc gat gac agc caa agc att cag cgc ttt ggc   720
Gln Leu Glu Ala Tyr Gly Asp Asp Ser Gln Ser Ile Gln Arg Phe Gly
225                 230                 235                 240 gaa caa gtc gtc acg gaa atg tgc gaa cgc ctg ctg caa ggc ggc gcg   768
Glu Gln Val Val Thr Glu Met Cys Glu Arg Leu Leu Gln Gly Gly Ala
                245                 250                 255 ccc ggc ctg cac ttc tat tcc atg aac cag gcc gaa cca agc ctg gcg   816
Pro Gly Leu His Phe Tyr Ser Met Asn Gln Ala Glu Pro Ser Leu Ala
            260                 265                 270 atc tgg aac aac ctg aag ctg ccg cgc taa                           846
Ile Trp Asn Asn Leu Lys Leu Pro Arg
        275                 280
```

<210> SEQ ID NO 20
<211> LENGTH: 281

```
<212> TYPE: PRT
<213> ORGANISM: Pseodomonas fluorescens

<400> SEQUENCE: 20

Met Ser Gln Asp Arg Arg Tyr Ser Phe Glu Phe Pro Thr Lys Thr
 1               5                  10                  15

Asp Ala Gly His Glu Lys Leu Leu Ala Thr Ala Arg Gln Leu Ala Thr
                20                  25                  30

Tyr Lys Pro Asp Phe Phe Ser Cys Thr Tyr Gly Ala Gly Ser Thr
                35                  40                  45

Arg Asp Arg Thr Leu Asn Thr Val Leu Gln Leu Glu Ser Glu Val Lys
 50                  55                  60

Ile Pro Ala Ala Pro His Leu Ser Cys Val Gly Asp Ser Lys Asp Asp
 65                  70                  75                  80

Leu Arg Gly Leu Leu Asn Glu Tyr Lys Ala Ala Gly Ile Lys Arg Ile
                85                  90                  95

Val Ala Leu Arg Gly Asp Leu Pro Ser Gly Met Gly Met Thr Ser Gly
                100                 105                 110

Glu Leu Arg His Ala Asn Glu Leu Val Glu Phe Ile Arg Glu Glu Thr
                115                 120                 125

Gly Asn His Phe His Ile Glu Val Ala Ala Tyr Pro Glu Met His Pro
130                 135                 140

Gln Ala Arg Asn Tyr Glu Asp Asp Leu Ala Asn Phe Val Arg Lys Ala
145                 150                 155                 160

Arg Ala Gly Ala Asp Ser Ala Ile Thr Gln Tyr Phe Phe Asn Ala Asp
                165                 170                 175

Ser Tyr Phe Tyr Phe Val Asp Arg Leu Gln Ala Leu Gly Val Asp Ile
                180                 185                 190

Pro Val Val Pro Gly Ile Met Pro Ile Thr Asn Tyr Ser Lys Leu Ala
                195                 200                 205

Arg Phe Ser Asp Ala Cys Gly Ala Glu Ile Pro Arg Trp Ile Arg Lys
                210                 215                 220

Gln Leu Glu Ala Tyr Gly Asp Asp Ser Gln Ser Ile Gln Arg Phe Gly
225                 230                 235                 240

Glu Gln Val Val Thr Glu Met Cys Glu Arg Leu Leu Gln Gly Gly Ala
                245                 250                 255

Pro Gly Leu His Phe Tyr Ser Met Asn Gln Ala Glu Pro Ser Leu Ala
                260                 265                 270

Ile Trp Asn Asn Leu Lys Leu Pro Arg
                275                 280

<210> SEQ ID NO 21
<211> LENGTH: 1812
<212> TYPE: DNA
<213> ORGANISM: Schizosaccharomyces pombe
<220> FEATURE:
<221> NAME/KEY: CDS
<222> LOCATION: (1)..(1809)
<223> OTHER INFORMATION: RSO01645

<400> SEQUENCE: 21 atg aaa ata agt gac aaa tta ctt cac ccg gat tgg aag gaa aaa gtt      48
Met Lys Ile Ser Asp Lys Leu Leu His Pro Asp Trp Lys Glu Lys Val
 1               5                  10                  15 act tac agt tat gaa ttt ttt cct cca aaa acg agc act ggt gtc caa     96
Thr Tyr Ser Tyr Glu Phe Phe Pro Pro Lys Thr Ser Thr Gly Val Gln
                20                  25                  30
```

```
aat ctt tac aat cgt ata gat cgc atg aag act tgg ggt cgt ccc atg       144
Asn Leu Tyr Asn Arg Ile Asp Arg Met Lys Thr Trp Gly Arg Pro Met
         35                  40                  45 ttt gtc gat gtg act tgg ggt gct ggt ggt act tct tca gaa ctg act       192
Phe Val Asp Val Thr Trp Gly Ala Gly Gly Thr Ser Ser Glu Leu Thr
 50                  55                  60 cct gga atc gtt aat gta att caa aca gat ttt gaa gtg gat act tgc       240
Pro Gly Ile Val Asn Val Ile Gln Thr Asp Phe Glu Val Asp Thr Cys
 65                  70                  75                  80 atg cat ttg act tgt acg aac atg tcc aca gaa atg att gac gca gct       288
Met His Leu Thr Cys Thr Asn Met Ser Thr Glu Met Ile Asp Ala Ala
                 85                  90                  95 ttg aaa cgg gct cat gaa aca ggg tgt cgt aac ata ttg gcc ctt aga       336
Leu Lys Arg Ala His Glu Thr Gly Cys Arg Asn Ile Leu Ala Leu Arg
             100                 105                 110 ggt gat cct gtt aaa gat aca gac tgg act gaa ggc gaa agt gga ttc       384
Gly Asp Pro Val Lys Asp Thr Asp Trp Thr Glu Gly Glu Ser Gly Phe
         115                 120                 125 cgg tat gct tca gac tta gtt aga tat att cgc aca cat tat aat gat       432
Arg Tyr Ala Ser Asp Leu Val Arg Tyr Ile Arg Thr His Tyr Asn Asp
 130                 135                 140 gaa ttc tgt att ggt gta gct ggc tat cca gaa gga tat tca cca gat       480
Glu Phe Cys Ile Gly Val Ala Gly Tyr Pro Glu Gly Tyr Ser Pro Asp
145                 150                 155                 160 gat gac att gat gaa agc ata aag cat ctg aaa tta aaa gtc gat gaa       528
Asp Asp Ile Asp Glu Ser Ile Lys His Leu Lys Leu Lys Val Asp Glu
                 165                 170                 175 ggt gct gat ttt atc gtt act caa atg ttt tat gat gta gac aat ttt       576
Gly Ala Asp Phe Ile Val Thr Gln Met Phe Tyr Asp Val Asp Asn Phe
             180                 185                 190 atc gca tgg gtc gat aaa gtg cgt gca gca gga ata aat atc cct ata       624
Ile Ala Trp Val Asp Lys Val Arg Ala Ala Gly Ile Asn Ile Pro Ile
         195                 200                 205 ttt ccg ggc att atg cct att cag gca tgg gat tcc ttt att cgg aga       672
Phe Pro Gly Ile Met Pro Ile Gln Ala Trp Asp Ser Phe Ile Arg Arg
 210                 215                 220 gcg aaa tgg agc ggt gtt aaa att ccc cag cat ttt atg gat act cta       720
Ala Lys Trp Ser Gly Val Lys Ile Pro Gln His Phe Met Asp Thr Leu
225                 230                 235                 240 gtc cca gtt aaa gac gat gat gaa gga gtc cgt gag cgt ggt gtt gag       768
Val Pro Val Lys Asp Asp Asp Glu Gly Val Arg Glu Arg Gly Val Glu
                 245                 250                 255 ctc ata gtc gaa atg tgc cgt aag ctt ata gct agt ggc att acg aga       816
Leu Ile Val Glu Met Cys Arg Lys Leu Ile Ala Ser Gly Ile Thr Arg
             260                 265                 270 ctt cat ttt tac act atg aat tta gaa aag gcc gtt aaa atg att att       864
Leu His Phe Tyr Thr Met Asn Leu Glu Lys Ala Val Lys Met Ile Ile
         275                 280                 285 gaa cga tta ggt tta tta gat gaa aac ttg gct cct ata gtg gat act       912
Glu Arg Leu Gly Leu Leu Asp Glu Asn Leu Ala Pro Ile Val Asp Thr
 290                 295                 300 aat aac gtc gag tta acc aat gct tcc agt caa gat cgt cgg ata aat       960
Asn Asn Val Glu Leu Thr Asn Ala Ser Ser Gln Asp Arg Arg Ile Asn
305                 310                 315                 320 gaa ggt gta cgg ccc att ttc tgg cgc act cgt aat gaa agt tat gtc      1008
Glu Gly Val Arg Pro Ile Phe Trp Arg Thr Arg Asn Glu Ser Tyr Val
                 325                 330                 335 tcg cgt act gat cag tgg gac gaa tta ccg cat ggt cgt tgg ggt gac      1056
Ser Arg Thr Asp Gln Trp Asp Glu Leu Pro His Gly Arg Trp Gly Asp
             340                 345                 350
```

```
tct cgt agc cct gct ttt ggc gaa ttt gat gct att aga tat ggt ctt      1104
Ser Arg Ser Pro Ala Phe Gly Glu Phe Asp Ala Ile Arg Tyr Gly Leu
        355                 360                 365 cgt atg tct ccc aag gag atc aca aca tcg tgg ggg tct cct aaa tct      1152
Arg Met Ser Pro Lys Glu Ile Thr Thr Ser Trp Gly Ser Pro Lys Ser
370                 375                 380 tac tcg gaa atc ggc gat ttg ttt gcc agg tac tgt gaa aaa aag att      1200
Tyr Ser Glu Ile Gly Asp Leu Phe Ala Arg Tyr Cys Glu Lys Lys Ile
385                 390                 395                 400 agc tcc ctc cct tgg agt gat ctt ccc ata tcc gat gaa gcc gac ttg      1248
Ser Ser Leu Pro Trp Ser Asp Leu Pro Ile Ser Asp Glu Ala Asp Leu
            405                 410                 415 att cgg gat caa ctt cta agt atg aat aga aac gct ttc ctt act ata      1296
Ile Arg Asp Gln Leu Leu Ser Met Asn Arg Asn Ala Phe Leu Thr Ile
        420                 425                 430 aat tct caa cct gct ctt aac ggc gaa aag agt tca cat cct gtt ttt      1344
Asn Ser Gln Pro Ala Leu Asn Gly Glu Lys Ser Ser His Pro Val Phe
    435                 440                 445 gga tgg gga cca cct aat ggt tat gtt ttc caa aaa cca tac gtt gag      1392
Gly Trp Gly Pro Pro Asn Gly Tyr Val Phe Gln Lys Pro Tyr Val Glu
450                 455                 460 ttt ttc gtt cac ccc tca ctc ttg aat gaa ctc aaa gaa acc gtt aaa      1440
Phe Phe Val His Pro Ser Leu Leu Asn Glu Leu Lys Glu Thr Val Lys
465                 470                 475                 480 aag ctt aat tca gtt tcc tac ttt gtt aca aac aag aat gga gac ttg      1488
Lys Leu Asn Ser Val Ser Tyr Phe Val Thr Asn Lys Asn Gly Asp Leu
            485                 490                 495 gat acc aac tca caa tat gag att cca aat gcg gtt aca tgg ggt gtt      1536
Asp Thr Asn Ser Gln Tyr Glu Ile Pro Asn Ala Val Thr Trp Gly Val
        500                 505                 510 ttc cct aat cgt gag att atc caa cct act att gtc gag tca acc tct      1584
Phe Pro Asn Arg Glu Ile Ile Gln Pro Thr Ile Val Glu Ser Thr Ser
    515                 520                 525 ttt ctt gct tgg aaa gat gaa gcc tat tca ttg ggc atg gaa tgg gct      1632
Phe Leu Ala Trp Lys Asp Glu Ala Tyr Ser Leu Gly Met Glu Trp Ala
530                 535                 540 aat gca tat agc cct gat tca att tct cgt aaa ctt ttg gtt tct atg      1680
Asn Ala Tyr Ser Pro Asp Ser Ile Ser Arg Lys Leu Leu Val Ser Met
545                 550                 555                 560 atg aag gaa tgg ttc ctt tgt gtc ata gtt gat aac gat ttt caa aat      1728
Met Lys Glu Trp Phe Leu Cys Val Ile Val Asp Asn Asp Phe Gln Asn
            565                 570                 575 ggg caa tct ttg ttt gat gtt ttt aac aaa atg aga tct tta aaa gac      1776
Gly Gln Ser Leu Phe Asp Val Phe Asn Lys Met Arg Ser Leu Lys Asp
        580                 585                 590 atc cat cct gag cta tat tat gca aat gca tca taa                      1812
Ile His Pro Glu Leu Tyr Tyr Ala Asn Ala Ser
    595                 600

<210> SEQ ID NO 22
<211> LENGTH: 603
<212> TYPE: PRT
<213> ORGANISM: Schizosaccharomyces pombe

<400> SEQUENCE: 22

Met Lys Ile Ser Asp Lys Leu Leu His Pro Asp Trp Lys Glu Lys Val
1               5                   10                  15

Thr Tyr Ser Tyr Glu Phe Phe Pro Pro Lys Thr Ser Thr Gly Val Gln
            20                  25                  30
```

-continued

```
Asn Leu Tyr Asn Arg Ile Asp Arg Met Lys Thr Trp Gly Arg Pro Met
         35                  40                  45
Phe Val Asp Val Thr Trp Gly Ala Gly Gly Thr Ser Ser Glu Leu Thr
 50                  55                  60
Pro Gly Ile Val Asn Val Ile Gln Thr Asp Phe Glu Val Asp Thr Cys
 65                  70                  75                  80
Met His Leu Thr Cys Thr Asn Met Ser Thr Glu Met Ile Asp Ala Ala
                 85                  90                  95
Leu Lys Arg Ala His Glu Thr Gly Cys Arg Asn Ile Leu Ala Leu Arg
                100                 105                 110
Gly Asp Pro Val Lys Asp Thr Asp Trp Thr Glu Gly Glu Ser Gly Phe
            115                 120                 125
Arg Tyr Ala Ser Asp Leu Val Arg Tyr Ile Arg Thr His Tyr Asn Asp
130                 135                 140
Glu Phe Cys Ile Gly Val Ala Gly Tyr Pro Glu Gly Tyr Ser Pro Asp
145                 150                 155                 160
Asp Asp Ile Asp Glu Ser Ile Lys His Leu Lys Leu Lys Val Asp Glu
                165                 170                 175
Gly Ala Asp Phe Ile Val Thr Gln Met Phe Tyr Asp Val Asp Asn Phe
            180                 185                 190
Ile Ala Trp Val Asp Lys Val Arg Ala Ala Gly Ile Asn Ile Pro Ile
            195                 200                 205
Phe Pro Gly Ile Met Pro Ile Gln Ala Trp Asp Ser Phe Ile Arg Arg
210                 215                 220
Ala Lys Trp Ser Gly Val Lys Ile Pro Gln His Phe Met Asp Thr Leu
225                 230                 235                 240
Val Pro Val Lys Asp Asp Glu Gly Val Arg Glu Arg Gly Val Glu
                245                 250                 255
Leu Ile Val Glu Met Cys Arg Lys Leu Ile Ala Ser Gly Ile Thr Arg
                260                 265                 270
Leu His Phe Tyr Thr Met Asn Leu Glu Lys Ala Val Lys Met Ile Ile
            275                 280                 285
Glu Arg Leu Gly Leu Leu Asp Glu Asn Leu Ala Pro Ile Val Asp Thr
            290                 295                 300
Asn Asn Val Glu Leu Thr Asn Ala Ser Ser Gln Asp Arg Arg Ile Asn
305                 310                 315                 320
Glu Gly Val Arg Pro Ile Phe Trp Arg Thr Arg Asn Glu Ser Tyr Val
                325                 330                 335
Ser Arg Thr Asp Gln Trp Asp Glu Leu Pro His Gly Arg Trp Gly Asp
            340                 345                 350
Ser Arg Ser Pro Ala Phe Gly Glu Phe Asp Ala Ile Arg Tyr Gly Leu
            355                 360                 365
Arg Met Ser Pro Lys Glu Ile Thr Thr Ser Trp Gly Ser Pro Lys Ser
370                 375                 380
Tyr Ser Glu Ile Gly Asp Leu Phe Ala Arg Tyr Cys Glu Lys Lys Ile
385                 390                 395                 400
Ser Ser Leu Pro Trp Ser Asp Leu Pro Ile Ser Asp Glu Ala Asp Leu
                405                 410                 415
Ile Arg Asp Gln Leu Leu Ser Met Asn Arg Asn Ala Phe Leu Thr Ile
            420                 425                 430
Asn Ser Gln Pro Ala Leu Asn Gly Glu Lys Ser Ser His Pro Val Phe
            435                 440                 445
Gly Trp Gly Pro Pro Asn Gly Tyr Val Phe Gln Lys Pro Tyr Val Glu
```

-continued

```
            450                 455                 460
Phe Phe Val His Pro Ser Leu Leu Asn Glu Leu Lys Glu Thr Val Lys
465                 470                 475                 480

Lys Leu Asn Ser Val Ser Tyr Phe Val Thr Asn Lys Asn Gly Asp Leu
                    485                 490                 495

Asp Thr Asn Ser Gln Tyr Glu Ile Pro Asn Ala Val Thr Trp Gly Val
                500                 505                 510

Phe Pro Asn Arg Glu Ile Ile Gln Pro Thr Ile Val Glu Ser Thr Ser
            515                 520                 525

Phe Leu Ala Trp Lys Asp Glu Ala Tyr Ser Leu Gly Met Glu Trp Ala
        530                 535                 540

Asn Ala Tyr Ser Pro Asp Ser Ile Ser Arg Lys Leu Leu Val Ser Met
545                 550                 555                 560

Met Lys Glu Trp Phe Leu Cys Val Ile Val Asp Asn Asp Phe Gln Asn
                565                 570                 575

Gly Gln Ser Leu Phe Asp Val Phe Asn Lys Met Arg Ser Leu Lys Asp
                580                 585                 590

Ile His Pro Glu Leu Tyr Tyr Ala Asn Ala Ser
            595                 600

<210> SEQ ID NO 23
<211> LENGTH: 1800
<212> TYPE: DNA
<213> ORGANISM: Saccharomyces cerevisiae
<220> FEATURE:
<221> NAME/KEY: CDS
<222> LOCATION: (1)..(1797)
<223> OTHER INFORMATION: RSC08323

<400> SEQUENCE: 23 atg aag atc aca gaa aaa tta gag caa cat aga cag acc tct ggc aag       48
Met Lys Ile Thr Glu Lys Leu Glu Gln His Arg Gln Thr Ser Gly Lys
  1               5                  10                  15 ccc act tac tca ttc gag tac ttc gtc ccg aag act aca caa ggt gta       96
Pro Thr Tyr Ser Phe Glu Tyr Phe Val Pro Lys Thr Thr Gln Gly Val
                 20                  25                  30 cag aac ctg tat gac cgg atg gac cgg atg tac gag gct tct ttg ccc      144
Gln Asn Leu Tyr Asp Arg Met Asp Arg Met Tyr Glu Ala Ser Leu Pro
             35                  40                  45 caa ttt att gac atc acc tgg aat gca ggc ggt gga cgg ttg tca cat      192
Gln Phe Ile Asp Ile Thr Trp Asn Ala Gly Gly Gly Arg Leu Ser His
         50                  55                  60 ctg tcc acg gac ttg gtt gcg aca gcg cag tct gtg ctt ggt ttg gaa      240
Leu Ser Thr Asp Leu Val Ala Thr Ala Gln Ser Val Leu Gly Leu Glu
 65                  70                  75                  80 acg tgc atg cac ctt acc tgc acc aat atg ccc att tcg atg att gac      288
Thr Cys Met His Leu Thr Cys Thr Asn Met Pro Ile Ser Met Ile Asp
                 85                  90                  95 gac gct tta gaa aac gct tat cac tcc ggt tgc cag aac atc cta gcg      336
Asp Ala Leu Glu Asn Ala Tyr His Ser Gly Cys Gln Asn Ile Leu Ala
                100                 105                 110 ctg aga gga gat cct cct agg gac gca gaa aac tgg act ccc gtt gaa      384
Leu Arg Gly Asp Pro Pro Arg Asp Ala Glu Asn Trp Thr Pro Val Glu
            115                 120                 125 ggt ggc ttc cag tat gcc aag gac ttg att aag tat atc aag tcc aag      432
Gly Gly Phe Gln Tyr Ala Lys Asp Leu Ile Lys Tyr Ile Lys Ser Lys
        130                 135                 140 tac ggt gac cat ttc gct atc ggc gtt gcc ggc tac ccg gag tgc cat      480
Tyr Gly Asp His Phe Ala Ile Gly Val Ala Gly Tyr Pro Glu Cys His
```

```
                    -continued
  145            150            155            160 ccg gag ttg cct aac aaa gac gtg aag ctt gat ctc gag tat ttg agc      528
Pro Glu Leu Pro Asn Lys Asp Val Lys Leu Asp Leu Glu Tyr Leu Ser
                165            170            175 aga aga tcg acc ggc ggc gac ttc atc atc act cag atg ttt tac gat      576
Arg Arg Ser Thr Gly Gly Asp Phe Ile Ile Thr Gln Met Phe Tyr Asp
            180            185            190 gtt gat aat tta ctc aac tgg tgt tcc caa gtt aga gct gcg ggc atg      624
Val Asp Asn Leu Leu Asn Trp Cys Ser Gln Val Arg Ala Ala Gly Met
        195            200            205 gac gtg ccc att att ccc ggg atc atg ccg atc act acc tac gcg gcc      672
Asp Val Pro Ile Ile Pro Gly Ile Met Pro Ile Thr Thr Tyr Ala Ala
    210            215            220 ttc ttg aga agg atc caa tgg ggc caa atc tcc atc cct caa cat ttc      720
Phe Leu Arg Arg Ile Gln Trp Gly Gln Ile Ser Ile Pro Gln His Phe
225            230            235            240 tcg tcc cga ttg gat cct atc aag gac gat gac gag ttg gtc cgt gat      768
Ser Ser Arg Leu Asp Pro Ile Lys Asp Asp Asp Glu Leu Val Arg Asp
                245            250            255 atc gga act aac ttg atc gtg gaa atg tgt caa aaa ttg ctc gac agt      816
Ile Gly Thr Asn Leu Ile Val Glu Met Cys Gln Lys Leu Leu Asp Ser
            260            265            270 ggt tac gtt tct cac ttg cac atc tac acc atg aac ttg gaa aaa gcg      864
Gly Tyr Val Ser His Leu His Ile Tyr Thr Met Asn Leu Glu Lys Ala
        275            280            285 cct ctc atg att ctg gaa aga ttg aac att cta cct acg gaa tca gag      912
Pro Leu Met Ile Leu Glu Arg Leu Asn Ile Leu Pro Thr Glu Ser Glu
    290            295            300 ttc aat gca cat cca ttg gcc gtg ttg cca tgg aga aaa tct ttg aat      960
Phe Asn Ala His Pro Leu Ala Val Leu Pro Trp Arg Lys Ser Leu Asn
305            310            315            320 cca aag cgt aaa aac gag gaa gtc aga cct atc ttc tgg aag aga aga     1008
Pro Lys Arg Lys Asn Glu Glu Val Arg Pro Ile Phe Trp Lys Arg Arg
                325            330            335 cct tac tcc tat gtc gca aga acc tct caa tgg gcc gtg gac gaa ttc     1056
Pro Tyr Ser Tyr Val Ala Arg Thr Ser Gln Trp Ala Val Asp Glu Phe
            340            345            350 ccc aac ggt aga ttc ggt gat tcg tct tct cct gcg ttc ggt gac ttg     1104
Pro Asn Gly Arg Phe Gly Asp Ser Ser Ser Pro Ala Phe Gly Asp Leu
        355            360            365 gat ctg tgt ggt tca gac ttg atc agg caa tca gcg aac aaa tgt ctc     1152
Asp Leu Cys Gly Ser Asp Leu Ile Arg Gln Ser Ala Asn Lys Cys Leu
    370            375            380 gaa tta tgg tcc acc cct act tcc atc aac gac gtc gcc ttc ttg gtc     1200
Glu Leu Trp Ser Thr Pro Thr Ser Ile Asn Asp Val Ala Phe Leu Val
385            390            395            400 atc aac tac ttg aat gga aac ttg aag tgt tta cct tgg agt gat atc     1248
Ile Asn Tyr Leu Asn Gly Asn Leu Lys Cys Leu Pro Trp Ser Asp Ile
                405            410            415 ccc atc aat gat gaa ata aat cca atc aaa gca cac ttg att gag ctg     1296
Pro Ile Asn Asp Glu Ile Asn Pro Ile Lys Ala His Leu Ile Glu Leu
            420            425            430 aac cag cat tct atc atc act ata aac tct caa cct caa gtc aac ggc     1344
Asn Gln His Ser Ile Ile Thr Ile Asn Ser Gln Pro Gln Val Asn Gly
        435            440            445 att agg tcc aat gac aaa att cat ggt tgg gga ccc aag gat ggt tac     1392
Ile Arg Ser Asn Asp Lys Ile His Gly Trp Gly Pro Lys Asp Gly Tyr
    450            455            460 gtt tac cag aag caa tat ttg gaa ttt atg ttg ccc aag act aag ttg     1440
Val Tyr Gln Lys Gln Tyr Leu Glu Phe Met Leu Pro Lys Thr Lys Leu
```

```
Val Tyr Gln Lys Gln Tyr Leu Glu Phe Met Leu Pro Lys Thr Lys Leu
465                 470                 475                 480 ccc aag ttg att gac acc ttg aaa aac aat gag ttc ttg acc tac ttc     1488
Pro Lys Leu Ile Asp Thr Leu Lys Asn Asn Glu Phe Leu Thr Tyr Phe
                485                 490                 495 gcc atc gac tct caa ggt gac ctg cta agt aat cat cca gac aac tcc     1536
Ala Ile Asp Ser Gln Gly Asp Leu Leu Ser Asn His Pro Asp Asn Ser
            500                 505                 510 aag tcc aac gct gtg act tgg ggt att ttc ccc ggc aga gaa att ctt     1584
Lys Ser Asn Ala Val Thr Trp Gly Ile Phe Pro Gly Arg Glu Ile Leu
        515                 520                 525 caa cct acc att gtc gag aaa att tcg ttc tta gcg tgg aag gag gag     1632
Gln Pro Thr Ile Val Glu Lys Ile Ser Phe Leu Ala Trp Lys Glu Glu
    530                 535                 540 ttc tat cat atc ttg aat gaa tgg aaa cta aac atg aat aaa tac gat     1680
Phe Tyr His Ile Leu Asn Glu Trp Lys Leu Asn Met Asn Lys Tyr Asp
545                 550                 555                 560 aaa ccg cat agt gcc caa ttc att cag tcc ttg att gac gat tac tgc     1728
Lys Pro His Ser Ala Gln Phe Ile Gln Ser Leu Ile Asp Asp Tyr Cys
                565                 570                 575 ttg gtc aat att gtt gac aat gac tac att tct cca gat gat caa atc     1776
Leu Val Asn Ile Val Asp Asn Asp Tyr Ile Ser Pro Asp Asp Gln Ile
            580                 585                 590 cat tcc atc cta cta agc cta taa                                     1800
His Ser Ile Leu Leu Ser Leu
        595

<210> SEQ ID NO 24
<211> LENGTH: 599
<212> TYPE: PRT
<213> ORGANISM: Saccharomyces cerevisiae

<400> SEQUENCE: 24

Met Lys Ile Thr Glu Lys Leu Glu Gln His Arg Gln Thr Ser Gly Lys
1               5                   10                  15

Pro Thr Tyr Ser Phe Glu Tyr Phe Val Pro Lys Thr Thr Gln Gly Val
                20                  25                  30

Gln Asn Leu Tyr Asp Arg Met Asp Arg Met Tyr Glu Ala Ser Leu Pro
            35                  40                  45

Gln Phe Ile Asp Ile Thr Trp Asn Ala Gly Gly Arg Leu Ser His
        50                  55                  60

Leu Ser Thr Asp Leu Val Ala Thr Ala Gln Ser Val Leu Gly Leu Glu
65                  70                  75                  80

Thr Cys Met His Leu Thr Cys Thr Asn Met Pro Ile Ser Met Ile Asp
                85                  90                  95

Asp Ala Leu Glu Asn Ala Tyr His Ser Gly Cys Gln Asn Ile Leu Ala
            100                 105                 110

Leu Arg Gly Asp Pro Pro Arg Asp Ala Glu Asn Trp Thr Pro Val Glu
        115                 120                 125

Gly Gly Phe Gln Tyr Ala Lys Asp Leu Ile Lys Tyr Ile Lys Ser Lys
    130                 135                 140

Tyr Gly Asp His Phe Ala Ile Gly Val Ala Gly Tyr Pro Glu Cys His
145                 150                 155                 160

Pro Glu Leu Pro Asn Lys Asp Val Lys Leu Asp Leu Glu Tyr Leu Ser
                165                 170                 175

Arg Arg Ser Thr Gly Gly Asp Phe Ile Ile Thr Gln Met Phe Tyr Asp
            180                 185                 190
```

```
Val Asp Asn Leu Leu Asn Trp Cys Ser Gln Val Arg Ala Ala Gly Met
    195                 200                 205

Asp Val Pro Ile Ile Pro Gly Ile Met Pro Ile Thr Thr Tyr Ala Ala
210                 215                 220

Phe Leu Arg Arg Ile Gln Trp Gly Gln Ile Ser Ile Pro Gln His Phe
225                 230                 235                 240

Ser Ser Arg Leu Asp Pro Ile Lys Asp Asp Glu Leu Val Arg Asp
                245                 250                 255

Ile Gly Thr Asn Leu Ile Val Glu Met Cys Gln Lys Leu Leu Asp Ser
                260                 265                 270

Gly Tyr Val Ser His Leu His Ile Tyr Thr Met Asn Leu Glu Lys Ala
            275                 280                 285

Pro Leu Met Ile Leu Glu Arg Leu Asn Ile Leu Pro Thr Glu Ser Glu
        290                 295                 300

Phe Asn Ala His Pro Leu Ala Val Leu Pro Trp Arg Lys Ser Leu Asn
305                 310                 315                 320

Pro Lys Arg Lys Asn Glu Val Arg Pro Ile Phe Trp Lys Arg Arg
                325                 330                 335

Pro Tyr Ser Tyr Val Ala Arg Thr Ser Gln Trp Ala Val Asp Glu Phe
            340                 345                 350

Pro Asn Gly Arg Phe Gly Asp Ser Ser Pro Ala Phe Gly Asp Leu
        355                 360                 365

Asp Leu Cys Gly Ser Asp Leu Ile Arg Gln Ser Ala Asn Lys Cys Leu
    370                 375                 380

Glu Leu Trp Ser Thr Pro Thr Ser Ile Asn Asp Val Ala Phe Leu Val
385                 390                 395                 400

Ile Asn Tyr Leu Asn Gly Asn Leu Lys Cys Leu Pro Trp Ser Asp Ile
                405                 410                 415

Pro Ile Asn Asp Glu Ile Asn Pro Ile Lys Ala His Leu Ile Glu Leu
                420                 425                 430

Asn Gln His Ser Ile Ile Thr Ile Asn Ser Gln Pro Gln Val Asn Gly
            435                 440                 445

Ile Arg Ser Asn Asp Lys Ile His Gly Trp Gly Pro Lys Asp Gly Tyr
    450                 455                 460

Val Tyr Gln Lys Gln Tyr Leu Glu Phe Met Leu Pro Lys Thr Lys Leu
465                 470                 475                 480

Pro Lys Leu Ile Asp Thr Leu Lys Asn Asn Glu Phe Leu Thr Tyr Phe
                485                 490                 495

Ala Ile Asp Ser Gln Gly Asp Leu Leu Ser Asn His Pro Asp Asn Ser
            500                 505                 510

Lys Ser Asn Ala Val Thr Trp Gly Ile Phe Pro Gly Arg Glu Ile Leu
    515                 520                 525

Gln Pro Thr Ile Val Glu Lys Ile Ser Phe Leu Ala Trp Lys Glu Glu
530                 535                 540

Phe Tyr His Ile Leu Asn Glu Trp Lys Leu Asn Met Asn Lys Tyr Asp
545                 550                 555                 560

Lys Pro His Ser Ala Gln Phe Ile Gln Ser Leu Ile Asp Asp Tyr Cys
                565                 570                 575

Leu Val Asn Ile Val Asp Asn Asp Tyr Ile Ser Pro Asp Asp Gln Ile
            580                 585                 590

His Ser Ile Leu Leu Ser Leu
        595
```

```
<210> SEQ ID NO 25
<211> LENGTH: 897
<212> TYPE: DNA
<213> ORGANISM: Erwinia carotovora
<220> FEATURE:
<221> NAME/KEY: CDS
<222> LOCATION: (1)..(894)
<223> OTHER INFORMATION: REO00089

<400> SEQUENCE: 25 atg agc ttt ttt cac gca aac cag cgg gaa gcg ctg aat caa agt ctg      48
Met Ser Phe Phe His Ala Asn Gln Arg Glu Ala Leu Asn Gln Ser Leu
 1               5                  10                  15 gcg gaa ttg cag gga cga att aat gtg tca ttt gaa ttt ttc ccg cca      96
Ala Glu Leu Gln Gly Arg Ile Asn Val Ser Phe Glu Phe Phe Pro Pro
             20                  25                  30 cgt acc agc gat atg gaa gaa acc ctg tgg agc tct atc gat cga ctg     144
Arg Thr Ser Asp Met Glu Glu Thr Leu Trp Ser Ser Ile Asp Arg Leu
         35                  40                  45 agc agc ctg aag ccc aag ttt gtt tcc gtg act tac ggg gcg aat tct     192
Ser Ser Leu Lys Pro Lys Phe Val Ser Val Thr Tyr Gly Ala Asn Ser
     50                  55                  60 ggc gag cgt gac cgt act cac agc att atc aaa acg att aaa gag cgt     240
Gly Glu Arg Asp Arg Thr His Ser Ile Ile Lys Thr Ile Lys Glu Arg
 65                  70                  75                  80 acc ggt ctg gaa gcg gca cct cac ctg acc tgc atc gat gct tca cgc     288
Thr Gly Leu Glu Ala Ala Pro His Leu Thr Cys Ile Asp Ala Ser Arg
                 85                  90                  95 gaa cag ctg cgt gaa atc gct cag gat tac tgg gag agt ggt atc cgc     336
Glu Gln Leu Arg Glu Ile Ala Gln Asp Tyr Trp Glu Ser Gly Ile Arg
            100                 105                 110 cat att gtc gcg ctg cgc ggc gac ttg cct caa gaa ggc ggc aaa ccg     384
His Ile Val Ala Leu Arg Gly Asp Leu Pro Gln Glu Gly Gly Lys Pro
        115                 120                 125 gac atg tac gcg gcg gat ctg gtt tcc ctg ctg aaa gag gtc ggt gat     432
Asp Met Tyr Ala Ala Asp Leu Val Ser Leu Leu Lys Glu Val Gly Asp
    130                 135                 140 ttc gat att tcc gtt gcc gcc tat cct gaa gta cac cct gaa gcg aaa     480
Phe Asp Ile Ser Val Ala Ala Tyr Pro Glu Val His Pro Glu Ala Lys
145                 150                 155                 160 agc gcg cag gct gac ctg att aac ctg aaa cac aag att gat gcc ggc     528
Ser Ala Gln Ala Asp Leu Ile Asn Leu Lys His Lys Ile Asp Ala Gly
                165                 170                 175 gcg aat cgc gct atc aca cag ttc ttt ttc gac gta gaa agc tat ttg     576
Ala Asn Arg Ala Ile Thr Gln Phe Phe Phe Asp Val Glu Ser Tyr Leu
            180                 185                 190 cgg ttc cgt gac cgc tgc gtg gca acg ggc atc gat gta gaa att gtg     624
Arg Phe Arg Asp Arg Cys Val Ala Thr Gly Ile Asp Val Glu Ile Val
        195                 200                 205 ccg ggc att ctg cca gta tcg aac ttc aaa cag ttg cag aaa ttt gcc     672
Pro Gly Ile Leu Pro Val Ser Asn Phe Lys Gln Leu Gln Lys Phe Ala
    210                 215                 220 acg atg acc aac gtc cgt gtg ccg aac tgg atg acg acc atg ttt gac     720
Thr Met Thr Asn Val Arg Val Pro Asn Trp Met Thr Thr Met Phe Asp
225                 230                 235                 240 ggc ctg gat aac gat cca gaa acc cgc aaa atg gtg ggg gcg tct atc     768
Gly Leu Asp Asn Asp Pro Glu Thr Arg Lys Met Val Gly Ala Ser Ile
                245                 250                 255 gcc atg gat atg gtg aaa att ctc agc cgc gaa ggc gta aaa gat ttc     816
Ala Met Asp Met Val Lys Ile Leu Ser Arg Glu Gly Val Lys Asp Phe
            260                 265                 270
```

```
cat ttc tat acg ctg aac cgc gcg gag ctg agc tat gcg att tgc cat      864
His Phe Tyr Thr Leu Asn Arg Ala Glu Leu Ser Tyr Ala Ile Cys His
        275                 280                 285 acg ctg ggc gtc cgc cct gat gta gca cgc tga                          897
Thr Leu Gly Val Arg Pro Asp Val Ala Arg
    290                 295
```

<210> SEQ ID NO 26
<211> LENGTH: 298
<212> TYPE: PRT
<213> ORGANISM: Erwinia carotovora

<400> SEQUENCE: 26

```
Met Ser Phe Phe His Ala Asn Gln Arg Glu Ala Leu Asn Gln Ser Leu
 1               5                  10                  15

Ala Glu Leu Gln Gly Arg Ile Asn Val Ser Phe Glu Phe Phe Pro Pro
             20                  25                  30

Arg Thr Ser Asp Met Glu Glu Thr Leu Trp Ser Ser Ile Asp Arg Leu
         35                  40                  45

Ser Ser Leu Lys Pro Lys Phe Val Ser Val Thr Tyr Gly Ala Asn Ser
     50                  55                  60

Gly Glu Arg Asp Arg Thr His Ser Ile Ile Lys Thr Ile Lys Glu Arg
 65                  70                  75                  80

Thr Gly Leu Glu Ala Ala Pro His Leu Thr Cys Ile Asp Ala Ser Arg
                 85                  90                  95

Glu Gln Leu Arg Glu Ile Ala Gln Asp Tyr Trp Glu Ser Gly Ile Arg
            100                 105                 110

His Ile Val Ala Leu Arg Gly Asp Leu Pro Gln Glu Gly Gly Lys Pro
        115                 120                 125

Asp Met Tyr Ala Ala Asp Leu Val Ser Leu Leu Lys Glu Val Gly Asp
    130                 135                 140

Phe Asp Ile Ser Val Ala Ala Tyr Pro Glu Val His Pro Glu Ala Lys
145                 150                 155                 160

Ser Ala Gln Ala Asp Leu Ile Asn Leu Lys His Lys Ile Asp Ala Gly
                165                 170                 175

Ala Asn Arg Ala Ile Thr Gln Phe Phe Phe Asp Val Glu Ser Tyr Leu
            180                 185                 190

Arg Phe Arg Asp Arg Cys Val Ala Thr Gly Ile Asp Val Glu Ile Val
        195                 200                 205

Pro Gly Ile Leu Pro Val Ser Asn Phe Lys Gln Leu Gln Lys Phe Ala
    210                 215                 220

Thr Met Thr Asn Val Arg Val Pro Asn Trp Met Thr Met Phe Asp
225                 230                 235                 240

Gly Leu Asp Asn Asp Pro Glu Thr Arg Lys Met Val Gly Ala Ser Ile
                245                 250                 255

Ala Met Asp Met Val Lys Ile Leu Ser Arg Glu Gly Val Lys Asp Phe
            260                 265                 270

His Phe Tyr Thr Leu Asn Arg Ala Glu Leu Ser Tyr Ala Ile Cys His
        275                 280                 285

Thr Leu Gly Val Arg Pro Asp Val Ala Arg
    290                 295
```

<210> SEQ ID NO 27
<211> LENGTH: 888
<212> TYPE: DNA
<213> ORGANISM: Klebsiella pneumoniae
<220> FEATURE:

<221> NAME/KEY: CDS
<222> LOCATION: (1)..(885)
<223> OTHER INFORMATION: RKP07488

<400> SEQUENCE: 27

| | | | | | | | | | | | | | | | | |
|---|---|---|---|---|---|---|---|---|---|---|---|---|---|---|---|---|
| atg | agc | ttt | ttt | cac | gcc | aat | cag | cgg | gaa | gcc | ctg | aat | cag | agc | ctg | 48 |
| Met | Ser | Phe | Phe | His | Ala | Asn | Gln | Arg | Glu | Ala | Leu | Asn | Gln | Ser | Leu | |
| 1 | | | | 5 | | | | | 10 | | | | | 15 | | |
| gcg | gaa | gtc | cag | ggc | cag | att | aat | gtg | tct | ttt | gaa | ttc | ttt | ccg | ccg | 96 |
| Ala | Glu | Val | Gln | Gly | Gln | Ile | Asn | Val | Ser | Phe | Glu | Phe | Phe | Pro | Pro | |
| | | | 20 | | | | | 25 | | | | | 30 | | | |
| cgc | acc | agt | gaa | atg | gag | caa | acc | ctg | tgg | aaa | tcc | atc | gat | cgc | ctg | 144 |
| Arg | Thr | Ser | Glu | Met | Glu | Gln | Thr | Leu | Trp | Lys | Ser | Ile | Asp | Arg | Leu | |
| | | 35 | | | | | 40 | | | | | 45 | | | | |
| agc | agt | ctg | aaa | ccg | aag | ttt | gtt | tcg | gta | acc | tat | ggc | gcg | aac | tct | 192 |
| Ser | Ser | Leu | Lys | Pro | Lys | Phe | Val | Ser | Val | Thr | Tyr | Gly | Ala | Asn | Ser | |
| 50 | | | | | 55 | | | | | 60 | | | | | | |
| ggc | gag | cgc | gat | cgc | acc | cac | agc | atc | atc | aaa | ggc | att | aaa | gag | cga | 240 |
| Gly | Glu | Arg | Asp | Arg | Thr | His | Ser | Ile | Ile | Lys | Gly | Ile | Lys | Glu | Arg | |
| 65 | | | | | 70 | | | | | 75 | | | | | 80 | |
| acc | ggt | ctg | gaa | gca | gcg | ccg | cac | ctg | acc | tgt | atc | gat | gcc | agc | cgc | 288 |
| Thr | Gly | Leu | Glu | Ala | Ala | Pro | His | Leu | Thr | Cys | Ile | Asp | Ala | Ser | Arg | |
| | | | | 85 | | | | | 90 | | | | | 95 | | |
| gat | gag | ttg | cgc | act | atc | gct | cag | gat | tac | tgg | aac | aac | ggt | atc | cgc | 336 |
| Asp | Glu | Leu | Arg | Thr | Ile | Ala | Gln | Asp | Tyr | Trp | Asn | Asn | Gly | Ile | Arg | |
| | | | 100 | | | | | 105 | | | | | 110 | | | |
| cat | atc | gtc | gcc | ctg | cgc | ggc | gac | ctg | ccg | ccg | ggc | agc | ggt | aaa | ccg | 384 |
| His | Ile | Val | Ala | Leu | Arg | Gly | Asp | Leu | Pro | Pro | Gly | Ser | Gly | Lys | Pro | |
| | | 115 | | | | | 120 | | | | | 125 | | | | |
| gat | atg | tac | gcc | gcc | gat | ctg | gtg | acg | ttg | ctg | aaa | gag | gta | ggc | gat | 432 |
| Asp | Met | Tyr | Ala | Ala | Asp | Leu | Val | Thr | Leu | Leu | Lys | Glu | Val | Gly | Asp | |
| 130 | | | | | 135 | | | | | 140 | | | | | | |
| ttt | gat | atc | tct | gtc | gcc | gcg | tat | ccg | gaa | gtg | cat | ccg | gag | gcg | aaa | 480 |
| Phe | Asp | Ile | Ser | Val | Ala | Ala | Tyr | Pro | Glu | Val | His | Pro | Glu | Ala | Lys | |
| 145 | | | | 150 | | | | | 155 | | | | | 160 | | |
| agc | gcg | cag | gcg | gat | tta | ctg | aac | ctg | aag | cgc | aaa | gta | gaa | gca | ggg | 528 |
| Ser | Ala | Gln | Ala | Asp | Leu | Leu | Asn | Leu | Lys | Arg | Lys | Val | Glu | Ala | Gly | |
| | | | | 165 | | | | | 170 | | | | | 175 | | |
| gcc | aac | cgc | gcg | atc | acc | cag | ttc | ttc | ttc | gat | gtg | gaa | agc | tac | ctg | 576 |
| Ala | Asn | Arg | Ala | Ile | Thr | Gln | Phe | Phe | Phe | Asp | Val | Glu | Ser | Tyr | Leu | |
| | | | 180 | | | | | 185 | | | | | 190 | | | |
| cgt | ttt | cgc | gat | cgc | tgc | gtc | tcg | gca | ggc | atc | gac | gtg | gaa | atc | att | 624 |
| Arg | Phe | Arg | Asp | Arg | Cys | Val | Ser | Ala | Gly | Ile | Asp | Val | Glu | Ile | Ile | |
| | | 195 | | | | | 200 | | | | | 205 | | | | |
| ccc | ggt | atc | ctg | ccg | gtc | tcc | aac | ttt | aaa | cag | gcg | aaa | aag | ttt | gcg | 672 |
| Pro | Gly | Ile | Leu | Pro | Val | Ser | Asn | Phe | Lys | Gln | Ala | Lys | Lys | Phe | Ala | |
| 210 | | | | | 215 | | | | | 220 | | | | | | |
| gat | atg | acc | aac | gtc | cgt | atc | ccg | gtg | tgg | atg | tca | aaa | atg | ttc | gaa | 720 |
| Asp | Met | Thr | Asn | Val | Arg | Ile | Pro | Val | Trp | Met | Ser | Lys | Met | Phe | Glu | |
| 225 | | | | 230 | | | | | 235 | | | | | 240 | | |
| ggg | ctg | gat | aac | gac | gcc | gaa | acc | cgt | caa | ctg | gtg | ggg | gcg | aat | atc | 768 |
| Gly | Leu | Asp | Asn | Asp | Ala | Glu | Thr | Arg | Gln | Leu | Val | Gly | Ala | Asn | Ile | |
| | | | | 245 | | | | | 250 | | | | | 255 | | |
| gcc | atg | gac | atg | gtg | aag | atc | tta | agc | cgg | gaa | ggg | gtc | aag | gat | ttc | 816 |
| Ala | Met | Asp | Met | Val | Lys | Ile | Leu | Ser | Arg | Glu | Gly | Val | Lys | Asp | Phe | |
| | | | 260 | | | | | 265 | | | | | 270 | | | |
| cac | ttc | tac | acc | ctg | aac | cgc | gcc | gag | atg | agc | tac | gcc | atc | tgc | cat | 864 |
| His | Phe | Tyr | Thr | Leu | Asn | Arg | Ala | Glu | Met | Ser | Tyr | Ala | Ile | Cys | His | |
| | | 275 | | | | | 280 | | | | | 285 | | | | |
| acg | ctg | ggc | gta | cgc | ccg | gcc | tga | | | | | | | | | 888 |

Thr Leu Gly Val Arg Pro Ala
    290             295

<210> SEQ ID NO 28
<211> LENGTH: 295
<212> TYPE: PRT
<213> ORGANISM: Klebsiella pneumoniae

<400> SEQUENCE: 28

Met Ser Phe Phe His Ala Asn Gln Arg Glu Ala Leu Asn Gln Ser Leu
 1               5                  10                  15

Ala Glu Val Gln Gly Gln Ile Asn Val Ser Phe Glu Phe Phe Pro Pro
            20                  25                  30

Arg Thr Ser Glu Met Glu Gln Thr Leu Trp Lys Ser Ile Asp Arg Leu
        35                  40                  45

Ser Ser Leu Lys Pro Lys Phe Val Ser Val Thr Tyr Gly Ala Asn Ser
    50                  55                  60

Gly Glu Arg Asp Arg Thr His Ser Ile Ile Lys Gly Ile Lys Glu Arg
65                  70                  75                  80

Thr Gly Leu Glu Ala Ala Pro His Leu Thr Cys Ile Asp Ala Ser Arg
                85                  90                  95

Asp Glu Leu Arg Thr Ile Ala Gln Asp Tyr Trp Asn Asn Gly Ile Arg
            100                 105                 110

His Ile Val Ala Leu Arg Gly Asp Leu Pro Pro Gly Ser Gly Lys Pro
        115                 120                 125

Asp Met Tyr Ala Ala Asp Leu Val Thr Leu Leu Lys Glu Val Gly Asp
    130                 135                 140

Phe Asp Ile Ser Val Ala Ala Tyr Pro Glu Val His Pro Glu Ala Lys
145                 150                 155                 160

Ser Ala Gln Ala Asp Leu Leu Asn Leu Lys Arg Lys Val Glu Ala Gly
                165                 170                 175

Ala Asn Arg Ala Ile Thr Gln Phe Phe Phe Asp Val Glu Ser Tyr Leu
            180                 185                 190

Arg Phe Arg Asp Arg Cys Val Ser Ala Gly Ile Asp Val Glu Ile Ile
        195                 200                 205

Pro Gly Ile Leu Pro Val Ser Asn Phe Lys Gln Ala Lys Lys Phe Ala
    210                 215                 220

Asp Met Thr Asn Val Arg Ile Pro Val Trp Met Ser Lys Met Phe Glu
225                 230                 235                 240

Gly Leu Asp Asn Asp Ala Glu Thr Arg Gln Leu Val Gly Ala Asn Ile
                245                 250                 255

Ala Met Asp Met Val Lys Ile Leu Ser Arg Glu Gly Val Lys Asp Phe
            260                 265                 270

His Phe Tyr Thr Leu Asn Arg Ala Glu Met Ser Tyr Ala Ile Cys His
        275                 280                 285

Thr Leu Gly Val Arg Pro Ala
    290             295

<210> SEQ ID NO 29
<211> LENGTH: 891
<212> TYPE: DNA
<213> ORGANISM: Salmonella typhi
<220> FEATURE:
<221> NAME/KEY: CDS
<222> LOCATION: (1)..(888)
<223> OTHER INFORMATION: RTY02485

<400> SEQUENCE: 29

```
atg agc ttt ttt cac gcc aac cag cgg gaa gcc ctg aat cag agc ctg      48
Met Ser Phe Phe His Ala Asn Gln Arg Glu Ala Leu Asn Gln Ser Leu
 1               5                  10                  15 gcg gaa gta cag ggt cag att aac gtt tcg ttt gaa ttt ttc ccg ccg      96
Ala Glu Val Gln Gly Gln Ile Asn Val Ser Phe Glu Phe Phe Pro Pro
             20                  25                  30 cgc acc agt gaa atg gag caa acc ctg tgg aac tcc atc gat cgc ctg     144
Arg Thr Ser Glu Met Glu Gln Thr Leu Trp Asn Ser Ile Asp Arg Leu
         35                  40                  45 agc agc ctg aaa ccg aag ttt gtt tcg gta acg tat ggc gcc aac tcc     192
Ser Ser Leu Lys Pro Lys Phe Val Ser Val Thr Tyr Gly Ala Asn Ser
     50                  55                  60 ggg gaa cgt gac cgc act cat agt gtt att aaa ggc att aaa gag cgt     240
Gly Glu Arg Asp Arg Thr His Ser Val Ile Lys Gly Ile Lys Glu Arg
 65                  70                  75                  80 act ggg ctt gag gcc gcg ccg cac ctt acc tgt att gac gcc acg cgc     288
Thr Gly Leu Glu Ala Ala Pro His Leu Thr Cys Ile Asp Ala Thr Arg
                 85                  90                  95 gat gaa ctg cgc acc atc gcc cgc gac tac tgg aat aac ggt atc cgc     336
Asp Glu Leu Arg Thr Ile Ala Arg Asp Tyr Trp Asn Asn Gly Ile Arg
            100                 105                 110 cac att gtt gct ttg cgc ggc gat ttg ccg ccg ggc agc ggt aag ccg     384
His Ile Val Ala Leu Arg Gly Asp Leu Pro Pro Gly Ser Gly Lys Pro
        115                 120                 125 gag atg tac gcc gcc gat ctg gtt ggt ttg ctc aaa gag gtg gtc gat     432
Glu Met Tyr Ala Ala Asp Leu Val Gly Leu Leu Lys Glu Val Val Asp
    130                 135                 140 ttc gat att tca gta gcg gcc tat ccg gag gta cat ccg gaa gcg aaa     480
Phe Asp Ile Ser Val Ala Ala Tyr Pro Glu Val His Pro Glu Ala Lys
145                 150                 155                 160 agc gcg cag gcc gat ctg ctt aat ctg aag cgt aaa gtg gat gct ggc     528
Ser Ala Gln Ala Asp Leu Leu Asn Leu Lys Arg Lys Val Asp Ala Gly
                165                 170                 175 gct aac cgc gcg ata acc caa ttt ttc ttc gat gtg gaa agc tat ctg     576
Ala Asn Arg Ala Ile Thr Gln Phe Phe Phe Asp Val Glu Ser Tyr Leu
            180                 185                 190 cgt ttt cgc gac cgc tgt gtt tcc gcc ggt atc gac gta gaa att att     624
Arg Phe Arg Asp Arg Cys Val Ser Ala Gly Ile Asp Val Glu Ile Ile
        195                 200                 205 ccc ggc att tta ccg gtg tct aac ttt aaa cag gcg aaa aaa ttt gcc     672
Pro Gly Ile Leu Pro Val Ser Asn Phe Lys Gln Ala Lys Lys Phe Ala
    210                 215                 220 gat atg acc aat gtc cgc att ccg tcc tgg atg tcg ctg atg ttt gag     720
Asp Met Thr Asn Val Arg Ile Pro Ser Trp Met Ser Leu Met Phe Glu
225                 230                 235                 240 ggg ctg gat gat gac gca gaa acc cgc aag ctg gtg ggc gct aac att     768
Gly Leu Asp Asp Asp Ala Glu Thr Arg Lys Leu Val Gly Ala Asn Ile
                245                 250                 255 gcg atg gac atg gtg aaa att tta agc cgc gaa gga gtg aag gat ttc     816
Ala Met Asp Met Val Lys Ile Leu Ser Arg Glu Gly Val Lys Asp Phe
            260                 265                 270 cac ttc tac acg ttg aat cgt gcg gaa atg agt tat gcc att tgc cac     864
His Phe Tyr Thr Leu Asn Arg Ala Glu Met Ser Tyr Ala Ile Cys His
        275                 280                 285 acg ctg ggc gta aga ccg ggt tta taa                                 891
Thr Leu Gly Val Arg Pro Gly Leu
    290                 295
```

<210> SEQ ID NO 30

<211> LENGTH: 296
<212> TYPE: PRT
<213> ORGANISM: Salmonella typhi

<400> SEQUENCE: 30

```
Met Ser Phe Phe His Ala Asn Gln Arg Glu Ala Leu Asn Gln Ser Leu
 1               5                  10                  15

Ala Glu Val Gln Gly Gln Ile Asn Val Ser Phe Glu Phe Pro Pro
             20                  25                  30

Arg Thr Ser Glu Met Glu Gln Thr Leu Trp Asn Ser Ile Asp Arg Leu
             35                  40                  45

Ser Ser Leu Lys Pro Lys Phe Val Ser Val Thr Tyr Gly Ala Asn Ser
     50                  55                  60

Gly Glu Arg Asp Arg Thr His Ser Val Ile Lys Gly Ile Lys Glu Arg
 65                  70                  75                  80

Thr Gly Leu Glu Ala Ala Pro His Leu Thr Cys Ile Asp Ala Thr Arg
                 85                  90                  95

Asp Glu Leu Arg Thr Ile Ala Arg Asp Tyr Trp Asn Asn Gly Ile Arg
             100                 105                 110

His Ile Val Ala Leu Arg Gly Asp Leu Pro Pro Gly Ser Gly Lys Pro
         115                 120                 125

Glu Met Tyr Ala Ala Asp Leu Val Gly Leu Leu Lys Glu Val Val Asp
130                 135                 140

Phe Asp Ile Ser Val Ala Ala Tyr Pro Glu Val His Pro Glu Ala Lys
145                 150                 155                 160

Ser Ala Gln Ala Asp Leu Leu Asn Leu Lys Arg Lys Val Asp Ala Gly
                 165                 170                 175

Ala Asn Arg Ala Ile Thr Gln Phe Phe Phe Asp Val Glu Ser Tyr Leu
             180                 185                 190

Arg Phe Arg Asp Arg Cys Val Ser Ala Gly Ile Asp Val Glu Ile Ile
         195                 200                 205

Pro Gly Ile Leu Pro Val Ser Asn Phe Lys Gln Ala Lys Lys Phe Ala
     210                 215                 220

Asp Met Thr Asn Val Arg Ile Pro Ser Trp Met Ser Leu Met Phe Glu
225                 230                 235                 240

Gly Leu Asp Asp Ala Glu Thr Arg Lys Leu Val Gly Ala Asn Ile
                 245                 250                 255

Ala Met Asp Met Val Lys Ile Leu Ser Arg Glu Gly Val Lys Asp Phe
             260                 265                 270

His Phe Tyr Thr Leu Asn Arg Ala Glu Met Ser Tyr Ala Ile Cys His
         275                 280                 285

Thr Leu Gly Val Arg Pro Gly Leu
     290                 295
```

<210> SEQ ID NO 31
<211> LENGTH: 891
<212> TYPE: DNA
<213> ORGANISM: Salmonella typhimurium
<220> FEATURE:
<221> NAME/KEY: CDS
<222> LOCATION: (1)..(888)
<223> OTHER INFORMATION: RSY00593

<400> SEQUENCE: 31

```
atg agc ttt ttt cac gcc aac cag cgg gaa gcc ctg aat cag agc ctg     48
Met Ser Phe Phe His Ala Asn Gln Arg Glu Ala Leu Asn Gln Ser Leu
 1               5                  10                  15
```

```
gcg gaa gta cag ggt cag att aac gtt tcg ttt gaa ttt ttc ccg ccg      96
Ala Glu Val Gln Gly Gln Ile Asn Val Ser Phe Glu Phe Phe Pro Pro
         20                  25                  30 cgc acc agt gaa atg gag caa acc ctg tgg aac tcc atc gat cgc ctg     144
Arg Thr Ser Glu Met Glu Gln Thr Leu Trp Asn Ser Ile Asp Arg Leu
     35                  40                  45 agc agt ctg aaa ccg aag ttt gtt tcg gta acg tat ggc gcc aac tcc     192
Ser Ser Leu Lys Pro Lys Phe Val Ser Val Thr Tyr Gly Ala Asn Ser
 50                  55                  60 ggg gaa cgc gac cgc acc cat agc gtt att aaa ggc atc aaa gag cgt     240
Gly Glu Arg Asp Arg Thr His Ser Val Ile Lys Gly Ile Lys Glu Arg
 65                  70                  75                  80 act ggg ctt gag gcc gcg ccg cac ctt acc tgt att gac gcc acg cgc     288
Thr Gly Leu Glu Ala Ala Pro His Leu Thr Cys Ile Asp Ala Thr Arg
                 85                  90                  95 gat gaa ctg cgc acc atc gcc cgc gac tac tgg aat aac ggt atc cgc     336
Asp Glu Leu Arg Thr Ile Ala Arg Asp Tyr Trp Asn Asn Gly Ile Arg
            100                 105                 110 cac att gtc gct ttg cgc ggc gat ttg ccg ccg ggc agc ggt aag ccg     384
His Ile Val Ala Leu Arg Gly Asp Leu Pro Pro Gly Ser Gly Lys Pro
        115                 120                 125 gag atg tac gcc gcc gat ctg gtt ggt ttg ctc aaa gag gtg gcc gat     432
Glu Met Tyr Ala Ala Asp Leu Val Gly Leu Leu Lys Glu Val Ala Asp
130                 135                 140 ttc gat att tca gta gcg gcc tat ccg gag gta cat ccg gaa gcg aaa     480
Phe Asp Ile Ser Val Ala Ala Tyr Pro Glu Val His Pro Glu Ala Lys
145                 150                 155                 160 agc gcg cag gcc gat ctg ctt aat ctg aag cgt aaa gtg gat gct ggc     528
Ser Ala Gln Ala Asp Leu Leu Asn Leu Lys Arg Lys Val Asp Ala Gly
                165                 170                 175 gct aac cgc gcg ata acc caa ttt ttc ttc gat gtg gaa agc tac ctg     576
Ala Asn Arg Ala Ile Thr Gln Phe Phe Phe Asp Val Glu Ser Tyr Leu
            180                 185                 190 cgt ttt cgc gac cgc tgt gtt tct gcc ggt atc gac gta gaa att att     624
Arg Phe Arg Asp Arg Cys Val Ser Ala Gly Ile Asp Val Glu Ile Ile
        195                 200                 205 ccc ggc att tta ccg gtg tct aac ttt aaa cag gca aaa aaa ttt gcc     672
Pro Gly Ile Leu Pro Val Ser Asn Phe Lys Gln Ala Lys Lys Phe Ala
210                 215                 220 gat atg acc aat gtc cgc att ccg tcc tgg atg tca ctg atg ttt gag     720
Asp Met Thr Asn Val Arg Ile Pro Ser Trp Met Ser Leu Met Phe Glu
225                 230                 235                 240 ggg ctg gat aat gac gca gaa acc cgc aag ctg gtg ggc gct aac att     768
Gly Leu Asp Asn Asp Ala Glu Thr Arg Lys Leu Val Gly Ala Asn Ile
                245                 250                 255 gcg atg gac atg gtg aaa att tta agc cgt gaa gga gtg aag gat ttc     816
Ala Met Asp Met Val Lys Ile Leu Ser Arg Glu Gly Val Lys Asp Phe
            260                 265                 270 cac ttc tac acg ttg aat cgt gcg gaa atg agt tat gcc att tgc cac     864
His Phe Tyr Thr Leu Asn Arg Ala Glu Met Ser Tyr Ala Ile Cys His
        275                 280                 285 acg ctg ggc gta aga ccg ggt tta taa                                 891
Thr Leu Gly Val Arg Pro Gly Leu
    290                 295
```

<210> SEQ ID NO 32
<211> LENGTH: 296
<212> TYPE: PRT
<213> ORGANISM: Salmonella typhimurium

<400> SEQUENCE: 32

```
Met Ser Phe Phe His Ala Asn Gln Arg Glu Ala Leu Asn Gln Ser Leu
 1               5                  10                  15

Ala Glu Val Gln Gly Gln Ile Asn Val Ser Phe Glu Phe Pro Pro
            20                  25                  30

Arg Thr Ser Glu Met Glu Gln Thr Leu Trp Asn Ser Ile Asp Arg Leu
            35                  40                  45

Ser Ser Leu Lys Pro Lys Phe Val Ser Val Thr Tyr Gly Ala Asn Ser
        50                  55                  60

Gly Glu Arg Asp Arg Thr His Ser Val Ile Lys Gly Ile Lys Glu Arg
 65                 70                  75                  80

Thr Gly Leu Glu Ala Ala Pro His Leu Thr Cys Ile Asp Ala Thr Arg
                85                  90                  95

Asp Glu Leu Arg Thr Ile Ala Arg Asp Tyr Trp Asn Asn Gly Ile Arg
                100                 105                 110

His Ile Val Ala Leu Arg Gly Asp Leu Pro Pro Gly Ser Gly Lys Pro
            115                 120                 125

Glu Met Tyr Ala Ala Asp Leu Val Gly Leu Leu Lys Glu Val Ala Asp
130                 135                 140

Phe Asp Ile Ser Val Ala Ala Tyr Pro Glu Val His Pro Glu Ala Lys
145                 150                 155                 160

Ser Ala Gln Ala Asp Leu Leu Asn Leu Lys Arg Lys Val Asp Ala Gly
                165                 170                 175

Ala Asn Arg Ala Ile Thr Gln Phe Phe Phe Asp Val Glu Ser Tyr Leu
            180                 185                 190

Arg Phe Arg Asp Arg Cys Val Ser Ala Gly Ile Asp Val Glu Ile Ile
        195                 200                 205

Pro Gly Ile Leu Pro Val Ser Asn Phe Lys Gln Ala Lys Lys Phe Ala
210                 215                 220

Asp Met Thr Asn Val Arg Ile Pro Ser Trp Met Ser Leu Met Phe Glu
225                 230                 235                 240

Gly Leu Asp Asn Asp Ala Glu Thr Arg Lys Leu Val Gly Ala Asn Ile
                245                 250                 255

Ala Met Asp Met Val Lys Ile Leu Ser Arg Glu Gly Val Lys Asp Phe
            260                 265                 270

His Phe Tyr Thr Leu Asn Arg Ala Glu Met Ser Tyr Ala Ile Cys His
        275                 280                 285

Thr Leu Gly Val Arg Pro Gly Leu
    290                 295

<210> SEQ ID NO 33
<211> LENGTH: 891
<212> TYPE: DNA
<213> ORGANISM: Escherichia coli
<220> FEATURE:
<221> NAME/KEY: CDS
<222> LOCATION: (1)..(888)
<223> OTHER INFORMATION: REC03839

<400> SEQUENCE: 33 atg agc ttt ttt cac gcc agc cag cgg gat gcc ctg aat cag agc ctg      48
Met Ser Phe Phe His Ala Ser Gln Arg Asp Ala Leu Asn Gln Ser Leu
 1               5                  10                  15 gca gaa gtc cag ggg cag att aac gtt tcg ttc gag ttt ttc ccg ccg      96
Ala Glu Val Gln Gly Gln Ile Asn Val Ser Phe Glu Phe Phe Pro Pro
            20                  25                  30 cgt acc agt gaa atg gag cag acc ctg tgg aac tcc atc gat cgc ctt     144
```

```
Arg Thr Ser Glu Met Glu Gln Thr Leu Trp Asn Ser Ile Asp Arg Leu
         35                  40                  45 agc agc ctg aaa ccg aag ttt gta tcg gtg acc tat ggc gcg aac tcc    192
Ser Ser Leu Lys Pro Lys Phe Val Ser Val Thr Tyr Gly Ala Asn Ser
 50                  55                  60 ggc gag cgc gac cgt acg cac agc att att aaa ggc att aaa gat cgc    240
Gly Glu Arg Asp Arg Thr His Ser Ile Ile Lys Gly Ile Lys Asp Arg
 65                  70                  75                  80 act ggt ctg gaa gcg gca ccg cat ctt act tgc att gat gcg acg ccc    288
Thr Gly Leu Glu Ala Ala Pro His Leu Thr Cys Ile Asp Ala Thr Pro
                     85                  90                  95 gac gag ctg cgc acc att gca cgc gac tac tgg aat aac ggt att cgt    336
Asp Glu Leu Arg Thr Ile Ala Arg Asp Tyr Trp Asn Asn Gly Ile Arg
                    100                 105                 110 cat atc gtg gcg ctg cgt ggc gat ctg ccg ccg gga agt ggt aag cca    384
His Ile Val Ala Leu Arg Gly Asp Leu Pro Pro Gly Ser Gly Lys Pro
            115                 120                 125 gaa atg tat gct tct gac ctg gtg acg ctg tta aaa gaa gtg gca gat    432
Glu Met Tyr Ala Ser Asp Leu Val Thr Leu Leu Lys Glu Val Ala Asp
    130                 135                 140 ttc gat atc tcc gtg gcg gcg tat ccg gaa gtt cac ccg gaa gca aaa    480
Phe Asp Ile Ser Val Ala Ala Tyr Pro Glu Val His Pro Glu Ala Lys
145                 150                 155                 160 agc gct cag gcg gat ttg ctt aat ctg aaa cgc aaa gtg gat gcc gga    528
Ser Ala Gln Ala Asp Leu Leu Asn Leu Lys Arg Lys Val Asp Ala Gly
                    165                 170                 175 gcc aac cgc gcg att act cag ttc ttc ttc gat gtc gaa agc tac ctg    576
Ala Asn Arg Ala Ile Thr Gln Phe Phe Phe Asp Val Glu Ser Tyr Leu
                180                 185                 190 cgt ttt cgt gac cgc tgt gta tcg gcg ggc att gat gtg gaa att att    624
Arg Phe Arg Asp Arg Cys Val Ser Ala Gly Ile Asp Val Glu Ile Ile
            195                 200                 205 ccg gga att ttg ccg gta tct aac ttt aaa cag gcg aag aaa ttt gcc    672
Pro Gly Ile Leu Pro Val Ser Asn Phe Lys Gln Ala Lys Lys Phe Ala
    210                 215                 220 gat atg acc aac gtg cgt att ccg gcg tgg atg gcg caa atg ttc gac    720
Asp Met Thr Asn Val Arg Ile Pro Ala Trp Met Ala Gln Met Phe Asp
225                 230                 235                 240 ggt ctg gat gat gat gcc gaa acc cgc aaa ctg gtt ggc gcg aat att    768
Gly Leu Asp Asp Asp Ala Glu Thr Arg Lys Leu Val Gly Ala Asn Ile
                245                 250                 255 gcc atg gat atg gtg aag att tta agc cgt gaa gga gtg aaa gat ttc    816
Ala Met Asp Met Val Lys Ile Leu Ser Arg Glu Gly Val Lys Asp Phe
                260                 265                 270 cac ttc tat acg ctt aac cgt gct gaa atg agt tac gcg att tgc cat    864
His Phe Tyr Thr Leu Asn Arg Ala Glu Met Ser Tyr Ala Ile Cys His
            275                 280                 285 acg ctg ggg gtt cga cct ggt tta taa                                891
Thr Leu Gly Val Arg Pro Gly Leu
    290                 295

<210> SEQ ID NO 34
<211> LENGTH: 296
<212> TYPE: PRT
<213> ORGANISM: Escherichia coli

<400> SEQUENCE: 34

Met Ser Phe Phe His Ala Ser Gln Arg Asp Ala Leu Asn Gln Ser Leu
 1               5                  10                  15

Ala Glu Val Gln Gly Gln Ile Asn Val Ser Phe Glu Phe Phe Pro Pro
```

-continued

```
                    20                  25                  30
Arg Thr Ser Glu Met Glu Gln Thr Leu Trp Asn Ser Ile Asp Arg Leu
         35                  40                  45
Ser Ser Leu Lys Pro Lys Phe Val Ser Val Thr Tyr Gly Ala Asn Ser
     50                  55                  60
Gly Glu Arg Asp Arg Thr His Ser Ile Ile Lys Gly Ile Lys Asp Arg
 65                  70                  75                  80
Thr Gly Leu Glu Ala Ala Pro His Leu Thr Cys Ile Asp Ala Thr Pro
                 85                  90                  95
Asp Glu Leu Arg Thr Ile Ala Arg Asp Tyr Trp Asn Asn Gly Ile Arg
             100                 105                 110
His Ile Val Ala Leu Arg Gly Asp Leu Pro Pro Gly Ser Gly Lys Pro
         115                 120                 125
Glu Met Tyr Ala Ser Asp Leu Val Thr Leu Leu Lys Glu Val Ala Asp
     130                 135                 140
Phe Asp Ile Ser Val Ala Ala Tyr Pro Glu Val His Pro Glu Ala Lys
145                 150                 155                 160
Ser Ala Gln Ala Asp Leu Leu Asn Leu Lys Arg Lys Val Asp Ala Gly
                165                 170                 175
Ala Asn Arg Ala Ile Thr Gln Phe Phe Phe Asp Val Glu Ser Tyr Leu
            180                 185                 190
Arg Phe Arg Asp Arg Cys Val Ser Ala Gly Ile Asp Val Glu Ile Ile
        195                 200                 205
Pro Gly Ile Leu Pro Val Ser Asn Phe Lys Gln Ala Lys Lys Phe Ala
    210                 215                 220
Asp Met Thr Asn Val Arg Ile Pro Ala Trp Met Ala Gln Met Phe Asp
225                 230                 235                 240
Gly Leu Asp Asp Ala Glu Thr Arg Lys Leu Val Gly Ala Asn Ile
                245                 250                 255
Ala Met Asp Met Val Lys Ile Leu Ser Arg Glu Gly Val Lys Asp Phe
            260                 265                 270
His Phe Tyr Thr Leu Asn Arg Ala Glu Met Ser Tyr Ala Ile Cys His
        275                 280                 285
Thr Leu Gly Val Arg Pro Gly Leu
    290                 295
```

<210> SEQ ID NO 35
<211> LENGTH: 915
<212> TYPE: DNA
<213> ORGANISM: Vibrio cholerae
<220> FEATURE:
<221> NAME/KEY: CDS
<222> LOCATION: (1)..(912)
<223> OTHER INFORMATION: RVC06433

<400> SEQUENCE: 35

```
gtg aca ctc ggt cac agg gag tac aag atg gga tac aca cac gct agc      48
Val Thr Leu Gly His Arg Glu Tyr Lys Met Gly Tyr Thr His Ala Ser
 1               5                  10                  15 cat atc gat gca ttg aac caa aac att gcg gag ctt tcc gac atc aat      96
His Ile Asp Ala Leu Asn Gln Asn Ile Ala Glu Leu Ser Asp Ile Asn
             20                  25                  30 gtt tcg ttt gag ttt ttt cca ccc agc tca cca caa atg gaa gaa acg     144
Val Ser Phe Glu Phe Phe Pro Pro Ser Ser Pro Gln Met Glu Glu Thr
         35                  40                  45 ctt tgg gga tcg gta cac cgt ctg aaa aca ctc caa ccg aaa ttt gtt     192
Leu Trp Gly Ser Val His Arg Leu Lys Thr Leu Gln Pro Lys Phe Val
     50                  55                  60
```

| | | |
|---|---|---|
| tcg gtc act tat ggt gca aac tct ggt gag cgt gac cgt act cac tcg<br>Ser Val Thr Tyr Gly Ala Asn Ser Gly Glu Arg Asp Arg Thr His Ser<br>65     70     75     80 | | 240 |
| atc att aaa gcg atc aaa gat caa acc ggt tta att gcc gcg cca cac<br>Ile Ile Lys Ala Ile Lys Asp Gln Thr Gly Leu Ile Ala Ala Pro His<br>     85     90     95 | | 288 |
| ctg act tgt atc gat gcc act cgt gat gaa ctg atc cag atc gcc gat<br>Leu Thr Cys Ile Asp Ala Thr Arg Asp Glu Leu Ile Gln Ile Ala Asp<br>   100     105     110 | | 336 |
| gac tac tgg cat aac ggc atc cag aat att gtg gcg ctg cgt ggg gat<br>Asp Tyr Trp His Asn Gly Ile Gln Asn Ile Val Ala Leu Arg Gly Asp<br>     115     120     125 | | 384 |
| atc ccg gct ggc ggt ggt aag cca gag atg tac gcc tcc gat cta gtg<br>Ile Pro Ala Gly Gly Gly Lys Pro Glu Met Tyr Ala Ser Asp Leu Val<br>130     135     140 | | 432 |
| acg ctg ctc aaa tca cgc cac gat ttt gat att tcc gtg gcc gcc ttc<br>Thr Leu Leu Lys Ser Arg His Asp Phe Asp Ile Ser Val Ala Ala Phe<br>145     150     155     160 | | 480 |
| cct gaa gtg cac cct gaa gcc aaa agc gcg caa gcg gac ctg ctc aat<br>Pro Glu Val His Pro Glu Ala Lys Ser Ala Gln Ala Asp Leu Leu Asn<br>     165     170     175 | | 528 |
| tta aaa cgt aaa gtc gat gca ggt gcg aat cgt gcc atc acg cag ttt<br>Leu Lys Arg Lys Val Asp Ala Gly Ala Asn Arg Ala Ile Thr Gln Phe<br>   180     185     190 | | 576 |
| ttc ttt gat gta gaa agc tac ctg cgt ttt cgc gat cgc tgt gtg gcc<br>Phe Phe Asp Val Glu Ser Tyr Leu Arg Phe Arg Asp Arg Cys Val Ala<br>     195     200     205 | | 624 |
| gct ggg att gac gta gaa atc gtg cct ggc att ctg ccg gtt tct aac<br>Ala Gly Ile Asp Val Glu Ile Val Pro Gly Ile Leu Pro Val Ser Asn<br>210     215     220 | | 672 |
| ttt aaa caa gcg tcg cgc ttc gct gcg caa aac aac gtc aaa gtt ccg<br>Phe Lys Gln Ala Ser Arg Phe Ala Ala Gln Asn Asn Val Lys Val Pro<br>225     230     235     240 | | 720 |
| aat tgg atg gtg aag cag ttt gaa gga tta gaa gac gat cca gtg act<br>Asn Trp Met Val Lys Gln Phe Glu Gly Leu Glu Asp Asp Pro Val Thr<br>     245     250     255 | | 768 |
| cgc cag ttg gta ggt gca agc caa gcc att gat atg gtg cgc gtg ctg<br>Arg Gln Leu Val Gly Ala Ser Gln Ala Ile Asp Met Val Arg Val Leu<br>   260     265     270 | | 816 |
| tgc cgt gaa ggg gtg aag gat ttc cac ttc tac acc cta aat cgt gcc<br>Cys Arg Glu Gly Val Lys Asp Phe His Phe Tyr Thr Leu Asn Arg Ala<br>     275     280     285 | | 864 |
| gaa atg act tac gcg tta tgc cac acc tta ggc gtt cgc cca caa gct<br>Glu Met Thr Tyr Ala Leu Cys His Thr Leu Gly Val Arg Pro Gln Ala<br>290     295     300 | | 912 |
| taa | | 915 |

<210> SEQ ID NO 36
<211> LENGTH: 304
<212> TYPE: PRT
<213> ORGANISM: Vibrio cholerae

<400> SEQUENCE: 36

Val Thr Leu Gly His Arg Glu Tyr Lys Met Gly Tyr Thr His Ala Ser
1     5     10     15

His Ile Asp Ala Leu Asn Gln Asn Ile Ala Glu Leu Ser Asp Ile Asn
     20     25     30

Val Ser Phe Glu Phe Phe Pro Pro Ser Ser Pro Gln Met Glu Glu Thr

-continued

```
                    35                   40                    45
Leu Trp Gly Ser Val His Arg Leu Lys Thr Leu Gln Pro Lys Phe Val
 50                      55                   60

Ser Val Thr Tyr Gly Ala Asn Ser Gly Glu Arg Asp Arg Thr His Ser
 65                  70                   75                   80

Ile Ile Lys Ala Ile Lys Asp Gln Thr Gly Leu Ile Ala Ala Pro His
                     85                   90                   95

Leu Thr Cys Ile Asp Ala Thr Arg Asp Glu Leu Ile Gln Ile Ala Asp
                100                  105                  110

Asp Tyr Trp His Asn Gly Ile Gln Asn Ile Val Ala Leu Arg Gly Asp
                115                  120                  125

Ile Pro Ala Gly Gly Lys Pro Glu Met Tyr Ala Ser Asp Leu Val
130                 135                  140

Thr Leu Leu Lys Ser Arg His Asp Phe Asp Ile Ser Val Ala Ala Phe
145                 150                  155                  160

Pro Glu Val His Pro Glu Ala Lys Ser Ala Gln Ala Asp Leu Leu Asn
                165                  170                  175

Leu Lys Arg Lys Val Asp Ala Gly Ala Asn Arg Ala Ile Thr Gln Phe
                180                  185                  190

Phe Phe Asp Val Glu Ser Tyr Leu Arg Phe Arg Asp Arg Cys Val Ala
                195                  200                  205

Ala Gly Ile Asp Val Glu Ile Val Pro Gly Ile Leu Pro Val Ser Asn
                210                  215                  220

Phe Lys Gln Ala Ser Arg Phe Ala Ala Gln Asn Asn Val Lys Val Pro
225                 230                  235                  240

Asn Trp Met Val Lys Gln Phe Glu Gly Leu Glu Asp Asp Pro Val Thr
                    245                  250                  255

Arg Gln Leu Val Gly Ala Ser Gln Ala Ile Asp Met Val Arg Val Leu
                260                  265                  270

Cys Arg Glu Gly Val Lys Asp Phe His Phe Tyr Thr Leu Asn Arg Ala
                275                  280                  285

Glu Met Thr Tyr Ala Leu Cys His Thr Leu Gly Val Arg Pro Gln Ala
290                 295                  300
```

<210> SEQ ID NO 37
<211> LENGTH: 879
<212> TYPE: DNA
<213> ORGANISM: Haemophilus influenzae
<220> FEATURE:
<221> NAME/KEY: CDS
<222> LOCATION: (1)..(876)
<223> OTHER INFORMATION: RHI06620

<400> SEQUENCE: 37

```
atg agc tac gcg aaa gaa att gat aca tta aat caa cat att gca gat      48
Met Ser Tyr Ala Lys Glu Ile Asp Thr Leu Asn Gln His Ile Ala Asp
 1               5                  10                  15 ttt aat aaa aaa att aat gtc tcc ttt gaa ttt ttt cca cct aaa aac      96
Phe Asn Lys Lys Ile Asn Val Ser Phe Glu Phe Phe Pro Pro Lys Asn
                20                  25                  30 gaa aaa atg gaa acc ctt cta tgg gat tca att cat cgt tta aaa gta     144
Glu Lys Met Glu Thr Leu Leu Trp Asp Ser Ile His Arg Leu Lys Val
            35                  40                  45 tta aag cct aaa ttt gtg tca gtc act tac ggt gca aat tcg gga gaa     192
Leu Lys Pro Lys Phe Val Ser Val Thr Tyr Gly Ala Asn Ser Gly Glu
     50                  55                  60 cgt gac cgc act cac ggc att gtg aaa gcc att aaa caa gaa act ggc     240
```

```
                                                              -continued

Arg Asp Arg Thr His Gly Ile Val Lys Ala Ile Lys Gln Glu Thr Gly
 65              70                  75                  80 tta gaa gcc gca cca cat tta act gga att gat gcc aca cct gaa gaa    288
Leu Glu Ala Ala Pro His Leu Thr Gly Ile Asp Ala Thr Pro Glu Glu
                 85                  90                  95 tta aaa caa att gcg aga gat tat tgg gat agt ggt att cgc cgt att    336
Leu Lys Gln Ile Ala Arg Asp Tyr Trp Asp Ser Gly Ile Arg Arg Ile
            100                 105                 110 gtt gcg tta cgc ggt gac gaa cct aaa ggt tac gcg aaa aaa cca ttt    384
Val Ala Leu Arg Gly Asp Glu Pro Lys Gly Tyr Ala Lys Lys Pro Phe
        115                 120                 125 tat gcg tca gat ctt gtg gaa tta ctc cgt tct gtc gct gat ttt gat    432
Tyr Ala Ser Asp Leu Val Glu Leu Leu Arg Ser Val Ala Asp Phe Asp
    130                 135                 140 att tct gta gcc gct tat ccc gaa gtt cat cca gaa gca aaa tcc gca    480
Ile Ser Val Ala Ala Tyr Pro Glu Val His Pro Glu Ala Lys Ser Ala
145                 150                 155                 160 caa gca gac tta att aat tta aaa cgt aaa att gat gca ggt gca aac    528
Gln Ala Asp Leu Ile Asn Leu Lys Arg Lys Ile Asp Ala Gly Ala Asn
                165                 170                 175 cac gtc att aca caa ttt ttc ttt gat att gaa aac tac cta cgt ttt    576
His Val Ile Thr Gln Phe Phe Phe Asp Ile Glu Asn Tyr Leu Arg Phe
            180                 185                 190 cgt gat cgt tgt gca tca att ggt att gat act gaa atc gta ccc ggt    624
Arg Asp Arg Cys Ala Ser Ile Gly Ile Asp Thr Glu Ile Val Pro Gly
        195                 200                 205 att tta cct gtt act aat ttt aaa caa ctc caa aaa atg gca tca ttc    672
Ile Leu Pro Val Thr Asn Phe Lys Gln Leu Gln Lys Met Ala Ser Phe
    210                 215                 220 act aat gtg aaa att cca gcg tgg tta gtt aaa gcc tat gat ggt ttg    720
Thr Asn Val Lys Ile Pro Ala Trp Leu Val Lys Ala Tyr Asp Gly Leu
225                 230                 235                 240 gat aat gat cca act aca cgt aat ctt gtg gca gca agt gtt gca atg    768
Asp Asn Asp Pro Thr Thr Arg Asn Leu Val Ala Ala Ser Val Ala Met
                245                 250                 255 gat atg gta aaa att tta tct cgc gaa ggc gtg aat gac ttc cac ttt    816
Asp Met Val Lys Ile Leu Ser Arg Glu Gly Val Asn Asp Phe His Phe
            260                 265                 270 tat aca tta aat cgt agt gaa tta act tat gct atc tgt cat atg tta    864
Tyr Thr Leu Asn Arg Ser Glu Leu Thr Tyr Ala Ile Cys His Met Leu
        275                 280                 285 ggt gta aga cct taa                                                879
Gly Val Arg Pro
    290

<210> SEQ ID NO 38
<211> LENGTH: 292
<212> TYPE: PRT
<213> ORGANISM: Haemophilus influenzae

<400> SEQUENCE: 38

Met Ser Tyr Ala Lys Glu Ile Asp Thr Leu Asn Gln His Ile Ala Asp
 1               5                  10                  15

Phe Asn Lys Lys Ile Asn Val Ser Phe Glu Phe Pro Pro Lys Asn
            20                  25                  30

Glu Lys Met Glu Thr Leu Leu Trp Asp Ser Ile His Arg Leu Lys Val
        35                  40                  45

Leu Lys Pro Lys Phe Val Ser Val Thr Tyr Gly Ala Asn Ser Gly Glu
    50                  55                  60
```

```
Arg Asp Arg Thr His Gly Ile Val Lys Ala Ile Lys Gln Glu Thr Gly
 65                  70                  75                  80

Leu Glu Ala Ala Pro His Leu Thr Gly Ile Asp Ala Thr Pro Glu Glu
                 85                  90                  95

Leu Lys Gln Ile Ala Arg Asp Tyr Trp Asp Ser Gly Ile Arg Arg Ile
            100                 105                 110

Val Ala Leu Arg Gly Asp Glu Pro Lys Gly Tyr Ala Lys Lys Pro Phe
        115                 120                 125

Tyr Ala Ser Asp Leu Val Glu Leu Leu Arg Ser Val Ala Asp Phe Asp
    130                 135                 140

Ile Ser Val Ala Ala Tyr Pro Glu Val His Pro Glu Ala Lys Ser Ala
145                 150                 155                 160

Gln Ala Asp Leu Ile Asn Leu Lys Arg Lys Ile Asp Ala Gly Ala Asn
                165                 170                 175

His Val Ile Thr Gln Phe Phe Phe Asp Ile Glu Asn Tyr Leu Arg Phe
            180                 185                 190

Arg Asp Arg Cys Ala Ser Ile Gly Ile Asp Thr Glu Ile Val Pro Gly
        195                 200                 205

Ile Leu Pro Val Thr Asn Phe Lys Gln Leu Gln Lys Met Ala Ser Phe
    210                 215                 220

Thr Asn Val Lys Ile Pro Ala Trp Leu Val Lys Ala Tyr Asp Gly Leu
225                 230                 235                 240

Asp Asn Asp Pro Thr Thr Arg Asn Leu Val Ala Ala Ser Val Ala Met
                245                 250                 255

Asp Met Val Lys Ile Leu Ser Arg Glu Gly Val Asn Asp Phe His Phe
            260                 265                 270

Tyr Thr Leu Asn Arg Ser Glu Leu Thr Tyr Ala Ile Cys His Met Leu
        275                 280                 285

Gly Val Arg Pro
    290

<210> SEQ ID NO 39
<211> LENGTH: 945
<212> TYPE: DNA
<213> ORGANISM: Caulobacter crescentus
<220> FEATURE:
<221> NAME/KEY: CDS
<222> LOCATION: (1)..(942)
<223> OTHER INFORMATION: RCO02274

<400> SEQUENCE: 39 atg acc ctt ccg ccc acc cgc cgc gtg atc ggt ccc gtc gcc cga gcc      48
Met Thr Leu Pro Pro Thr Arg Arg Val Ile Gly Pro Val Ala Arg Ala
  1               5                  10                  15 ggc gag cgg acc ggc cgt ccg cgc gtg tcg ttc gag ttc ttc ccg ccc      96
Gly Glu Arg Thr Gly Arg Pro Arg Val Ser Phe Glu Phe Phe Pro Pro
             20                  25                  30 aag act ccg cag atg gaa gag agc ctg tgg cag gcg atc aca cgc ctg     144
Lys Thr Pro Gln Met Glu Glu Ser Leu Trp Gln Ala Ile Thr Arg Leu
         35                  40                  45 gcg ccg ctg gat ccg gcc ttc gtc tcg gtg acc tat ggc gcg ggc ggc     192
Ala Pro Leu Asp Pro Ala Phe Val Ser Val Thr Tyr Gly Ala Gly Gly
     50                  55                  60 tcc acc cgc gag cgc acc cac cgc acc gtc aag cgg atc ctg gac gag     240
Ser Thr Arg Glu Arg Thr His Arg Thr Val Lys Arg Ile Leu Asp Glu
 65                  70                  75                  80 acc agc ctc aag ccc gcc gcg cac ctg acc tgc gtc ggc gcc agt cgc     288
Thr Ser Leu Lys Pro Ala Ala His Leu Thr Cys Val Gly Ala Ser Arg
```

-continued

```
                85                   90                   95
gaa gag gtc gat gag gtc att cgc gag tac tgg gag acc ggg gtc cgt    336
Glu Glu Val Asp Glu Val Ile Arg Glu Tyr Trp Glu Thr Gly Val Arg
            100                 105                 110 cac atc gtt tcg ctg cgg ggc gat ccg ccg ccc ggc gag ggc ggc atc    384
His Ile Val Ser Leu Arg Gly Asp Pro Pro Pro Gly Glu Gly Gly Ile
        115                 120                 125 ggc ggg gtc tat gtg ccg cgc gcc gac ggc tac gcc aac gcc aca gag    432
Gly Gly Val Tyr Val Pro Arg Ala Asp Gly Tyr Ala Asn Ala Thr Glu
    130                 135                 140 ttg acc aag gcc gtg cgc gcg atc gcg ccg ttc gag gtg ctg gtc ggg    480
Leu Thr Lys Ala Val Arg Ala Ile Ala Pro Phe Glu Val Leu Val Gly
145                 150                 155                 160 gtc tat ccc gag aag cat ccc gag agc ccc tcg ttg gag cac gac atc    528
Val Tyr Pro Glu Lys His Pro Glu Ser Pro Ser Leu Glu His Asp Ile
                165                 170                 175 gac gtc ttg aag cag aag gtc gac gcc ggc gcg acg ctg ggg atc agc    576
Asp Val Leu Lys Gln Lys Val Asp Ala Gly Ala Thr Leu Gly Ile Ser
            180                 185                 190 cag ttc ttc ttc gac ctc gac gcc ttc ctg cgc ttc gtc gac aag gtg    624
Gln Phe Phe Phe Asp Leu Asp Ala Phe Leu Arg Phe Val Asp Lys Val
        195                 200                 205 cgc gcg gcg ggc atc acc att ccg atc gtg ccg ggg atc atg ccg gtg    672
Arg Ala Ala Gly Ile Thr Ile Pro Ile Val Pro Gly Ile Met Pro Val
    210                 215                 220 acc aat ttc gcg ggc ttg aag aag atg gcc gcc gcc tgc cag acg gcc    720
Thr Asn Phe Ala Gly Leu Lys Lys Met Ala Ala Ala Cys Gln Thr Ala
225                 230                 235                 240 atc ccg tcc tgg ctg ggg aac ctg ttc gac ggg ctg gag aac gac gcg    768
Ile Pro Ser Trp Leu Gly Asn Leu Phe Asp Gly Leu Glu Asn Asp Ala
                245                 250                 255 gag acc cgc cgc ctg atc gcc tgt tcg gtg gcc gcc gag atg tgc gcc    816
Glu Thr Arg Arg Leu Ile Ala Cys Ser Val Ala Ala Glu Met Cys Ala
            260                 265                 270 aag ctg cag gaa cag ggt ttc gag gac ttc cac ttc tac acc ctg aac    864
Lys Leu Gln Glu Gln Gly Phe Glu Asp Phe His Phe Tyr Thr Leu Asn
        275                 280                 285 cgg gcc gat ctc gtt tac gcc atc tgc cgt gtg ctg ggc gtg cgc gag    912
Arg Ala Asp Leu Val Tyr Ala Ile Cys Arg Val Leu Gly Val Arg Glu
    290                 295                 300 atc tcg ccc gcc gct tcg gag gtc gcc gca tga                        945
Ile Ser Pro Ala Ala Ser Glu Val Ala Ala
305                 310
```

<210> SEQ ID NO 40
<211> LENGTH: 314
<212> TYPE: PRT
<213> ORGANISM: Caulobacter crescentus

<400> SEQUENCE: 40

```
Met Thr Leu Pro Pro Thr Arg Arg Val Ile Gly Pro Val Ala Arg Ala
 1               5                  10                  15

Gly Glu Arg Thr Gly Arg Pro Arg Val Ser Phe Glu Phe Pro Pro
            20                  25                  30

Lys Thr Pro Gln Met Glu Glu Ser Leu Trp Gln Ala Ile Thr Arg Leu
        35                  40                  45

Ala Pro Leu Asp Pro Ala Phe Val Ser Val Thr Tyr Gly Ala Gly Gly
    50                  55                  60

Ser Thr Arg Glu Arg Thr His Arg Thr Val Lys Arg Ile Leu Asp Glu
```

-continued

```
                65                  70                  75                  80
Thr Ser Leu Lys Pro Ala Ala His Leu Thr Cys Val Gly Ala Ser Arg
                        85                  90                  95
Glu Glu Val Asp Glu Val Ile Arg Glu Tyr Trp Glu Thr Gly Val Arg
                100                 105                 110
His Ile Val Ser Leu Arg Gly Asp Pro Pro Gly Glu Gly Gly Ile
            115                 120                 125
Gly Gly Val Tyr Val Pro Arg Ala Asp Gly Tyr Ala Asn Ala Thr Glu
        130                 135                 140
Leu Thr Lys Ala Val Arg Ala Ile Ala Pro Phe Glu Val Leu Val Gly
145                 150                 155                 160
Val Tyr Pro Glu Lys His Pro Glu Ser Pro Ser Leu Glu His Asp Ile
                165                 170                 175
Asp Val Leu Lys Gln Lys Val Asp Ala Gly Ala Thr Leu Gly Ile Ser
                180                 185                 190
Gln Phe Phe Phe Asp Leu Asp Ala Phe Leu Arg Phe Val Asp Lys Val
            195                 200                 205
Arg Ala Ala Gly Ile Thr Ile Pro Ile Val Pro Gly Ile Met Pro Val
        210                 215                 220
Thr Asn Phe Ala Gly Leu Lys Lys Met Ala Ala Cys Gln Thr Ala
225                 230                 235                 240
Ile Pro Ser Trp Leu Gly Asn Leu Phe Asp Gly Leu Glu Asn Asp Ala
                245                 250                 255
Glu Thr Arg Arg Leu Ile Ala Cys Ser Val Ala Ala Glu Met Cys Ala
                260                 265                 270
Lys Leu Gln Glu Gln Gly Phe Glu Asp Phe His Phe Tyr Thr Leu Asn
            275                 280                 285
Arg Ala Asp Leu Val Tyr Ala Ile Cys Arg Val Leu Gly Val Arg Glu
        290                 295                 300
Ile Ser Pro Ala Ala Ser Glu Val Ala Ala
305                 310
```

<210> SEQ ID NO 41
<211> LENGTH: 885
<212> TYPE: DNA
<213> ORGANISM: Actinobacillus actinomycetemcomitans
<220> FEATURE:
<221> NAME/KEY: CDS
<222> LOCATION: (1)..(882)
<223> OTHER INFORMATION: RAB00260

<400> SEQUENCE: 41

```
atg agt tac gca aaa gaa att gat aat cta aat caa cat tta gct gat     48
Met Ser Tyr Ala Lys Glu Ile Asp Asn Leu Asn Gln His Leu Ala Asp
  1               5                  10                  15 tta aac ggc aaa att aat gtc tct ttt gaa ttt ttc ccg ccg aaa agt     96
Leu Asn Gly Lys Ile Asn Val Ser Phe Glu Phe Phe Pro Pro Lys Ser
                 20                  25                  30 gaa aaa atg gaa aat ctt ctg tgg gaa tcc atc cat cgc tta aaa gtg    144
Glu Lys Met Glu Asn Leu Leu Trp Glu Ser Ile His Arg Leu Lys Val
             35                  40                  45 cta aaa ccg aaa ttt gta tcc gtg act tac ggc gcc aat tcc ggc gag    192
Leu Lys Pro Lys Phe Val Ser Val Thr Tyr Gly Ala Asn Ser Gly Glu
         50                  55                  60 cgt gaa cgc act cac ggg gtg gtg aaa cgc att aag cag gaa acc ggt    240
Arg Glu Arg Thr His Gly Val Val Lys Arg Ile Lys Gln Glu Thr Gly
 65                  70                  75                  80
```

```
ctg gaa gct gcg ccg cat tta acc ggt att gac gct acc tcg gac gaa   288
Leu Glu Ala Ala Pro His Leu Thr Gly Ile Asp Ala Thr Ser Asp Glu
             85                  90                  95 ttg cgt cgc att gcc aaa ggt tat tgg gat agc ggc att cgt cgc att   336
Leu Arg Arg Ile Ala Lys Gly Tyr Trp Asp Ser Gly Ile Arg Arg Ile
        100                 105                 110 gtg gca ctg cgc ggt gac gag ccg aaa ggc tac gag aaa aaa cca ttt   384
Val Ala Leu Arg Gly Asp Glu Pro Lys Gly Tyr Glu Lys Lys Pro Phe
    115                 120                 125 tat gcc gcc gat tta gta gca tta tta cgt gac gta tca gat ttt gat   432
Tyr Ala Ala Asp Leu Val Ala Leu Leu Arg Asp Val Ser Asp Phe Asp
130                 135                 140 att tcc gtg gcg gca tac cct gag gtt cat ccg gaa gcc aaa tcg gcg   480
Ile Ser Val Ala Ala Tyr Pro Glu Val His Pro Glu Ala Lys Ser Ala
145                 150                 155                 160 caa gcg gat tta att aat tta aaa cgt aaa att gat gcc ggt gcc aat   528
Gln Ala Asp Leu Ile Asn Leu Lys Arg Lys Ile Asp Ala Gly Ala Asn
                165                 170                 175 cat gtg atc aca caa ttc ttt ttc gat att gac agc tat ctg cgg ttc   576
His Val Ile Thr Gln Phe Phe Phe Asp Ile Asp Ser Tyr Leu Arg Phe
            180                 185                 190 cgc gat cgc tgc gcg tct atc ggt att gat gca gaa atc gtg ccg ggg   624
Arg Asp Arg Cys Ala Ser Ile Gly Ile Asp Ala Glu Ile Val Pro Gly
        195                 200                 205 att ctg ccg gtg acc aac ttc aaa caa tta caa aaa atg gca gca atc   672
Ile Leu Pro Val Thr Asn Phe Lys Gln Leu Gln Lys Met Ala Ala Ile
    210                 215                 220 act aat gtg aaa att cca gct tgg atg agc aaa atg tat gaa ggc ttg   720
Thr Asn Val Lys Ile Pro Ala Trp Met Ser Lys Met Tyr Glu Gly Leu
225                 230                 235                 240 gat gat gac caa acc acc cgc aat ctg gtg gcg gcg agc atc gcc atg   768
Asp Asp Asp Gln Thr Thr Arg Asn Leu Val Ala Ala Ser Ile Ala Met
                245                 250                 255 gac atg gtg cgt gta ctg tcc cgc gaa ggg gta aaa gac ttt cat ttc   816
Asp Met Val Arg Val Leu Ser Arg Glu Gly Val Lys Asp Phe His Phe
            260                 265                 270 tac acc ctg aat cgc agt gaa ctc acc tat gct att tgc cac acg tta   864
Tyr Thr Leu Asn Arg Ser Glu Leu Thr Tyr Ala Ile Cys His Thr Leu
        275                 280                 285 ggc att cgt cca agt ttg taa                                       885
Gly Ile Arg Pro Ser Leu
    290
```

<210> SEQ ID NO 42
<211> LENGTH: 294
<212> TYPE: PRT
<213> ORGANISM: Actinobacillus actinomycetemcomitans

<400> SEQUENCE: 42

```
Met Ser Tyr Ala Lys Glu Ile Asp Asn Leu Asn Gln His Leu Ala Asp
 1               5                  10                  15

Leu Asn Gly Lys Ile Asn Val Ser Phe Glu Phe Pro Pro Lys Ser
            20                  25                  30

Glu Lys Met Glu Asn Leu Leu Trp Glu Ser Ile His Arg Leu Lys Val
        35                  40                  45

Leu Lys Pro Lys Phe Val Ser Val Thr Tyr Gly Ala Asn Ser Gly Glu
    50                  55                  60

Arg Glu Arg Thr His Gly Val Val Lys Arg Ile Lys Gln Glu Thr Gly
65                  70                  75                  80
```

```
Leu Glu Ala Ala Pro His Leu Thr Gly Ile Asp Ala Thr Ser Asp Glu
                85                  90                  95

Leu Arg Arg Ile Ala Lys Gly Tyr Trp Asp Ser Gly Ile Arg Arg Ile
            100                 105                 110

Val Ala Leu Arg Gly Asp Glu Pro Lys Gly Tyr Glu Lys Lys Pro Phe
            115                 120                 125

Tyr Ala Ala Asp Leu Val Ala Leu Leu Arg Asp Val Ser Asp Phe Asp
            130                 135                 140

Ile Ser Val Ala Ala Tyr Pro Glu Val His Pro Glu Ala Lys Ser Ala
145                 150                 155                 160

Gln Ala Asp Leu Ile Asn Leu Lys Arg Lys Ile Asp Ala Gly Ala Asn
                165                 170                 175

His Val Ile Thr Gln Phe Phe Phe Asp Ile Asp Ser Tyr Leu Arg Phe
            180                 185                 190

Arg Asp Arg Cys Ala Ser Ile Gly Ile Asp Ala Glu Ile Val Pro Gly
            195                 200                 205

Ile Leu Pro Val Thr Asn Phe Lys Gln Leu Gln Lys Met Ala Ala Ile
210                 215                 220

Thr Asn Val Lys Ile Pro Ala Trp Met Ser Lys Met Tyr Glu Gly Leu
225                 230                 235                 240

Asp Asp Asp Gln Thr Thr Arg Asn Leu Val Ala Ala Ser Ile Ala Met
            245                 250                 255

Asp Met Val Arg Val Leu Ser Arg Glu Gly Val Lys Asp Phe His Phe
            260                 265                 270

Tyr Thr Leu Asn Arg Ser Glu Leu Thr Tyr Ala Ile Cys His Thr Leu
            275                 280                 285

Gly Ile Arg Pro Ser Leu
            290

<210> SEQ ID NO 43
<211> LENGTH: 867
<212> TYPE: DNA
<213> ORGANISM: Rhodobacter
<220> FEATURE:
<221> NAME/KEY: CDS
<222> LOCATION: (1)..(864)
<223> OTHER INFORMATION: RRC03981

<400> SEQUENCE: 43 atg acc acg ccg cat gtc agc ttt gaa ttc ttc ccg ccg cag acg ctc      48
Met Thr Thr Pro His Val Ser Phe Glu Phe Phe Pro Pro Gln Thr Leu
  1               5                  10                  15 gac gcc tcg ttc cgg ctg tgg gag acg gcg cag gtt ctg gcg ccg ctc      96
Asp Ala Ser Phe Arg Leu Trp Glu Thr Ala Gln Val Leu Ala Pro Leu
             20                  25                  30 aag ccc ggc ttc gtc tcg gtc acc tat ggc gcg ggc ggc acc acc cgc     144
Lys Pro Gly Phe Val Ser Val Thr Tyr Gly Ala Gly Gly Thr Thr Arg
         35                  40                  45 aag ctg acg cat gag gcc gtg gcg gcg atc cac aag aat tac ggc ctg     192
Lys Leu Thr His Glu Ala Val Ala Ala Ile His Lys Asn Tyr Gly Leu
     50                  55                  60 aac gtc gcc gcg cat ctg acc tgc gtc gat gcg acc cgg gcc gaa acg     240
Asn Val Ala Ala His Leu Thr Cys Val Asp Ala Thr Arg Ala Glu Thr
 65                  70                  75                  80 caa gag atc atc gac gcc tat gcc gag gct ggc gtc acc gag att gtc     288
Gln Glu Ile Ile Asp Ala Tyr Ala Glu Ala Gly Val Thr Glu Ile Val
                 85                  90                  95 gcg ctg cgc ggt gat ccg ccg aaa ggc gcc gcc cgc ttc acg ccg cat     336
```

```
Ala Leu Arg Gly Asp Pro Pro Lys Gly Ala Ala Arg Phe Thr Pro His
            100                 105                 110 ccg gac ggg ttt gcc tcc tcg gtg gac ctc atc gaa tgg ctg gcg cgg      384
Pro Asp Gly Phe Ala Ser Ser Val Asp Leu Ile Glu Trp Leu Ala Arg
        115                 120                 125 gac ggc cgc ttc acg ctg cgc tgc ggc gcc tat ccg gaa ccg cat ccg      432
Asp Gly Arg Phe Thr Leu Arg Cys Gly Ala Tyr Pro Glu Pro His Pro
130                 135                 140 gaa gcc gcc gac acg ctg gcc gac gtg cgc tgg ctg aaa cgc aaa tgc      480
Glu Ala Ala Asp Thr Leu Ala Asp Val Arg Trp Leu Lys Arg Lys Cys
145                 150                 155                 160 gag gcg ggg gcg acc tcg gcg atc acg caa ttc ttc ttt gaa gcc gag      528
Glu Ala Gly Ala Thr Ser Ala Ile Thr Gln Phe Phe Phe Glu Ala Glu
                165                 170                 175 acc ttc ttc cgc ttc cgc gac gcc tgc gtg aag gaa ggg atc acc gcc      576
Thr Phe Phe Arg Phe Arg Asp Ala Cys Val Lys Glu Gly Ile Thr Ala
            180                 185                 190 aag atc atc ccg ggc atc ctg ccg atc cag tcc tgg aaa ggc gcc aag      624
Lys Ile Ile Pro Gly Ile Leu Pro Ile Gln Ser Trp Lys Gly Ala Lys
        195                 200                 205 agc ttt gcg cag cgc tgc ggc acc tcg atc ccg acc tgg gtc gaa gag      672
Ser Phe Ala Gln Arg Cys Gly Thr Ser Ile Pro Thr Trp Val Glu Glu
210                 215                 220 gcc ttt gac cat gcg atc cgc gac gac cgc gaa cag ctg ctg gcc acg      720
Ala Phe Asp His Ala Ile Arg Asp Asp Arg Glu Gln Leu Leu Ala Thr
225                 230                 235                 240 gcg ctg tgc acg gag ctc tgc gac aac ctg atc gcg ggc ggg gtg gag      768
Ala Leu Cys Thr Glu Leu Cys Asp Asn Leu Ile Ala Gly Gly Val Glu
                245                 250                 255 gat ctg cat ttc tac acg ctg aac cgg ccg cag atg acc cgc gat gtc      816
Asp Leu His Phe Tyr Thr Leu Asn Arg Pro Gln Met Thr Arg Asp Val
            260                 265                 270 tgc cat gcg ctg ggc gtc aac ccg ggt gtg gtg ctg gaa aac gtc gcc      864
Cys His Ala Leu Gly Val Asn Pro Gly Val Val Leu Glu Asn Val Ala
        275                 280                 285 tga                                                                   867

<210> SEQ ID NO 44
<211> LENGTH: 288
<212> TYPE: PRT
<213> ORGANISM: Rhodobacter

<400> SEQUENCE: 44

Met Thr Thr Pro His Val Ser Phe Glu Phe Pro Pro Gln Thr Leu
1               5                   10                  15

Asp Ala Ser Phe Arg Leu Trp Glu Thr Ala Gln Val Leu Ala Pro Leu
            20                  25                  30

Lys Pro Gly Phe Val Ser Val Thr Tyr Gly Ala Gly Gly Thr Thr Arg
        35                  40                  45

Lys Leu Thr His Glu Ala Val Ala Ala Ile His Lys Asn Tyr Gly Leu
    50                  55                  60

Asn Val Ala Ala His Leu Thr Cys Val Asp Ala Thr Arg Ala Glu Thr
65                  70                  75                  80

Gln Glu Ile Ile Asp Ala Tyr Ala Glu Ala Gly Val Thr Glu Ile Val
                85                  90                  95

Ala Leu Arg Gly Asp Pro Pro Lys Gly Ala Ala Arg Phe Thr Pro His
            100                 105                 110

Pro Asp Gly Phe Ala Ser Ser Val Asp Leu Ile Glu Trp Leu Ala Arg
```

-continued

```
                115                 120                 125
Asp Gly Arg Phe Thr Leu Arg Cys Gly Ala Tyr Pro Glu Pro His Pro
    130                 135                 140

Glu Ala Ala Asp Thr Leu Ala Asp Val Arg Trp Leu Lys Arg Lys Cys
145                 150                 155                 160

Glu Ala Gly Ala Thr Ser Ala Ile Thr Gln Phe Phe Glu Ala Glu
                165                 170                 175

Thr Phe Phe Arg Phe Arg Asp Ala Cys Val Lys Glu Gly Ile Thr Ala
                180                 185                 190

Lys Ile Ile Pro Gly Ile Leu Pro Ile Gln Ser Trp Lys Gly Ala Lys
                195                 200                 205

Ser Phe Ala Gln Arg Cys Gly Thr Ser Ile Pro Thr Trp Val Glu Glu
    210                 215                 220

Ala Phe Asp His Ala Ile Arg Asp Asp Arg Glu Gln Leu Leu Ala Thr
225                 230                 235                 240

Ala Leu Cys Thr Glu Leu Cys Asp Asn Leu Ile Ala Gly Gly Val Glu
                245                 250                 255

Asp Leu His Phe Tyr Thr Leu Asn Arg Pro Gln Met Thr Arg Asp Val
                260                 265                 270

Cys His Ala Leu Gly Val Asn Pro Gly Val Val Leu Glu Asn Val Ala
                275                 280                 285
```

<210> SEQ ID NO 45
<211> LENGTH: 879
<212> TYPE: DNA
<213> ORGANISM: Neisseria meningitidis ser. A
<220> FEATURE:
<221> NAME/KEY: CDS
<222> LOCATION: (1)..(876)
<223> OTHER INFORMATION: RNM00812

<400> SEQUENCE: 45

```
atg aat tac gca aaa gaa atc aat gcg tta aat aac agc ctt tcc gat      48
Met Asn Tyr Ala Lys Glu Ile Asn Ala Leu Asn Asn Ser Leu Ser Asp
  1               5                  10                  15 ttg aaa ggc gac atc aac gtt tcg ttt gaa ttt ttt cca ccg aaa aac      96
Leu Lys Gly Asp Ile Asn Val Ser Phe Glu Phe Phe Pro Pro Lys Asn
                 20                  25                  30 gag caa atg gaa acg atg ctg tgg gat tcc atc cac cgt ctg caa acc     144
Glu Gln Met Glu Thr Met Leu Trp Asp Ser Ile His Arg Leu Gln Thr
             35                  40                  45 ctg cat ccc aag ttc gta tcc gta acc tac ggc gca aac tcc ggc gaa     192
Leu His Pro Lys Phe Val Ser Val Thr Tyr Gly Ala Asn Ser Gly Glu
         50                  55                  60 cgc gac cgc acg cac ggc atc gtc aaa cgc atc aaa cag gaa acc ggc     240
Arg Asp Arg Thr His Gly Ile Val Lys Arg Ile Lys Gln Glu Thr Gly
 65                  70                  75                  80 ttg gaa gca gca ccg cac ctg acc ggc atc gac gca tcc ccc gac gaa     288
Leu Glu Ala Ala Pro His Leu Thr Gly Ile Asp Ala Ser Pro Asp Glu
                 85                  90                  95 ttg cgc caa atc gcc aaa gac tat tgg gac agc ggc atc cgc cgc att     336
Leu Arg Gln Ile Ala Lys Asp Tyr Trp Asp Ser Gly Ile Arg Arg Ile
            100                 105                 110 gtc gcc ctg cgt ggc gac gag ccg ccc ggt tat gag aaa aaa ccg ttt     384
Val Ala Leu Arg Gly Asp Glu Pro Pro Gly Tyr Glu Lys Lys Pro Phe
        115                 120                 125 tac gcc gaa gac ttg gtt aag cta tta cgc tcc gtc gcc gac ttc gac     432
Tyr Ala Glu Asp Leu Val Lys Leu Leu Arg Ser Val Ala Asp Phe Asp
    130                 135                 140
```

```
atc tct gtg gcg gca tat ccc gaa gtg cat ccc gaa gcc aaa tcc gca    480
Ile Ser Val Ala Ala Tyr Pro Glu Val His Pro Glu Ala Lys Ser Ala
145                 150                 155                 160 caa gcc gat ctg att aat ctg aag cgc aaa atc gat gcg ggt gca aac    528
Gln Ala Asp Leu Ile Asn Leu Lys Arg Lys Ile Asp Ala Gly Ala Asn
                165                 170                 175 cac gtc atc acc caa ttt ttc ttt gac gta gaa cgc tac ctg cgc ttc    576
His Val Ile Thr Gln Phe Phe Phe Asp Val Glu Arg Tyr Leu Arg Phe
            180                 185                 190 cgc gac cgc tgc gtg atg ttg ggt atc gat gtg gaa atc gtc cct ggt    624
Arg Asp Arg Cys Val Met Leu Gly Ile Asp Val Glu Ile Val Pro Gly
        195                 200                 205 att ttg cct gtt acc aac ttc aag cag ctc ggc aaa atg gcg caa gta    672
Ile Leu Pro Val Thr Asn Phe Lys Gln Leu Gly Lys Met Ala Gln Val
    210                 215                 220 acc aac gtc aaa atc cca agc tgg ctg tcg caa atg tat gaa ggt ttg    720
Thr Asn Val Lys Ile Pro Ser Trp Leu Ser Gln Met Tyr Glu Gly Leu
225                 230                 235                 240 gac gac gac caa ggc acg cgc aac ctc gtc gcc gcc agt atc gcc atc    768
Asp Asp Asp Gln Gly Thr Arg Asn Leu Val Ala Ala Ser Ile Ala Ile
                245                 250                 255 gat atg gtc aaa gtc ctg tcc cgc gaa ggc gtg aaa gat ttc cac ttc    816
Asp Met Val Lys Val Leu Ser Arg Glu Gly Val Lys Asp Phe His Phe
            260                 265                 270 tac acg ctc aac cgc agc gag ctg act tac gcc atc tgc cat att tta    864
Tyr Thr Leu Asn Arg Ser Glu Leu Thr Tyr Ala Ile Cys His Ile Leu
        275                 280                 285 ggc gtg cgc cct taa                                                879
Gly Val Arg Pro
    290

<210> SEQ ID NO 46
<211> LENGTH: 292
<212> TYPE: PRT
<213> ORGANISM: Neisseria meningitidis ser. A

<400> SEQUENCE: 46

Met Asn Tyr Ala Lys Glu Ile Asn Ala Leu Asn Asn Ser Leu Ser Asp
1               5                   10                  15

Leu Lys Gly Asp Ile Asn Val Ser Phe Glu Phe Pro Pro Lys Asn
            20                  25                  30

Glu Gln Met Glu Thr Met Leu Trp Asp Ser Ile His Arg Leu Gln Thr
        35                  40                  45

Leu His Pro Lys Phe Val Ser Val Thr Tyr Gly Ala Asn Ser Gly Glu
    50                  55                  60

Arg Asp Arg Thr His Gly Ile Val Lys Arg Ile Lys Gln Glu Thr Gly
65                  70                  75                  80

Leu Glu Ala Ala Pro His Leu Thr Gly Ile Asp Ala Ser Pro Asp Glu
                85                  90                  95

Leu Arg Gln Ile Ala Lys Asp Tyr Trp Asp Ser Gly Ile Arg Arg Ile
            100                 105                 110

Val Ala Leu Arg Gly Asp Glu Pro Pro Gly Tyr Glu Lys Lys Pro Phe
        115                 120                 125

Tyr Ala Glu Asp Leu Val Lys Leu Leu Arg Ser Val Ala Asp Phe Asp
    130                 135                 140

Ile Ser Val Ala Ala Tyr Pro Glu Val His Pro Glu Ala Lys Ser Ala
145                 150                 155                 160
```

-continued

```
Gln Ala Asp Leu Ile Asn Leu Lys Arg Lys Ile Asp Ala Gly Ala Asn
                165                 170                 175

His Val Ile Thr Gln Phe Phe Phe Asp Val Glu Arg Tyr Leu Arg Phe
            180                 185                 190

Arg Asp Arg Cys Val Met Leu Gly Ile Asp Val Glu Ile Val Pro Gly
        195                 200                 205

Ile Leu Pro Val Thr Asn Phe Lys Gln Leu Gly Lys Met Ala Gln Val
    210                 215                 220

Thr Asn Val Lys Ile Pro Ser Trp Leu Ser Gln Met Tyr Glu Gly Leu
225                 230                 235                 240

Asp Asp Gln Gly Thr Arg Asn Leu Val Ala Ala Ser Ile Ala Ile
                245                 250                 255

Asp Met Val Lys Val Leu Ser Arg Glu Gly Val Lys Asp Phe His Phe
            260                 265                 270

Tyr Thr Leu Asn Arg Ser Glu Leu Thr Tyr Ala Ile Cys His Ile Leu
        275                 280                 285

Gly Val Arg Pro
290
```

<210> SEQ ID NO 47
<211> LENGTH: 849
<212> TYPE: DNA
<213> ORGANISM: Campylobacter jejuni
<220> FEATURE:
<221> NAME/KEY: CDS
<222> LOCATION: (1)..(846)
<223> OTHER INFORMATION: RCJ02911

<400> SEQUENCE: 47

```
atg tgt agt ttt tct ttt gaa gtt ttt cca cca aga aag gat gaa aat    48
Met Cys Ser Phe Ser Phe Glu Val Phe Pro Pro Arg Lys Asp Glu Asn
  1               5                  10                  15 atc aaa aat ctt cat gct atc tta gat gat tta ggg caa tta agc cct    96
Ile Lys Asn Leu His Ala Ile Leu Asp Asp Leu Gly Gln Leu Ser Pro
             20                  25                  30 aat ttt atc agc gta acc ttt gga gct gga ggc tct att aac tca caa   144
Asn Phe Ile Ser Val Thr Phe Gly Ala Gly Gly Ser Ile Asn Ser Gln
         35                  40                  45 aat act tta gaa gtt gca agc tta atc cag gaa gaa tat caa att cct   192
Asn Thr Leu Glu Val Ala Ser Leu Ile Gln Glu Glu Tyr Gln Ile Pro
     50                  55                  60 agc ata gta cat tta cct tgc atc cat tct agt aaa gaa aaa atc act   240
Ser Ile Val His Leu Pro Cys Ile His Ser Ser Lys Glu Lys Ile Thr
 65                  70                  75                  80 cag ata ctt caa aaa tgc aaa gaa aaa aat ctt aat caa att ctt gcc   288
Gln Ile Leu Gln Lys Cys Lys Glu Lys Asn Leu Asn Gln Ile Leu Ala
                 85                  90                  95 cta aga ggc gat ata tgt gaa aat tta aaa aaa agc aaa gat ttt tct   336
Leu Arg Gly Asp Ile Cys Glu Asn Leu Lys Lys Ser Lys Asp Phe Ser
            100                 105                 110 tat gct agt gat tta att tct ttt ata aaa aaa caa gaa tac ttt gaa   384
Tyr Ala Ser Asp Leu Ile Ser Phe Ile Lys Lys Gln Glu Tyr Phe Glu
        115                 120                 125 att tat gcc gca tgc tat ccc gaa aaa cat aat gaa tct aaa aat ttc   432
Ile Tyr Ala Ala Cys Tyr Pro Glu Lys His Asn Glu Ser Lys Asn Phe
    130                 135                 140 atc gag gat ata cac cat ctt aaa act aag gta aat gca gga aca gat   480
Ile Glu Asp Ile His His Leu Lys Thr Lys Val Asn Ala Gly Thr Asp
145                 150                 155                 160
```

-continued

```
aag ctc att act caa ctt ttt tac gat aat gaa gat ttt tat act ttt    528
Lys Leu Ile Thr Gln Leu Phe Tyr Asp Asn Glu Asp Phe Tyr Thr Phe
            165                 170                 175 aaa caa aat tgt gct tta gca gat att gac ata cct att tac gca ggt    576
Lys Gln Asn Cys Ala Leu Ala Asp Ile Asp Ile Pro Ile Tyr Ala Gly
        180                 185                 190 att atg cct att act aac aaa aga cag gtt tta aaa att tct caa ctt    624
Ile Met Pro Ile Thr Asn Lys Arg Gln Val Leu Lys Ile Ser Gln Leu
    195                 200                 205 tgc gga gct aaa atc cct cct aaa ttt gtt aaa att tta gaa aaa tat    672
Cys Gly Ala Lys Ile Pro Pro Lys Phe Val Lys Ile Leu Glu Lys Tyr
210                 215                 220 gaa aat aat act ttg gct tta gaa gat gca ggt atc gcg tat gct tgc    720
Glu Asn Asn Thr Leu Ala Leu Glu Asp Ala Gly Ile Ala Tyr Ala Cys
225                 230                 235                 240 gat caa att gtc gat tta atc aca agt ggt gta gat gga att cat ctt    768
Asp Gln Ile Val Asp Leu Ile Thr Ser Gly Val Asp Gly Ile His Leu
                245                 250                 255 tat act atg aat aaa tcc aaa gcg gct att aaa att tat gaa gct gta    816
Tyr Thr Met Asn Lys Ser Lys Ala Ala Ile Lys Ile Tyr Glu Ala Val
            260                 265                 270 aag cat ttg ctt aaa gaa gag ctt cat gct tag                        849
Lys His Leu Leu Lys Glu Glu Leu His Ala
        275                 280
```

<210> SEQ ID NO 48
<211> LENGTH: 282
<212> TYPE: PRT
<213> ORGANISM: Campylobacter jejuni

<400> SEQUENCE: 48

```
Met Cys Ser Phe Ser Phe Glu Val Phe Pro Pro Arg Lys Asp Glu Asn
 1               5                  10                  15

Ile Lys Asn Leu His Ala Ile Leu Asp Asp Leu Gly Gln Leu Ser Pro
            20                  25                  30

Asn Phe Ile Ser Val Thr Phe Gly Ala Gly Gly Ser Ile Asn Ser Gln
        35                  40                  45

Asn Thr Leu Glu Val Ala Ser Leu Ile Gln Glu Glu Tyr Gln Ile Pro
    50                  55                  60

Ser Ile Val His Leu Pro Cys Ile His Ser Ser Lys Glu Lys Ile Thr
65                  70                  75                  80

Gln Ile Leu Gln Lys Cys Lys Glu Lys Asn Leu Asn Gln Ile Leu Ala
                85                  90                  95

Leu Arg Gly Asp Ile Cys Glu Asn Leu Lys Lys Ser Lys Asp Phe Ser
            100                 105                 110

Tyr Ala Ser Asp Leu Ile Ser Phe Ile Lys Lys Gln Glu Tyr Phe Glu
        115                 120                 125

Ile Tyr Ala Ala Cys Tyr Pro Glu Lys His Asn Glu Ser Lys Asn Phe
    130                 135                 140

Ile Glu Asp Ile His His Leu Lys Thr Lys Val Asn Ala Gly Thr Asp
145                 150                 155                 160

Lys Leu Ile Thr Gln Leu Phe Tyr Asp Asn Glu Asp Phe Tyr Thr Phe
            165                 170                 175

Lys Gln Asn Cys Ala Leu Ala Asp Ile Asp Ile Pro Ile Tyr Ala Gly
        180                 185                 190

Ile Met Pro Ile Thr Asn Lys Arg Gln Val Leu Lys Ile Ser Gln Leu
    195                 200                 205
```

```
Cys Gly Ala Lys Ile Pro Pro Lys Phe Val Lys Ile Leu Glu Lys Tyr
        210                 215                 220

Glu Asn Asn Thr Leu Ala Leu Glu Asp Ala Gly Ile Ala Tyr Ala Cys
225                 230                 235                 240

Asp Gln Ile Val Asp Leu Ile Thr Ser Gly Val Asp Gly Ile His Leu
                245                 250                 255

Tyr Thr Met Asn Lys Ser Lys Ala Ala Ile Lys Ile Tyr Glu Ala Val
            260                 265                 270

Lys His Leu Leu Lys Glu Glu Leu His Ala
        275                 280
```

<210> SEQ ID NO 49
<211> LENGTH: 852
<212> TYPE: DNA
<213> ORGANISM: Lactococcus lactis
<220> FEATURE:
<221> NAME/KEY: CDS
<222> LOCATION: (1)..(849)
<223> OTHER INFORMATION: AAK05352

<400> SEQUENCE: 49

```
atg aca agt aat tcc aaa att ctt tct ttt gaa gtt ttt cca cct aca      48
Met Thr Ser Asn Ser Lys Ile Leu Ser Phe Glu Val Phe Pro Pro Thr
 1               5                  10                  15 act caa att gga agt acc aac ttg gta aag acc ttg gat agc cta aga      96
Thr Gln Ile Gly Ser Thr Asn Leu Val Lys Thr Leu Asp Ser Leu Arg
                20                  25                  30 act ctc tcg cca gat ttt atc agt gta act tgt agt aac aat aat tat     144
Thr Leu Ser Pro Asp Phe Ile Ser Val Thr Cys Ser Asn Asn Asn Tyr
            35                  40                  45 gat aat att gga gat aca act ata aag ttt gct gat tat gta aac aat     192
Asp Asn Ile Gly Asp Thr Thr Ile Lys Phe Ala Asp Tyr Val Asn Asn
        50                  55                  60 aca cta gat att cca gcg gtt gct cat tta cct gcc gct tat tta gat     240
Thr Leu Asp Ile Pro Ala Val Ala His Leu Pro Ala Ala Tyr Leu Asp
 65                  70                  75                  80 aaa gct caa gtg atc gaa att ttg gaa cgg tta aaa gat aaa caa atc     288
Lys Ala Gln Val Ile Glu Ile Leu Glu Arg Leu Lys Asp Lys Gln Ile
                 85                  90                  95 aaa aaa att ctt gct tta aga ggt gat atc agc gat gaa ccg atg aaa     336
Lys Lys Ile Leu Ala Leu Arg Gly Asp Ile Ser Asp Glu Pro Met Lys
                100                 105                 110 gat gat ttt aaa ttt gca agt gat ttg gtt aaa ttt atc aaa gat tat     384
Asp Asp Phe Lys Phe Ala Ser Asp Leu Val Lys Phe Ile Lys Asp Tyr
            115                 120                 125 gat gat agt ttt gaa gtt tta ggt gct tgc tac ccc gat att cat ccc     432
Asp Asp Ser Phe Glu Val Leu Gly Ala Cys Tyr Pro Asp Ile His Pro
        130                 135                 140 gaa tca gta aat cga gtg agt gat ttt cat tat ctg aaa gaa aaa gta     480
Glu Ser Val Asn Arg Val Ser Asp Phe His Tyr Leu Lys Glu Lys Val
145                 150                 155                 160 gat gct ggt tgt gac aga tta atc acg caa cta ttt ttt gat aat gat     528
Asp Ala Gly Cys Asp Arg Leu Ile Thr Gln Leu Phe Phe Asp Asn Asp
                165                 170                 175 agt ttc tat gat ttt caa gaa cga tgc gca att gct gag ata aat act     576
Ser Phe Tyr Asp Phe Gln Glu Arg Cys Ala Ile Ala Glu Ile Asn Thr
            180                 185                 190 ccg ata ttc gcc gga ata atg cca gta atc aat cga aat caa att ctt     624
Pro Ile Phe Ala Gly Ile Met Pro Val Ile Asn Arg Asn Gln Ile Leu
        195                 200                 205
```

```
cgt cta tta aaa aat tgt aat acg cca tta cca gca aaa ttc att aga      672
Arg Leu Leu Lys Asn Cys Asn Thr Pro Leu Pro Ala Lys Phe Ile Arg
    210                 215                 220 ata ctc gaa aaa tat gaa cat aat ctt atc gct tta agg gat gct gga      720
Ile Leu Glu Lys Tyr Glu His Asn Leu Ile Ala Leu Arg Asp Ala Gly
225                 230                 235                 240 att gct tac gcc atc gat caa atc gtt gat tta gta aca gag gat gtt      768
Ile Ala Tyr Ala Ile Asp Gln Ile Val Asp Leu Val Thr Glu Asp Val
                245                 250                 255 gct gga att cac ctc tat acg atg aat aat gca aat acg gca cac tcc      816
Ala Gly Ile His Leu Tyr Thr Met Asn Asn Ala Asn Thr Ala His Ser
            260                 265                 270 atc cat gct tca att tct tct tta ttt acc ttt tga                      852
Ile His Ala Ser Ile Ser Ser Leu Phe Thr Phe
            275                 280

<210> SEQ ID NO 50
<211> LENGTH: 283
<212> TYPE: PRT
<213> ORGANISM: Lactococcus lactis

<400> SEQUENCE: 50

Met Thr Ser Asn Ser Lys Ile Leu Ser Phe Glu Val Phe Pro Pro Thr
1               5                   10                  15

Thr Gln Ile Gly Ser Thr Asn Leu Val Lys Thr Leu Asp Ser Leu Arg
            20                  25                  30

Thr Leu Ser Pro Asp Phe Ile Ser Val Thr Cys Ser Asn Asn Asn Tyr
        35                  40                  45

Asp Asn Ile Gly Asp Thr Thr Ile Lys Phe Ala Asp Tyr Val Asn Asn
    50                  55                  60

Thr Leu Asp Ile Pro Ala Val Ala His Leu Pro Ala Ala Tyr Leu Asp
65                  70                  75                  80

Lys Ala Gln Val Ile Glu Ile Leu Glu Arg Leu Lys Asp Lys Gln Ile
                85                  90                  95

Lys Lys Ile Leu Ala Leu Arg Gly Asp Ile Ser Asp Glu Pro Met Lys
            100                 105                 110

Asp Asp Phe Lys Phe Ala Ser Asp Leu Val Lys Phe Ile Lys Asp Tyr
        115                 120                 125

Asp Asp Ser Phe Glu Val Leu Gly Ala Cys Tyr Pro Asp Ile His Pro
    130                 135                 140

Glu Ser Val Asn Arg Val Ser Asp Phe His Tyr Leu Lys Glu Lys Val
145                 150                 155                 160

Asp Ala Gly Cys Asp Arg Leu Ile Thr Gln Leu Phe Phe Asp Asn Asp
                165                 170                 175

Ser Phe Tyr Asp Phe Gln Glu Arg Cys Ala Ile Ala Glu Ile Asn Thr
            180                 185                 190

Pro Ile Phe Ala Gly Ile Met Pro Val Ile Asn Arg Asn Gln Ile Leu
        195                 200                 205

Arg Leu Leu Lys Asn Cys Asn Thr Pro Leu Pro Ala Lys Phe Ile Arg
    210                 215                 220

Ile Leu Glu Lys Tyr Glu His Asn Leu Ile Ala Leu Arg Asp Ala Gly
225                 230                 235                 240

Ile Ala Tyr Ala Ile Asp Gln Ile Val Asp Leu Val Thr Glu Asp Val
                245                 250                 255

Ala Gly Ile His Leu Tyr Thr Met Asn Asn Ala Asn Thr Ala His Ser
            260                 265                 270
```

Ile His Ala Ser Ile Ser Ser Leu Phe Thr Phe
        275                 280

<210> SEQ ID NO 51
<211> LENGTH: 891
<212> TYPE: DNA
<213> ORGANISM: Prochlorococcus maritima
<220> FEATURE:
<221> NAME/KEY: CDS
<222> LOCATION: (1)..(888)
<223> OTHER INFORMATION: RCK01602

<400> SEQUENCE: 51

| | | | | | | | | | | | | | | | | |
|---|---|---|---|---|---|---|---|---|---|---|---|---|---|---|---|---|
| ttg | aaa | tca | aaa | ctt | cag | caa | act | tta | gaa | aag | aat | tca | aaa | gta | att | 48 |
| Leu | Lys | Ser | Lys | Leu | Gln | Gln | Thr | Leu | Glu | Lys | Asn | Ser | Lys | Val | Ile | |
| 1 | | | | 5 | | | | | 10 | | | | | 15 | | |
| aca | gca | gaa | tta | atg | ccg | cca | aga | gga | gga | gac | ccc | gta | aga | tct | ctt | 96 |
| Thr | Ala | Glu | Leu | Met | Pro | Pro | Arg | Gly | Gly | Asp | Pro | Val | Arg | Ser | Leu | |
| | | | | 20 | | | | | 25 | | | | | 30 | | |
| aaa | ata | gca | caa | ctc | ttg | aga | aat | aag | gtg | cat | gca | gtt | aat | att | aca | 144 |
| Lys | Ile | Ala | Gln | Leu | Leu | Arg | Asn | Lys | Val | His | Ala | Val | Asn | Ile | Thr | |
| | | 35 | | | | | 40 | | | | | 45 | | | | |
| gac | gga | agt | aga | gca | ata | atg | aga | atg | tgt | agt | tta | gca | atg | tct | aaa | 192 |
| Asp | Gly | Ser | Arg | Ala | Ile | Met | Arg | Met | Cys | Ser | Leu | Ala | Met | Ser | Lys | |
| | 50 | | | | | 55 | | | | | 60 | | | | | |
| cta | tta | cta | gac | aat | ggg | ata | gaa | cct | ata | atg | cag | atc | tca | tgt | aga | 240 |
| Leu | Leu | Leu | Asp | Asn | Gly | Ile | Glu | Pro | Ile | Met | Gln | Ile | Ser | Cys | Arg | |
| 65 | | | | | 70 | | | | | 75 | | | | | 80 | |
| gat | cgt | aat | aaa | att | gct | tta | caa | tca | gat | att | ctt | gga | gca | aat | gcc | 288 |
| Asp | Arg | Asn | Lys | Ile | Ala | Leu | Gln | Ser | Asp | Ile | Leu | Gly | Ala | Asn | Ala | |
| | | | | 85 | | | | | 90 | | | | | 95 | | |
| tta | gga | att | aaa | aat | att | tta | tgc | att | aca | gga | gat | tct | gta | aaa | gcc | 336 |
| Leu | Gly | Ile | Lys | Asn | Ile | Leu | Cys | Ile | Thr | Gly | Asp | Ser | Val | Lys | Ala | |
| | | | 100 | | | | | 105 | | | | | 110 | | | |
| gga | gat | cag | caa | gaa | aca | aaa | gcc | gtt | cat | gaa | ttt | gag | gca | gta | aga | 384 |
| Gly | Asp | Gln | Gln | Glu | Thr | Lys | Ala | Val | His | Glu | Phe | Glu | Ala | Val | Arg | |
| | | 115 | | | | | 120 | | | | | 125 | | | | |
| tta | tta | aaa | caa | att | caa | tca | ttc | aat | caa | gga | att | gat | cct | act | ttt | 432 |
| Leu | Leu | Lys | Gln | Ile | Gln | Ser | Phe | Asn | Gln | Gly | Ile | Asp | Pro | Thr | Phe | |
| | 130 | | | | | 135 | | | | | 140 | | | | | |
| gaa | caa | ctt | cca | gac | aaa | agg | act | gaa | att | ttc | tca | ggt | gcg | gca | gta | 480 |
| Glu | Gln | Leu | Pro | Asp | Lys | Arg | Thr | Glu | Ile | Phe | Ser | Gly | Ala | Ala | Val | |
| 145 | | | | | 150 | | | | | 155 | | | | | 160 | |
| gat | cca | agt | tgt | cga | aat | caa | aga | agt | tta | aaa | agt | aga | aca | att | aaa | 528 |
| Asp | Pro | Ser | Cys | Arg | Asn | Gln | Arg | Ser | Leu | Lys | Ser | Arg | Thr | Ile | Lys | |
| | | | 165 | | | | | 170 | | | | | 175 | | | |
| aaa | aaa | gag | gcc | ggt | gca | aat | ttc | tta | caa | act | caa | ata | gtt | atg | gat | 576 |
| Lys | Lys | Glu | Ala | Gly | Ala | Asn | Phe | Leu | Gln | Thr | Gln | Ile | Val | Met | Asp | |
| | | | 180 | | | | | 185 | | | | | 190 | | | |
| aga | aaa | tgt | tta | gca | gac | ttt | tgc | aac | gaa | atc | agt | aat | cca | ctt | gag | 624 |
| Arg | Lys | Cys | Leu | Ala | Asp | Phe | Cys | Asn | Glu | Ile | Ser | Asn | Pro | Leu | Glu | |
| | 195 | | | | | 200 | | | | | 205 | | | | | |
| ata | cca | gtt | att | gca | gga | gta | ttt | ctt | tta | aaa | tca | tat | aaa | aat | gct | 672 |
| Ile | Pro | Val | Ile | Ala | Gly | Val | Phe | Leu | Leu | Lys | Ser | Tyr | Lys | Asn | Ala | |
| 210 | | | | | 215 | | | | | 220 | | | | | | |
| ctt | ttc | ata | aat | aaa | ttt | gta | cct | gga | gcg | aat | att | cct | gaa | aat | gtt | 720 |
| Leu | Phe | Ile | Asn | Lys | Phe | Val | Pro | Gly | Ala | Asn | Ile | Pro | Glu | Asn | Val | |
| 225 | | | | | 230 | | | | | 235 | | | | | 240 | |
| tta | aat | cgt | ctc | aaa | gat | gca | aaa | aat | cca | ctt | caa | gaa | gga | ata | tta | 768 |
| Leu | Asn | Arg | Leu | Lys | Asp | Ala | Lys | Asn | Pro | Leu | Gln | Glu | Gly | Ile | Leu | |
| | | | | 245 | | | | | 250 | | | | | 255 | | |

```
att gct tca gag caa gct caa gat ttt att aat att gca gat gga att        816
Ile Ala Ser Glu Gln Ala Gln Asp Phe Ile Asn Ile Ala Asp Gly Ile
        260                 265                 270 cat ctt atg gca gtc aaa tca gaa cat ctt atc cca gag ata ctt gaa        864
His Leu Met Ala Val Lys Ser Glu His Leu Ile Pro Glu Ile Leu Glu
        275                 280                 285 aaa gct ggt ctc aat ctg gaa tgt taa                                    891
Lys Ala Gly Leu Asn Leu Glu Cys
290                 295

<210> SEQ ID NO 52
<211> LENGTH: 296
<212> TYPE: PRT
<213> ORGANISM: Prochlorococcus maritima

<400> SEQUENCE: 52

Leu Lys Ser Lys Leu Gln Gln Thr Leu Glu Lys Asn Ser Lys Val Ile
 1               5                  10                  15

Thr Ala Glu Leu Met Pro Pro Arg Gly Gly Asp Pro Val Arg Ser Leu
            20                  25                  30

Lys Ile Ala Gln Leu Leu Arg Asn Lys Val His Ala Val Asn Ile Thr
        35                  40                  45

Asp Gly Ser Arg Ala Ile Met Arg Met Cys Ser Leu Ala Met Ser Lys
    50                  55                  60

Leu Leu Leu Asp Asn Gly Ile Glu Pro Ile Met Gln Ile Ser Cys Arg
65                  70                  75                  80

Asp Arg Asn Lys Ile Ala Leu Gln Ser Asp Ile Leu Gly Ala Asn Ala
                85                  90                  95

Leu Gly Ile Lys Asn Ile Leu Cys Ile Thr Gly Asp Ser Val Lys Ala
            100                 105                 110

Gly Asp Gln Gln Glu Thr Lys Ala Val His Glu Phe Glu Ala Val Arg
        115                 120                 125

Leu Leu Lys Gln Ile Gln Ser Phe Asn Gln Gly Ile Asp Pro Thr Phe
    130                 135                 140

Glu Gln Leu Pro Asp Lys Arg Thr Glu Ile Phe Ser Gly Ala Ala Val
145                 150                 155                 160

Asp Pro Ser Cys Arg Asn Gln Arg Ser Leu Lys Ser Arg Thr Ile Lys
                165                 170                 175

Lys Lys Glu Ala Gly Ala Asn Phe Leu Gln Thr Gln Ile Val Met Asp
            180                 185                 190

Arg Lys Cys Leu Ala Asp Phe Cys Asn Glu Ile Ser Asn Pro Leu Glu
        195                 200                 205

Ile Pro Val Ile Ala Gly Val Phe Leu Leu Lys Ser Tyr Lys Asn Ala
    210                 215                 220

Leu Phe Ile Asn Lys Phe Val Pro Gly Ala Asn Ile Pro Glu Asn Val
225                 230                 235                 240

Leu Asn Arg Leu Lys Asp Ala Lys Asn Pro Leu Gln Glu Gly Ile Leu
                245                 250                 255

Ile Ala Ser Glu Gln Ala Gln Asp Phe Ile Asn Ile Ala Asp Gly Ile
            260                 265                 270

His Leu Met Ala Val Lys Ser Glu His Leu Ile Pro Glu Ile Leu Glu
        275                 280                 285

Lys Ala Gly Leu Asn Leu Glu Cys
    290                 295

<210> SEQ ID NO 53
```

```
<211> LENGTH: 1848
<212> TYPE: DNA
<213> ORGANISM: Bacillus stearothermophilus
<220> FEATURE:
<221> NAME/KEY: CDS
<222> LOCATION: (1)..(1845)
<223> OTHER INFORMATION: RBE04103

<400> SEQUENCE: 53 gtg gga ttg ctg gat gag ttg aaa gag cgc att ctc atc gcc gac ggg       48
Val Gly Leu Leu Asp Glu Leu Lys Glu Arg Ile Leu Ile Ala Asp Gly
 1               5                  10                  15 gcg atg gga acg ctt tta tat tcg cac ggc att gac cgt tgt ttt gaa       96
Ala Met Gly Thr Leu Leu Tyr Ser His Gly Ile Asp Arg Cys Phe Glu
             20                  25                  30 gaa ttg aat cta tcc aat cca gat gaa atc gtc cat att cat gaa gcg      144
Glu Leu Asn Leu Ser Asn Pro Asp Glu Ile Val His Ile His Glu Ala
         35                  40                  45 tat atc gcc gcg ggc gcc gac gtc att cag acg aat aca tac ggc gcc      192
Tyr Ile Ala Ala Gly Ala Asp Val Ile Gln Thr Asn Thr Tyr Gly Ala
     50                  55                  60 aac tat gtg aaa ctc gcc cgc tac ggc ctt gaa gat gag gtc ccg gcc      240
Asn Tyr Val Lys Leu Ala Arg Tyr Gly Leu Glu Asp Glu Val Pro Ala
 65                  70                  75                  80 atc aac cgc gcg gcg gtg cgg ctc gcc agg caa gcg gcg aac gga cgg      288
Ile Asn Arg Ala Ala Val Arg Leu Ala Arg Gln Ala Ala Asn Gly Arg
                 85                  90                  95 gca tac gtg ctc ggg acg atc ggg ggg ctg cgc acg tta aac aaa agc      336
Ala Tyr Val Leu Gly Thr Ile Gly Gly Leu Arg Thr Leu Asn Lys Ser
            100                 105                 110 gtc gtc acg ctc gaa gaa gtg aag cgg acg ttt cgc gag cag ctg ttt      384
Val Val Thr Leu Glu Glu Val Lys Arg Thr Phe Arg Glu Gln Leu Phe
        115                 120                 125 gtc ctg ctc gct gaa ggg gtc gac ggc gtg ctg ctc gag acg tat tac      432
Val Leu Leu Ala Glu Gly Val Asp Gly Val Leu Leu Glu Thr Tyr Tyr
    130                 135                 140 gat ttg gaa gag ttg gag acg gtg ctt gcc atc gcc cgc aaa gag acc      480
Asp Leu Glu Glu Leu Glu Thr Val Leu Ala Ile Ala Arg Lys Glu Thr
145                 150                 155                 160 gac ttg ccg att atc gct cac gtc tcg ctc cat gaa gtc ggc gtc ttg      528
Asp Leu Pro Ile Ile Ala His Val Ser Leu His Glu Val Gly Val Leu
                165                 170                 175 caa gat ggc acg ccg ctc gcg gac gcc ctt gcc cgc cta gag gcg ctc      576
Gln Asp Gly Thr Pro Leu Ala Asp Ala Leu Ala Arg Leu Glu Ala Leu
            180                 185                 190 ggg gcc gat gtc gtc gga ctg aac tgt cgt ctc ggt cca tat cat atg      624
Gly Ala Asp Val Val Gly Leu Asn Cys Arg Leu Gly Pro Tyr His Met
        195                 200                 205 ctt cgg tcg ctc gag gaa gtg ccg ctg cca aat cga gcg ttt ttg tcg      672
Leu Arg Ser Leu Glu Glu Val Pro Leu Pro Asn Arg Ala Phe Leu Ser
    210                 215                 220 gcg tat ccg aac gcc agc ctt ccg gat tac cgc gat ggg cgg ctt gtc      720
Ala Tyr Pro Asn Ala Ser Leu Pro Asp Tyr Arg Asp Gly Arg Leu Val
225                 230                 235                 240 tat gag acg aac gct gaa tat ttc gag gaa acg gcc aaa gcg ttc cgc      768
Tyr Glu Thr Asn Ala Glu Tyr Phe Glu Glu Thr Ala Lys Ala Phe Arg
                245                 250                 255 gac caa ggg gtg cgc ttg atc ggc ggg tgc tgc ggc acg acg ccg aaa      816
Asp Gln Gly Val Arg Leu Ile Gly Gly Cys Cys Gly Thr Thr Pro Lys
            260                 265                 270 cat atc gaa gcg atg gca aaa gcg ctc tcc gac cga acg ccg gtg acg      864
```

-continued

```
                His Ile Glu Ala Met Ala Lys Ala Leu Ser Asp Arg Thr Pro Val Thr
                            275                 280                 285
gaa aaa acg gtg aaa cgg cgc gcg gtg tct gta tca gtg caa gcg gag            912
Glu Lys Thr Val Lys Arg Arg Ala Val Ser Val Ser Val Gln Ala Glu
290                 295                 300
cgg ccc gcc cca tct ccc ctt ccc gag ctt gcc cgc acg cac cgc tcg            960
Arg Pro Ala Pro Ser Pro Leu Pro Glu Leu Ala Arg Thr His Arg Ser
305                 310                 315                 320
gtc att gtg gag ctg gat ccg ccg aaa aaa ttg ggg att gac aag ttt           1008
Val Ile Val Glu Leu Asp Pro Pro Lys Lys Leu Gly Ile Asp Lys Phe
                325                 330                 335
ctt gcc ggg gcg aaa gcg ctc cat gac gcc ggc atc gat gcg ctg acg           1056
Leu Ala Gly Ala Lys Ala Leu His Asp Ala Gly Ile Asp Ala Leu Thr
                340                 345                 350
ttg gcc gac aac tcg ctc gcc acg ccg cgc atc agc aac gcc gct gtc           1104
Leu Ala Asp Asn Ser Leu Ala Thr Pro Arg Ile Ser Asn Ala Ala Val
                355                 360                 365
gcc acg atc atc aag gag caa ctc ggc atc cgc ccg ctc gtg cat att           1152
Ala Thr Ile Ile Lys Glu Gln Leu Gly Ile Arg Pro Leu Val His Ile
370                 375                 380
aca tgc cgc gat cgc aat ttg atc ggc ttg cag tcg cat ttg atg ggc           1200
Thr Cys Arg Asp Arg Asn Leu Ile Gly Leu Gln Ser His Leu Met Gly
385                 390                 395                 400
ttg cat acg ctc ggc atc acc gat gtg ctc gcc att acc ggc gac ccg           1248
Leu His Thr Leu Gly Ile Thr Asp Val Leu Ala Ile Thr Gly Asp Pro
                405                 410                 415
tcg aaa atc ggc gat ttt cca ggg gca acg tcc gtg tac gac tta tca           1296
Ser Lys Ile Gly Asp Phe Pro Gly Ala Thr Ser Val Tyr Asp Leu Ser
                420                 425                 430
tcg ttc gat ttg atc cgc ttg atc cgc cag ttt aac gaa ggg ctg tcg           1344
Ser Phe Asp Leu Ile Arg Leu Ile Arg Gln Phe Asn Glu Gly Leu Ser
                435                 440                 445
tac tcg ggc aaa ccg ctt ggg caa aaa acg aac ttc tcg atc ggc gct           1392
Tyr Ser Gly Lys Pro Leu Gly Gln Lys Thr Asn Phe Ser Ile Gly Ala
            450                 455                 460
gcg ttc aac ccg aac gtc cgc cat ttg gac aaa gcg gtc gag cgg atg           1440
Ala Phe Asn Pro Asn Val Arg His Leu Asp Lys Ala Val Glu Arg Met
465                 470                 475                 480
gag aaa aaa atc caa tgc ggc gcc cat tat ttc ttg acc cag ccg att           1488
Glu Lys Lys Ile Gln Cys Gly Ala His Tyr Phe Leu Thr Gln Pro Ile
                485                 490                 495
tac tcg gaa gag aaa atc gtt gaa gtg cac gaa gcg acc aag cat ctt           1536
Tyr Ser Glu Glu Lys Ile Val Glu Val His Glu Ala Thr Lys His Leu
                500                 505                 510
gac acg ccg att tac atc ggc att atg ccg ctt gtg agc gcg cgc aac           1584
Asp Thr Pro Ile Tyr Ile Gly Ile Met Pro Leu Val Ser Ala Arg Asn
                515                 520                 525
gcc gac ttt ttg cat cat gaa gtg ccg ggc att acg ctc tct gac gag           1632
Ala Asp Phe Leu His His Glu Val Pro Gly Ile Thr Leu Ser Asp Glu
            530                 535                 540
att cgc gcc cgc atg gcc gcc tgc agc ggc gac ccg gtg caa gca gcc           1680
Ile Arg Ala Arg Met Ala Ala Cys Ser Gly Asp Pro Val Gln Ala Ala
545                 550                 555                 560
aag gaa ggc atc gct atc gcc aaa tcg ctc att gac gct gcg ttt gat           1728
Lys Glu Gly Ile Ala Ile Ala Lys Ser Leu Ile Asp Ala Ala Phe Asp
                565                 570                 575
ttg ttt aac ggc att tat ttg atc acg ccg ttc ttg cgc tac gac atg           1776
Leu Phe Asn Gly Ile Tyr Leu Ile Thr Pro Phe Leu Arg Tyr Asp Met
                580                 585                 590
```

```
acg gtc gag ctt gtc cgc tac att cac gaa aaa gaa gcg gcc gcc aaa    1824
Thr Val Glu Leu Val Arg Tyr Ile His Glu Lys Glu Ala Ala Ala Lys
        595                 600                 605 gaa agg aag gtt gtt cat ggc taa                                    1848
Glu Arg Lys Val Val His Gly
    610                 615
```

<210> SEQ ID NO 54
<211> LENGTH: 615
<212> TYPE: PRT
<213> ORGANISM: Bacillus stearothermophilus

<400> SEQUENCE: 54

```
Val Gly Leu Leu Asp Glu Leu Lys Glu Arg Ile Leu Ile Ala Asp Gly
 1               5                  10                  15

Ala Met Gly Thr Leu Leu Tyr Ser His Gly Ile Asp Arg Cys Phe Glu
                20                  25                  30

Glu Leu Asn Leu Ser Asn Pro Asp Glu Ile Val His Ile His Glu Ala
            35                  40                  45

Tyr Ile Ala Ala Gly Ala Asp Val Ile Gln Thr Asn Thr Tyr Gly Ala
        50                  55                  60

Asn Tyr Val Lys Leu Ala Arg Tyr Gly Leu Glu Asp Glu Val Pro Ala
 65                  70                  75                  80

Ile Asn Arg Ala Ala Val Arg Leu Ala Arg Gln Ala Ala Asn Gly Arg
                85                  90                  95

Ala Tyr Val Leu Gly Thr Ile Gly Gly Leu Arg Thr Leu Asn Lys Ser
               100                 105                 110

Val Val Thr Leu Glu Glu Val Lys Arg Thr Phe Arg Glu Gln Leu Phe
            115                 120                 125

Val Leu Leu Ala Glu Gly Val Asp Gly Val Leu Leu Glu Thr Tyr Tyr
        130                 135                 140

Asp Leu Glu Glu Leu Glu Thr Val Leu Ala Ile Ala Arg Lys Glu Thr
145                 150                 155                 160

Asp Leu Pro Ile Ile Ala His Val Ser Leu His Glu Val Gly Val Leu
                165                 170                 175

Gln Asp Gly Thr Pro Leu Ala Asp Ala Leu Ala Arg Leu Glu Ala Leu
            180                 185                 190

Gly Ala Asp Val Val Gly Leu Asn Cys Arg Leu Gly Pro Tyr His Met
        195                 200                 205

Leu Arg Ser Leu Glu Glu Val Pro Leu Pro Asn Arg Ala Phe Leu Ser
    210                 215                 220

Ala Tyr Pro Asn Ala Ser Leu Pro Asp Tyr Arg Asp Gly Arg Leu Val
225                 230                 235                 240

Tyr Glu Thr Asn Ala Glu Tyr Phe Glu Glu Thr Ala Lys Ala Phe Arg
                245                 250                 255

Asp Gln Gly Val Arg Leu Ile Gly Gly Cys Cys Gly Thr Thr Pro Lys
            260                 265                 270

His Ile Glu Ala Met Ala Lys Ala Leu Ser Asp Arg Thr Pro Val Thr
        275                 280                 285

Glu Lys Thr Val Lys Arg Arg Ala Val Ser Val Ser Val Gln Ala Glu
    290                 295                 300

Arg Pro Ala Pro Ser Pro Leu Pro Glu Leu Ala Arg Thr His Arg Ser
305                 310                 315                 320

Val Ile Val Glu Leu Asp Pro Pro Lys Lys Leu Gly Ile Asp Lys Phe
                325                 330                 335
```

```
Leu Ala Gly Ala Lys Ala Leu His Asp Ala Gly Ile Asp Ala Leu Thr
            340                 345                 350
Leu Ala Asp Asn Ser Leu Ala Thr Pro Arg Ile Ser Asn Ala Ala Val
        355                 360                 365
Ala Thr Ile Ile Lys Glu Gln Leu Gly Ile Arg Pro Leu Val His Ile
    370                 375                 380
Thr Cys Arg Asp Arg Asn Leu Ile Gly Leu Gln Ser His Leu Met Gly
385                 390                 395                 400
Leu His Thr Leu Gly Ile Thr Asp Val Leu Ala Ile Thr Gly Asp Pro
                405                 410                 415
Ser Lys Ile Gly Asp Phe Pro Gly Ala Thr Ser Val Tyr Asp Leu Ser
            420                 425                 430
Ser Phe Asp Leu Ile Arg Leu Ile Arg Gln Phe Asn Glu Gly Leu Ser
        435                 440                 445
Tyr Ser Gly Lys Pro Leu Gly Gln Lys Thr Asn Phe Ser Ile Gly Ala
    450                 455                 460
Ala Phe Asn Pro Asn Val Arg His Leu Asp Lys Ala Val Glu Arg Met
465                 470                 475                 480
Glu Lys Lys Ile Gln Cys Gly Ala His Tyr Phe Leu Thr Gln Pro Ile
                485                 490                 495
Tyr Ser Glu Glu Lys Ile Val Glu Val His Glu Ala Thr Lys His Leu
            500                 505                 510
Asp Thr Pro Ile Tyr Ile Gly Ile Met Pro Leu Val Ser Ala Arg Asn
        515                 520                 525
Ala Asp Phe Leu His His Glu Val Pro Gly Ile Thr Leu Ser Asp Glu
    530                 535                 540
Ile Arg Ala Arg Met Ala Ala Cys Ser Gly Asp Pro Val Gln Ala Ala
545                 550                 555                 560
Lys Glu Gly Ile Ala Ile Ala Lys Ser Leu Ile Asp Ala Ala Phe Asp
                565                 570                 575
Leu Phe Asn Gly Ile Tyr Leu Ile Thr Pro Phe Leu Arg Tyr Asp Met
            580                 585                 590
Thr Val Glu Leu Val Arg Tyr Ile His Glu Lys Glu Ala Ala Ala Lys
        595                 600                 605
Glu Arg Lys Val Val His Gly
    610                 615

<210> SEQ ID NO 55
<211> LENGTH: 52
<212> TYPE: DNA
<213> ORGANISM: Artificial sequence
<220> FEATURE:
<223> OTHER INFORMATION: Description of the artificial sequence:PCR
      primer

<400> SEQUENCE: 55
cccgggatcc gctagcggcg cgccggccgg cccggtgtga ataccgcac ag          52

<210> SEQ ID NO 56
<211> LENGTH: 53
<212> TYPE: DNA
<213> ORGANISM: Artificial sequence
<220> FEATURE:
<223> OTHER INFORMATION: Description of the artificial sequence:PCR
      primer

<400> SEQUENCE: 56
tctagactcg agcggccgcg gccggccttt aaattgaaga cgaaagggcc tcg         53
```

<210> SEQ ID NO 57
<211> LENGTH: 47
<212> TYPE: DNA
<213> ORGANISM: Artificial sequence
<220> FEATURE:
<223> OTHER INFORMATION: Description of the artificial sequence:PCR primer

<400> SEQUENCE: 57
gagatctaga cccggggatc cgctagcggg ctgctaaagg aagcgga         47

<210> SEQ ID NO 58
<211> LENGTH: 38
<212> TYPE: DNA
<213> ORGANISM: Artificial sequence
<220> FEATURE:
<223> OTHER INFORMATION: Description of the artificial sequence:PCR primer

<400> SEQUENCE: 58
gagaggcgcg ccgctagcgt gggcgaagaa ctccagca         38

<210> SEQ ID NO 59
<211> LENGTH: 34
<212> TYPE: DNA
<213> ORGANISM: Artificial sequence
<220> FEATURE:
<223> OTHER INFORMATION: Description of the artificial sequence:PCR primer

<400> SEQUENCE: 59
gagagggcgg ccgcgcaaag tcccgcttcg tgaa         34

<210> SEQ ID NO 60
<211> LENGTH: 34
<212> TYPE: DNA
<213> ORGANISM: Artificial sequence
<220> FEATURE:
<223> OTHER INFORMATION: Description of the artificial sequence:PCR primer

<400> SEQUENCE: 60
gagagggcgg ccgctcaagt cggtcaagcc acgc         34

<210> SEQ ID NO 61
<211> LENGTH: 140
<212> TYPE: DNA
<213> ORGANISM: Artificial sequence
<220> FEATURE:
<223> OTHER INFORMATION: Description of the artificial sequence:PCR primer

<400> SEQUENCE: 61
tcgaatttaa atctcgagag gcctgacgtc gggcccggta ccacgcgtca tatgactagt         60
tcggacctag ggatatcgtc gacatcgatg ctcttctgcg ttaattaaca attgggatcc        120
tctagacccg ggatttaaat        140

<210> SEQ ID NO 62
<211> LENGTH: 140
<212> TYPE: DNA
<213> ORGANISM: Artificial sequence
<220> FEATURE:
<223> OTHER INFORMATION: Description of the artificial sequence:PCR primer

```
<400> SEQUENCE: 62
gatcatttaa atcccgggtc tagaggatcc caattgttaa ttaacgcaga agagcatcga        60
tgtcgacgat atccctaggt ccgaactagt catatgacgc gtggtaccgg gcccgacgtc       120
aggcctctcg agatttaaat                                                   140

<210> SEQ ID NO 63
<211> LENGTH: 33
<212> TYPE: DNA
<213> ORGANISM: Artificial sequence
<220> FEATURE:
<223> OTHER INFORMATION: Description of the artificial sequence:PCR
      primer

<400> SEQUENCE: 63
gagagcggcc gccgatcctt tttaacccat cac                                     33

<210> SEQ ID NO 64
<211> LENGTH: 32
<212> TYPE: DNA
<213> ORGANISM: Artificial sequence
<220> FEATURE:
<223> OTHER INFORMATION: Description of the artificial sequence:PCR
      primer

<400> SEQUENCE: 64
aggagcggcc gccatcggca ttttcttttg cg                                      32

<210> SEQ ID NO 65
<211> LENGTH: 5091
<212> TYPE: DNA
<213> ORGANISM: Artificial sequence
<220> FEATURE:
<223> OTHER INFORMATION: Description of the artificial sequence:plasmid

<400> SEQUENCE: 65
gccgcgactg ccttcgcgaa gccttgcccc gcggaaattt cctccaccga gttcgtgcac        60 accctatgc caagcttctt tcaccctaaa ttcgagagat tggattctta ccgtggaaat       120
tcttcgcaaa aatcgtcccc tgatcgccct tgcgacgttg gcgtcggtgc cgctggttgc       180
gcttggcttg accgacttga tcagcggccg ctcgatttaa atctcgagag gcctgacgtc       240
gggcccggta ccacgcgtca tatgactagt tcggacctag ggatatcgtc gacatcgatg       300
ctcttctgcg ttaattaaca attgggatcc tctagacccg ggatttaaat cgctagcggg       360
ctgctaaagg aagcggaaca cgtagaaagc cagtccgcag aaacggtgct gacccccggat     420 gaatgtcagc tactgggcta tctggacaag ggaaaacgca agcgcaaaga gaaagcaggt       480
agcttgcagt gggcttacat ggcgatagct agactgggcg gttttatgga cagcaagcga       540
accggaattg ccagctgggg cgccctctgg taaggttggg aagccctgca agtaaactg        600 gatggctttc ttgccgccaa ggatctgatg gcgcagggga tcaagatctg atcaagagac       660
aggatgagga tcgtttcgca tgattgaaca agatggattg cacgcaggtt ctccggccgc       720
ttgggtggag aggctattcg gctatgactg gcacaacag acaatcggct gctctgatgc        780
cgccgtgttc cggctgtcag cgcaggggcg cccggttctt tttgtcaaga ccgacctgtc       840
cggtgccctg aatgaactgc aggacgagg agcgcggcta tcgtggctgg ccacgacggg       900
cgttccttgc gcagctgtgc tcgacgttgt cactgaagcg ggaagggact ggctgctatt       960
gggcgaagtg ccggggcagg atcctcctgtc atctcacctt gctcctgccg agaaagtatc     1020
catcatggct gatgcaatgc ggcggctgca tacgcttgat ccggctacct gcccattcga     1080
```

-continued

```
ccaccaagcg aaacatcgca tcgagcgagc acgtactcgg atggaagccg gtcttgtcga   1140
tcaggatgat ctggacgaag agcatcaggg gctcgcgcca gccgaactgt tcgccaggct   1200
caaggcgcgc atgcccgacg cgaggatct cgtcgtgacc catggcgatg cctgcttgcc    1260
gaatatcatg gtggaaaatg ccgcttttc tggattcatc gactgtggcc ggctgggtgt    1320
ggcggaccgc tatcaggaca tagcgttggc tacccgtgat attgctgaag agcttggcgg   1380
cgaatgggct gaccgcttcc tcgtgcttta cggtatcgcc gctcccgatt cgcagcgcat   1440
cgccttctat cgccttcttg acgagttctt ctgagcggga ctctggggtt cgaaatgacc   1500
gaccaagcga cgcccaacct gccatcacga gatttcgatt ccaccgccgc cttctatgaa   1560
aggttgggct tcggaatcgt tttccgggac gccggctgga tgatcctcca gcgcggggat   1620
ctcatgctgg agttcttcgc ccacgctagc ggcgcgccgg ccggcccggt gtgaaatacc   1680
gcacagatgc gtaaggagaa ataccgcat caggcgctct tccgcttcct cgctcactga    1740
ctcgctgcgc tcggtcgttc ggctgcggcg agcggtatca gctcactcaa aggcggtaat   1800
acggttatcc acagaatcag gggataacgc aggaaagaac atgtgagcaa aaggccagca   1860
aaaggccagg aaccgtaaaa aggccgcgtt gctggcgttt ttccataggc tccgcccccc   1920
tgacgagcat cacaaaaatc gacgctcaag tcagaggtgg cgaaacccga caggactata   1980
aagataccag gcgtttcccc ctggaagctc cctcgtgcgc tctcctgttc cgaccctgcc   2040
gcttaccgga tacctgtccg cctttctccc ttcgggaagc gtggcgcttt ctcatagctc   2100
acgctgtagg tatctcagtt cggtgtaggt cgttcgctcc aagctgggct gtgtgcacga   2160
accccccgtt cagcccgacc gctgcgcctt atccggtaac tatcgtcttg agtccaaccc   2220
ggtaagacac gacttatcgc cactggcagc agccactggt aacaggatta gcagagcgag   2280
gtatgtaggc ggtgctacag agttcttgaa gtggtggcct aactacggct acactagaag   2340
gacagtattt ggtatctgcg ctctgctgaa gccagttacc ttcggaaaaa gagttggtag   2400
ctcttgatcc ggcaaacaaa ccaccgctgg tagcggtggt ttttttgttt gcaagcagca   2460
gattacgcgc agaaaaaaag gatctcaaga agatcctttg atcttttcta cggggtctga   2520
cgctcagtgg aacgaaaact cacgttaagg gattttggtc atgagattat caaaaaggat   2580
cttcacctag atccttttaa aggccggccc cggccgcgca aagtcccgct tcgtgaaaat   2640
tttcgtgccg cgtgattttc cgccaaaaac tttaacgaac gttcgttata atggtgtcat   2700
gaccttcacg acgaagtact aaaattggcc cgaatcatca gctatggatc tctctgatgt   2760
cgcgctggag tccgacgcgc tcgatgctgc cgtcgattta aaaacggtga tcggattttt   2820
ccgagctctc gatacgacgg acgcgccagc atcacgagac tgggccagtg ccgcgagcga   2880
cctagaaact ctcgtggcgg atcttgagga gctggctgac gagctgcgtg ctcggccagc   2940
gccaggagga cgcacagtag tggaggatgc aatcagttgc gcctactgcg gtggcctgat   3000
tcctccccgg cctgacccgc gaggacggcg cgcaaaatat tgctcagatg cgtgtcgtgc   3060
cgcagccagc cgcgagcgcg ccaacaaacg ccacgccgag gagctggagg cggctaggtc   3120
gcaaatggcg ctggaagtgc gtcccccgag cgaaattttg gccatggtcg tcacagagct   3180
ggaagcggca gcgagaatta tcgcgatcgt ggcggtgccc gcaggcatga caaacatcgt   3240
aaatgccgcg tttcgtgtgc cgtggccgcc caggacgtgt cagcgccgcc accacctgca   3300
ccgaatcggc agcagcgtcg cgcgtcgaaa aagcgcacag gcggcaagaa gcgataagct   3360
gcacgaatac ctgaaaaatg ttgaacgccc cgtgagcggt aactcacagg gcgtcggcta   3420
```

```
accccccagtc caaacctggg agaaagcgct caaaaatgac tctagcggat tcacgagaca   3480
ttgacacacc ggcctggaaa ttttccgctg atctgttcga cacccatccc gagctcgcgc   3540
tgcgatcacg tggctggacg agcgaagacc gccgcgaatt cctcgctcac ctgggcagag   3600
aaaatttcca gggcagcaag acccgcgact tcgccagcgc ttggatcaaa gacccggaca   3660
cggagaaaca cagccgaagt tataccgagt tggttcaaaa tcgcttgccc ggtgccagta   3720
tgttgctctg acgcacgcgc agcacgcagc cgtgcttgtc ctggacattg atgtgccgag   3780
ccaccaggcc ggcgggaaaa tcgagcacgt aaaccccgag gtctacgcga ttttggagcg   3840
ctgggcacgc ctggaaaaag cgccagcttg atcggcgtg aatccactga gcgggaaatg    3900
ccagctcatc tggctcattg atccggtgta tgccgcagca ggcatgagca gcccgaatat   3960
gcgcctgctg gctgcaacga ccgaggaaat gacccgcgtt tcggcgctg accaggcttt    4020 ttcacatagg ctgagccgtg gccactgcac tctccgacga tcccagccgt accgctggca   4080
tgcccagcac aatcgcgtgg atcgcctagc tgatcttatg gaggttgctc gcatgatctc   4140
aggcacagaa aaacctaaaa aacgctatga gcaggagttt tctagcggac gggcacgtat   4200
cgaagcggca agaaaagcca ctgcggaagc aaaagcactt gccacgcttg aagcaagcct   4260
gccgagcgcc gctgaagcgt ctggagagct gatcgacggc gtccgtgtcc tctggactgc   4320
tccagggcgt gccgcccgtg atgagacggc ttttcgccac gctttgactg tgggatacca   4380
gttaaaagcg gctggtgagc gcctaaaaga caccaagggt catcgagcct acgagcgtgc   4440
ctacaccgtc gctcaggcgg tcggaggagg ccgtgagcct gatctgccgc cggactgtga   4500
ccgccagacg gattggccgc gacgtgtgcg cggctacgtc gctaaaggcc agccagtcgt   4560
ccctgctcgt cagacagaga cgcagagcca gccgaggcga aaagctctgg ccactatggg   4620
aagacgtggc ggtaaaaagg ccgcagaacg ctggaaagac ccaaacagtg agtacgcccg   4680
agcacagcga gaaaaactag ctaagtccag tcaacgacaa gctaggaaag ctaaggaaa    4740 tcgcttgacc attgcaggtt ggtttatgac tgttgaggga gagactggct cgtggccgac   4800
aatcaatgaa gctatgtctg aatttagcgt gtcacgtcag accgtgaata gagcacttaa   4860
ggtctgcggg cattgaactt ccacgaggac gccgaaagct tcccagtaaa tgtgccatct   4920
cgtaggcaga aaacggttcc cccgtagggt ctctctcttg gcctccttc taggtcgggc    4980 tgattgctct tgaagctctc tagggggggct cacaccatag gcagataacg ttccccaccg   5040
gctcgcctcg taagcgcaca aggactgctc ccaaagatct tcaaagccac t             5091
```

<210> SEQ ID NO 66
<211> LENGTH: 4323
<212> TYPE: DNA
<213> ORGANISM: Artificial sequence
<220> FEATURE:
<223> OTHER INFORMATION: Description of the artificial sequence: plasmid

<400> SEQUENCE: 66

```
tctctcagcg tatggttgtc gcctgagctg tagttgcctt catcgatgaa ctgctgtaca    60
ttttgatacg tttttccgtc accgtcaaag attgatttat aatcctctac accgttgatg   120
ttcaaagagc tgtctgatgc tgatacgtta acttgtgcag ttgtcagtgt tgtttgccg    180 taatgtttac cggagaaatc agtgtagaat aaacggattt ttccgtcaga tgtaaatgtg   240
gctgaacctg accattcttg tgtttggtct tttaggatag aatcatttgc atcgaatttg   300
tcgctgtctt taaagacgcg gccagcgttt tccagctgt caatagaagt ttcgccgact   360
ttttgataga acatgtaaat cgatgtgtca tccgcatttt taggatctcc ggctaatgca   420
```

-continued

```
aagacgatgt ggtagccgtg atagtttgcg acagtgccgt cagcgttttg taatggccag       480
ctgtcccaaa cgtccaggcc ttttgcagaa gagatatttt taattgtgga cgaatcaaat       540
tcagaaactt gatattttc attttttgc tgttcaggga tttgcagcat atcatggcgt         600
gtaatatggg aaatgccgta tgtttcctta tatggctttt ggttcgtttc tttcgcaaac       660
gcttgagttg cgcctcctgc cagcagtgcg gtagtaaagg ttaatactgt tgcttgtttt       720
gcaaactttt tgatgttcat cgttcatgtc tccttttta tgtactgtgt tagcggtctg        780
cttcttccag ccctcctgtt tgaagatggc aagttagtta cgcacaataa aaaaagacct      840
aaaatatgta aggggtgacg ccaaagtata cactttgccc tttacacatt ttaggtcttg       900
cctgctttat cagtaacaaa cccgcgcgat ttacttttcg acctcattct attagactct      960
cgtttggatt gcaactggtc tattttcctc ttttgtttga tagaaaatca taaaaggatt     1020
tgcagactac gggcctaaag aactaaaaaa tctatctgtt tcttttcatt ctctgtattt     1080
tttatagttt ctgttgcatg gcataaagt tgcctttta atcacaattc agaaaatatc       1140
ataatatctc atttcactaa ataatagtga acggcaggta tatgtgatgg gttaaaaagg    1200
atcggcggcc gctcgattta aatctcgaga ggcctgacgt cgggcccggt accacgcgtc     1260
atatgactag ttcggaccta gggatatcgt cgacatcgat gctcttctgc gttaattaac     1320
aattgggatc ctctagaccc gggatttaaa tcgctagcgg gctgctaaag gaagcggaac     1380
acgtagaaag ccagtccgca gaaacggtgc tgacccggga tgaatgtcag ctactgggct     1440
atctggacaa gggaaaacgc aagcgcaaag agaaagcagg tagcttgcag tgggcttaca     1500
tggcgatagc tagactgggc ggttttatgg acagcaagcg aaccggaatt gccagctggg     1560
gcgccctctg gtaaggttgg gaagcccgc aaagtaaact ggatggcttt cttgccgcca     1620
aggatctgat ggcgcagggg atcaagatct gatcaagaga caggatgagg atcgtttcgc     1680
atgattgaac aagatggatt gcacgcaggt tctccggccg cttgggtgga gaggctattc     1740
ggctatgact gggcacaaca gacaatcggc tgctctgatg ccgccgtgtt ccggctgtca     1800
gcgcaggggc gcccggttct ttttgtcaag accgacctgt ccggtgccct gaatgaactg     1860
caggacgagg cagcgcggct atcgtggctg gccacgacgg gcgttccttg cgcagctgtg     1920
ctcgacgttg tcactgaagc gggaagggac tggctgctat tgggcgaagt gccggggcag     1980
gatctcctgt catctcacct tgctcctgcc gagaaagtat ccatcatggc tgatgcaatg     2040
cggcggctga atacgcttga tccggctacc tgcccattcg accaccaagc gaaacatcgc     2100
atcgagcgag cacgtactcg gatggaagcc ggtcttgtcg atcaggatga tctggacgaa     2160
gagcatcagg ggctcgcgcc agccgaactg ttcgccaggc tcaaggcgcg catgcccgac     2220
ggcgaggatc tcgtcgtgac ccatggcgat gcctgcttgc cgaatatcat ggtggaaaat     2280
ggccgctttt ctggattcat cgactgtggc cggctgggtg tggcggaccg ctatcaggac     2340
atagcgttgg ctacccgtga tattgctgaa gagcttggcg gcgaatgggc tgaccgcttc     2400
ctcgtgcttt acggtatcgc cgctcccgat tcgcagcgca tcgccttcta tcgccttctt     2460
gacgagttct tctgagcggg actctgggt tcgaaatgac cgaccaagcg acgcccaacc     2520
tgccatcacg agatttcgat tccaccgccg ccttctatga aaggttgggc ttcggaatcg     2580
ttttccggga cgccggctgg atgatcctcc agcgcgggga tctcatgctg gagttcttcg     2640
cccacgctag cggcgcgccg gccggcccgg tgtgaaatac cgcacagatg cgtaaggaga     2700
aaataccgca tcaggcgctc ttccgcttcc tcgctcactg actcgctgcg ctcggtcgtt     2760
```

-continued

```
cggctgcggc gagcggtatc agctcactca aaggcggtaa tacgttatc cacagaatca    2820 ggggataacg caggaaagaa catgtgagca aaaggccagc aaaaggccag gaaccgtaaa    2880
aaggccgcgt tgctggcgtt tttccatagg ctccgccccc ctgacagca tcacaaaaat    2940 cgacgctcaa gtcagaggtg gcgaaacccg acaggactat aaagatacca ggcgtttccc    3000
cctggaagct ccctcgtgcg ctctcctgtt ccgaccctgc cgcttaccgg atacctgtcc    3060
gcctttctcc cttcgggaag cgtggcgctt tctcatagct cacgctgtag gtatctcagt    3120
tcggtgtagg tcgttcgctc caagctgggc tgtgtgcacg aaccccccgt tcagcccgac    3180
cgctgcgcct tatccggtaa ctatcgtctt gagtccaacc cggtaagaca cgacttatcg    3240
ccactggcag cagccactgg taacaggatt agcagagcga gtatgtagg cggtgctaca    3300 gagttcttga agtggtggcc taactacggc tacactagaa ggacagtatt tggtatctgc    3360
gctctgctga agccagttac cttcggaaaa agagttggta gctcttgatc cggcaaacaa    3420
accaccgctg gtagcggtgg tttttttgtt tgcaagcagc agattacgcg cagaaaaaaa    3480
ggatctcaag aagatccttt gatcttttct acggggtctg acgctcagtg aacgaaaac    3540 tcacgttaag ggattttggt catgagatta tcaaaaagga tcttcaccta gatccttta    3600 aaggccggcc gcggccgcca tcggcatttt cttttgcgtt tttatttgtt aactgttaat    3660
tgtccttgtt caaggatgct gtctttgaca acagatgttt tcttgccttt gatgttcagc    3720
aggaagctcg gcgcaaacgt tgattgtttg tctgcgtaga atcctctgtt tgtcatatag    3780
cttgtaatca cgacattgtt tcctttcgct tgaggtacag cgaagtgtga gtaagtaaag    3840
gttacatcgt taggatcaag atccattttt aacacaaggc cagttttgtt cagcggcttg    3900
tatgggccag ttaaagaatt agaaacataa ccaagcatgt aaatatcgtt agacgtaatg    3960
ccgtcaatcg tcatttttga tccgcgggag tcagtgaaca ggtaccattt gccgttcatt    4020
ttaaagacgt tcgcgcgttc aatttcatct gttactgtgt tagatgcaat cagcggtttc    4080 atcactttt tcagtgtgta atcatcgttt agctcaatca taccgagagc gccgtttgct    4140
aactcagccg tgcgtttttt atcgctttgc agaagttttt gactttcttg acggaagaat    4200
gatgtgcttt tgccatagta tgctttgtta aataaagatt cttcgccttg gtagccatct    4260
tcagttccag tgtttgcttc aaatactaag tatttgtggc ctttatcttc tacgtagtga    4320
gga                                                                  4323
```

<210> SEQ ID NO 67
<211> LENGTH: 35
<212> TYPE: DNA
<213> ORGANISM: Artificial sequence
<220> FEATURE:
<223> OTHER INFORMATION: Description of the artificial sequence: PCR
      Primer

<400> SEQUENCE: 67
gagagagaga cgcgtcccag tggctgagac gcatc                               35

<210> SEQ ID NO 68
<211> LENGTH: 34
<212> TYPE: DNA
<213> ORGANISM: Artificial sequence
<220> FEATURE:
<223> OTHER INFORMATION: Description of the artificial sequence: PCR
      Primer

<400> SEQUENCE: 68
ctctctctgt cgacgaattc aatcttacgg cctg                                34

<210> SEQ ID NO 69
<211> LENGTH: 5860
<212> TYPE: DNA
<213> ORGANISM: Artificial sequence
<220> FEATURE:
<223> OTHER INFORMATION: Description of the artificial sequence: plasmid

<400> SEQUENCE: 69

```
cccggtacca cgcgtcccag tggctgagac gcatccgcta aagccccagg aaccctgtgc      60
agaaagaaaa cactcctctg gctaggtaga cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat tagaaacgtc gctgaacgga tcgttgccac     240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt tccagggtgt taataaagaa cccgcgatg tcaccacgtt     600
gggtcgtggt ggttctgaca ccactgcagt tgcgttggca gctgctttga cgctgatgt     660
gtgtgagatt tactcggacg ttgacggtgt gtataccgct gacccgcgca tcgttcctaa     720
tgcacagaag ctggaaaagc tcagcttcga agaaatgctg gaacttgctg ctgttggctc     780
caagattttg tgctgcgca gtgttgaata cgctcgtgca ttcaatgtgc ccttcgcgt     840
acgctcgtct tatagtaatg atcccggcac tttgattgcc ggctctatgg aggatattcc     900
tgtggaagaa gcagtcctta ccggtgtcgc aaccgacaag tccgaagcca agtaaccgt     960
tctgggtatt tccgataagc caggcgaggc tgcgaaggtt ttccgtgcgt tggctgatgc    1020
agaaatcaac attgacatgg ttctgcagaa cgtctcttct gtagaagacg gcaccaccga    1080
catcaccttc acctgccctc gttccgacgg ccgccgcgcg atggagatct tgaagaagct    1140
tcaggttcag ggcaactgga ccaatgtgct ttacgacgac caggtcggca agtctccct    1200
cgtgggtgct ggcatgaagt ctcacccagg tgttaccgca gagttcatgg aagctctgcg    1260
cgatgtcaac gtgaacatcg aattgatttc cacctctgag attcgtattt ccgtgctgat    1320
ccgtgaagat gatctggatg ctgctgcacg tgcattgcat gagcagttcc agctgggcgg    1380
cgaagacgaa gccgtcgttt atgcaggcac cggacgctaa agttttaaag gagtagtttt    1440
acaatgacca ccatcgcagt tgttggtgca accggccagg tcggccaggt tatgcgcacc    1500
cttttggaag agcgcaattt cccagctgac actgttcgtt tctttgcttc cccacgttcc    1560
gcaggccgta agattgaatt cgtcgacatc gatgctcttc tgcgttaatt aacaattggg    1620
atcctctaga cccgggattt aaatcgctag cgggctgcta aggaagcgg aacacgtaga    1680
aagccagtcc gcagaaacgg tgctgacccc ggatgaatgt cagctactgg gctatctgga    1740
caagggaaaa cgcaagcgca aagagaaagc aggtagcttg cagtgggctt acatggcgat    1800
agctagactg gcggttttta tggacagcaa gcgaaccgga attgccagct ggggcgccct    1860
ctggtaaggt tgggaagccc tgcaaagtaa actggatggc tttcttgccg ccaaggatct    1920
gatggcgcag gggatcaaga tctgatcaag agacaggatg aggatcgttt cgcatgattg    1980
aacaagatgg attgcacgca ggttctccgg ccgcttgggt ggagaggcta ttcggctatg    2040
```

-continued

```
actgggcaca acagacaatc ggctgctctg atgccgccgt gttccggctg tcagcgcagg    2100
ggcgcccggt tcttttttgtc aagaccgacc tgtccggtgc cctgaatgaa ctgcaggacg    2160
aggcagcgcg gctatcgtgg ctggccacga cgggcgttcc ttgcgcagct gtgctcgacg    2220
ttgtcactga agcgggaagg gactggctgc tattgggcga agtgccgggg caggatctcc    2280
tgtcatctca ccttgctcct gccgagaaag tatccatcat ggctgatgca atgcggcggc    2340
tgcatacgct tgatccggct acctgcccat tcgaccacca agcgaaacat cgcatcgagc    2400
gagcacgtac tcggatggaa gccggtcttg tcgatcagga tgatctggac gaagagcatc    2460
aggggctcgc gccagccgaa ctgttcgcca ggctcaaggc gcgcatgccc gacggcgagg    2520
atctcgtcgt gacccatggc gatgcctgct tgccgaatat catggtggaa atggccgct    2580 tttctggatt catcgactgt ggccggctgg gtgtggcgga ccgctatcag acatagcgt    2640 tggctacccg tgatattgct gaagagcttg gcggcgaatg ggctgaccgc ttcctcgtgc    2700
tttacggtat cgccgctccc gattcgcagc gcatcgcctt ctatcgcctt cttgacgagt    2760
tcttctgagc gggactctgg ggttcgaaat gaccgaccaa gcgacgccca acctgccatc    2820
acgagatttc gattccaccg ccgccttcta tgaaaggttg ggcttcggaa tcgttttccg    2880
ggacgccggc tggatgatcc tccagcgcgg ggatctcatg ctggagttct cgcccacgc    2940 tagcggcgcg ccgccggcc cggtgtgaaa taccgcacag atgcgtaagg agaaaatacc    3000
gcatcaggcg ctcttccgct tcctcgctca ctgactcgct gcgctcggtc gttcggctgc    3060
ggcgagcggg atcagctcac tcaaaggcgg taatacggtt atccacagaa tcaggggata    3120
acgcaggaaa gaacatgtga gcaaaaggcc agcaaaaggc caggaaccgt aaaaaggccg    3180
cgttgctggc gtttttccat aggctccgcc cccctgacga gcatcacaaa aatcgacgct    3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta gaaggacagt atttggtatc tgcgctctgc    3660
tgaagccagt taccttcgga aaaagagttg gtagctcttg atccggcaaa caaaccaccg    3720
ctggtagcgg tggttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gtttttattt gttaactgtt aattgtcctt    3960
gttcaaggat gctgtctttg acaacagatg ttttcttgcc tttgatgttc agcaggaagc    4020
tcggcgcaaa cgttgattgt ttgtctgcgt agaatcctct gtttgtcata tagcttgtaa    4080
tcacgacatt gtttcctttc gcttgaggta cagcgaagtg tgagtaagta aaggttacat    4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc attttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
```

-continued

```
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggattttttcc gtcagatgta aatgtggctg    4860
aacctgacca ttcttgtgtt tggtctttta ggatagaatc atttgcatcg aatttgtcgc    4920
tgtctttaaa gacgcggcca gcgttttttcc agctgtcaat agaagtttcg ccgactttt    4980 gatagaacat gtaaatcgat gtgtcatccg catttttagg atctccggct aatgcaaaga    5040
cgatgtggta gccgtgatag tttgcgacag tgccgtcagc gttttgtaat ggccagctgt    5100
cccaaacgtc caggcctttt gcagaagaga tatttttaat tgtggacgaa tcaaattcag    5160
aaacttgata tttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340 acttttgat gttcatcgtt catgtctcct tttttatgta ctgtgttagc ggtctgcttc    5400
ttccagccct cctgtttgaa gatggcaagt tagttacgca caataaaaaa agacctaaaa    5460
tatgtaaggg gtgacgccaa agtatacact ttgcccttta cacattttag gtcttgcctg    5520
ctttatcagt aacaaacccg cgcgatttac ttttcgacct cattctatta gactctcgtt    5580
tggattgcaa ctggtctatt ttcctctttt gtttgataga aaatcataaa aggatttgca    5640
gactacgggc ctaaagaact aaaaaatcta tctgtttctt ttcattctct gtatttttta    5700
tagtttctgt tgcatgggca taaagttgcc ttttaatca caattcagaa aatatcataa    5760
tatctcattt cactaaataa tagtgaacgg caggtatatg tgatgggtta aaaaggatcg    5820
gcggccgctc gatttaaatc tcgagaggcc tgacgtcggg                          5860
```

<210> SEQ ID NO 70
<211> LENGTH: 38
<212> TYPE: DNA
<213> ORGANISM: Artificial sequence
<220> FEATURE:
<223> OTHER INFORMATION: Description of the artificial sequence: PCR
      Primer

<400> SEQUENCE: 70
cggcaccacc gacatcatct tcacctgccc tcgttccg                             38

<210> SEQ ID NO 71
<211> LENGTH: 38
<212> TYPE: DNA
<213> ORGANISM: Artificial sequence
<220> FEATURE:
<223> OTHER INFORMATION: Description of the artificial sequence: PCR
      Primer

<400> SEQUENCE: 71
cggaacgagg gcaggtgaag atgatgtcgg tggtgccg                             38

<210> SEQ ID NO 72
<211> LENGTH: 1266
<212> TYPE: DNA

<213> ORGANISM: LysC mutant
<220> FEATURE:
<221> NAME/KEY: CDS
<222> LOCATION: (1)..(1266)

<400> SEQUENCE: 72

| | | | | | | | | | | | | | | | | |
|---|---|---|---|---|---|---|---|---|---|---|---|---|---|---|---|---|
| gtg | gcc | ctg | gtc | gta | cag | aaa | tat | ggc | ggt | tcc | tcg | ctt | gag | agt | gcg | 48 |
| Val | Ala | Leu | Val | Val | Gln | Lys | Tyr | Gly | Gly | Ser | Ser | Leu | Glu | Ser | Ala | |
| 1 | | | | 5 | | | | | 10 | | | | | 15 | | |
| gaa | cgc | att | aga | aac | gtc | gct | gaa | cgg | atc | gtt | gcc | acc | aag | aag | gct | 96 |
| Glu | Arg | Ile | Arg | Asn | Val | Ala | Glu | Arg | Ile | Val | Ala | Thr | Lys | Lys | Ala | |
| | | | 20 | | | | | 25 | | | | | 30 | | | |
| gga | aat | gat | gtc | gtg | gtt | gtc | tgc | tcc | gca | atg | gga | gac | acc | acg | gat | 144 |
| Gly | Asn | Asp | Val | Val | Val | Val | Cys | Ser | Ala | Met | Gly | Asp | Thr | Thr | Asp | |
| | | 35 | | | | | 40 | | | | | 45 | | | | |
| gaa | ctt | cta | gaa | ctt | gca | gcg | gca | gtg | aat | ccc | gtt | ccg | cca | gct | cgt | 192 |
| Glu | Leu | Leu | Glu | Leu | Ala | Ala | Ala | Val | Asn | Pro | Val | Pro | Pro | Ala | Arg | |
| 50 | | | | | 55 | | | | | 60 | | | | | | |
| gaa | atg | gat | atg | ctc | ctg | act | gct | ggt | gag | cgt | att | tct | aac | gct | ctc | 240 |
| Glu | Met | Asp | Met | Leu | Leu | Thr | Ala | Gly | Glu | Arg | Ile | Ser | Asn | Ala | Leu | |
| 65 | | | | 70 | | | | | 75 | | | | | 80 | | |
| gtc | gcc | atg | gct | att | gag | tcc | ctt | ggc | gca | gaa | gcc | caa | tct | ttc | acg | 288 |
| Val | Ala | Met | Ala | Ile | Glu | Ser | Leu | Gly | Ala | Glu | Ala | Gln | Ser | Phe | Thr | |
| | | | | 85 | | | | | 90 | | | | | 95 | | |
| ggc | tct | cag | gct | ggt | gtg | ctc | acc | acc | gag | cgc | cac | gga | aac | gca | cgc | 336 |
| Gly | Ser | Gln | Ala | Gly | Val | Leu | Thr | Thr | Glu | Arg | His | Gly | Asn | Ala | Arg | |
| | | | 100 | | | | | 105 | | | | | 110 | | | |
| att | gtt | gat | gtc | act | cca | ggt | cgt | gtg | cgt | gaa | gca | ctc | gat | gag | ggc | 384 |
| Ile | Val | Asp | Val | Thr | Pro | Gly | Arg | Val | Arg | Glu | Ala | Leu | Asp | Glu | Gly | |
| | | 115 | | | | | 120 | | | | | 125 | | | | |
| aag | atc | tgc | att | gtt | gct | ggt | ttc | cag | ggt | gtt | aat | aaa | gaa | acc | cgc | 432 |
| Lys | Ile | Cys | Ile | Val | Ala | Gly | Phe | Gln | Gly | Val | Asn | Lys | Glu | Thr | Arg | |
| 130 | | | | | 135 | | | | | 140 | | | | | | |
| gat | gtc | acc | acg | ttg | ggt | cgt | ggt | ggt | tct | gac | acc | act | gca | gtt | gcg | 480 |
| Asp | Val | Thr | Thr | Leu | Gly | Arg | Gly | Gly | Ser | Asp | Thr | Thr | Ala | Val | Ala | |
| 145 | | | | | 150 | | | | | 155 | | | | | 160 | |
| ttg | gca | gct | gct | ttg | aac | gct | gat | gtg | tgt | gag | att | tac | tcg | gac | gtt | 528 |
| Leu | Ala | Ala | Ala | Leu | Asn | Ala | Asp | Val | Cys | Glu | Ile | Tyr | Ser | Asp | Val | |
| | | | | 165 | | | | | 170 | | | | | 175 | | |
| gac | ggt | gtg | tat | acc | gct | gac | ccg | cgc | atc | gtt | cct | aat | gca | cag | aag | 576 |
| Asp | Gly | Val | Tyr | Thr | Ala | Asp | Pro | Arg | Ile | Val | Pro | Asn | Ala | Gln | Lys | |
| | | | 180 | | | | | 185 | | | | | 190 | | | |
| ctg | gaa | aag | ctc | agc | ttc | gaa | gaa | atg | ctg | gaa | ctt | gct | gct | gtt | ggc | 624 |
| Leu | Glu | Lys | Leu | Ser | Phe | Glu | Glu | Met | Leu | Glu | Leu | Ala | Ala | Val | Gly | |
| | | 195 | | | | | 200 | | | | | 205 | | | | |
| tcc | aag | att | ttg | gtg | ctg | cgc | agt | gtt | gaa | tac | gct | cgt | gca | ttc | aat | 672 |
| Ser | Lys | Ile | Leu | Val | Leu | Arg | Ser | Val | Glu | Tyr | Ala | Arg | Ala | Phe | Asn | |
| | | 210 | | | | | 215 | | | | | 220 | | | | |
| gtg | cca | ctt | cgc | gta | cgc | tcg | tct | tat | agt | aat | gat | ccc | ggc | act | ttg | 720 |
| Val | Pro | Leu | Arg | Val | Arg | Ser | Ser | Tyr | Ser | Asn | Asp | Pro | Gly | Thr | Leu | |
| 225 | | | | | 230 | | | | | 235 | | | | | 240 | |
| att | gcc | ggc | tct | atg | gag | gat | att | cct | gtg | gaa | gaa | gca | gtc | ctt | acc | 768 |
| Ile | Ala | Gly | Ser | Met | Glu | Asp | Ile | Pro | Val | Glu | Glu | Ala | Val | Leu | Thr | |
| | | | | 245 | | | | | 250 | | | | | 255 | | |
| ggt | gtc | gca | acc | gac | aag | tcc | gaa | gcc | aaa | gta | acc | gtt | ctg | ggt | att | 816 |
| Gly | Val | Ala | Thr | Asp | Lys | Ser | Glu | Ala | Lys | Val | Thr | Val | Leu | Gly | Ile | |
| | | | 260 | | | | | 265 | | | | | 270 | | | |
| tcc | gat | aag | cca | ggc | gag | gct | gcg | aag | gtt | ttc | cgt | gcg | ttg | gct | gat | 864 |
| Ser | Asp | Lys | Pro | Gly | Glu | Ala | Ala | Lys | Val | Phe | Arg | Ala | Leu | Ala | Asp | |
| | | 275 | | | | | 280 | | | | | 285 | | | | |

```
gca gaa atc aac att gac atg gtt ctg cag aac gtc tct tct gta gaa      912
Ala Glu Ile Asn Ile Asp Met Val Leu Gln Asn Val Ser Ser Val Glu
290                 295                 300 gac ggc acc acc gac atc atc ttc acc tgc cct cgt tcc gac ggc cgc      960
Asp Gly Thr Thr Asp Ile Ile Phe Thr Cys Pro Arg Ser Asp Gly Arg
305                 310                 315                 320 cgc gcg atg gag atc ttg aag aag ctt cag gtt cag ggc aac tgg acc     1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct     1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg     1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt     1152
Arg Asp Val Asn Val Asn Ile Glu Leu Ile Ser Thr Ser Glu Ile Arg
370                 375                 380 att tcc gtg ctg atc cgt gaa gat gat ctg gat gct gct gca cgt gca     1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat     1248
Leu His Glu Gln Phe Gln Leu Gly Gly Glu Asp Glu Ala Val Val Tyr
                405                 410                 415 gca ggc acc gga cgc taa                                              1266
Ala Gly Thr Gly Arg
            420

<210> SEQ ID NO 73
<211> LENGTH: 421
<212> TYPE: PRT
<213> ORGANISM: LysC mutant

<400> SEQUENCE: 73

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190
```

```
Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
        290                 295                 300

Asp Gly Thr Thr Asp Ile Ile Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
            340                 345                 350

Gly Met Lys Ser His Pro Gly Val Thr Ala Glu Phe Met Glu Ala Leu
        355                 360                 365

Arg Asp Val Asn Val Asn Ile Glu Leu Ile Ser Thr Ser Glu Ile Arg
370                 375                 380

Ile Ser Val Leu Ile Arg Glu Asp Asp Leu Asp Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 74
<211> LENGTH: 5860
<212> TYPE: DNA
<213> ORGANISM: Artificial sequence
<220> FEATURE:
<223> OTHER INFORMATION: Description of the artificial sequence: plasmid

<400> SEQUENCE: 74
cccggtacca cgcgtcccag tggctgagac gcatccgcta aagccccagg aaccctgtgc      60
agaaagaaaa cactcctctg gctaggtaga cacagtttat aaaggtagag ttgagcgggt     120
aactgtcagc acgtagatcg aaaggtgcac aaaggtggcc ctggtcgtac agaaatatgg     180
cggttcctcg cttgagagtg cggaacgcat tagaaacgtc gctgaacgga tcgttgccac     240
caagaaggct ggaaatgatg tcgtggttgt ctgctccgca atgggagaca ccacggatga     300
acttctagaa cttgcagcgg cagtgaatcc cgttccgcca gctcgtgaaa tggatatgct     360
cctgactgct ggtgagcgta tttctaacgc tctcgtcgcc atggctattg agtcccttgg     420
cgcagaagcc caatctttca cgggctctca ggctggtgtg ctcaccaccg agcgccacgg     480
aaacgcacgc attgttgatg tcactccagg tcgtgtgcgt gaagcactcg atgagggcaa     540
gatctgcatt gttgctggtt tccagggtgt taataaagaa accgcgatgt caccacgtt     600 gggtcgtggt ggttctgaca ccactgcagt tgcgttggca gctgctttga acgctgatgt     660
gtgtgagatt tactcggacg ttgacggtgt gtataccgct gacccgcgca tcgttcctaa     720
```

```
tgcacagaag ctggaaaagc tcagcttcga agaaatgctg gaacttgctg ctgttggctc    780
caagattttg gtgctgcgca gtgttgaata cgctcgtgca ttcaatgtgc cacttcgcgt    840
acgctcgtct tatagtaatg atcccggcac tttgattgcc ggctctatgg aggatattcc    900
tgtggaagaa gcagtcctta ccggtgtcgc aaccgacaag tccgaagcca agtaaccgt    960
tctgggtatt tccgataagc caggcgaggc tgcgaaggtt ttccgtgcgt tggctgatgc   1020
agaaatcaac attgacatgg ttctgcagaa cgtctcttct gtagaagacg gcaccaccga   1080
catcatcttc acctgccctc gttccgacgg ccgccgcgcg atggagatct tgaagaagct   1140
tcaggttcag ggcaactgga ccaatgtgct ttacgacgac caggtcggca agtctccct   1200
cgtgggtgct ggcatgaagt ctcacccagg tgttaccgca gagttcatgg aagctctgcg   1260
cgatgtcaac gtgaacatcg aattgatttc cacctctgag attcgtattt ccgtgctgat   1320
ccgtgaagat gatctggatg ctgctgcacg tgcattgcat gagcagttcc agctgggcgg   1380
cgaagacgaa gccgtcgttt atgcaggcac cggacgctaa agttttaaag gagtagtttt   1440
acaatgacca ccatcgcagt tgttggtgca accggccagg tcggccaggt tatgcgcacc   1500
cttttggaag agcgcaattt cccagctgac actgttcgtt tctttgcttc cccacgttcc   1560
gcaggccgta agattgaatt cgtcgacatc gatgctcttc tgcgttaatt aacaattggg   1620
atcctctaga cccgggattt aaatcgctag cgggctgcta aggaagcgg aacacgtaga   1680
aagccagtcc gcagaaacgg tgctgacccc ggatgaatgt cagctactgg gctatctgga   1740
caagggaaaa cgcaagcgca aagagaaagc aggtagcttg cagtgggctt acatggcgat   1800
agctagactg ggcggtttta tggacagcaa gcgaaccgga attgccagct ggggcgccct   1860
ctggtaaggt tgggaagccc tgcaaagtaa actggatggc tttcttgccg ccaaggatct   1920
gatggcgcag gggatcaaga tctgatcaag agacaggatg aggatcgttt cgcatgattg   1980
aacaagatgg attgcacgca ggttctccgg ccgcttgggt ggagaggcta ttcggctatg   2040
actgggcaca acagacaatc ggctgctctg atgccgccgt gttccggctg tcagcgcagg   2100
ggcgcccggt tctttttgtc aagaccgacc tgtccggtgc cctgaatgaa ctgcaggacg   2160
aggcagcgcg gctatcgtgg ctggccacga cgggcgttcc ttgcgcagct gtgctcgacg   2220
ttgtcactga agcgggaagg gactggctgc tattgggcga agtgccgggg caggatctcc   2280
tgtcatctca ccttgctcct gccgagaaag tatccatcat ggctgatgca atgcggcggc   2340
tgcatacgct tgatccggct acctgcccat tcgaccacca agcgaaacat cgcatcgagc   2400
gagcacgtac tcggatggaa gccggtcttg tcgatcagga tgatctggac gaagagcatc   2460
aggggctcgc gccagccgaa ctgttcgcca ggctcaaggc gcgcatgccc gacggcgagg   2520
atctcgtcgt gacccatggc gatgcctgct tgccgaatat catggtggaa aatggccgct   2580
tttctggatt catcgactgt ggccggctgg gtgtggcgga ccgctatcag gacatagcgt   2640
tggctacccg tgatattgct gaagagcttg gcggcgaatg ggctgaccgc ttcctcgtgc   2700
tttacggtat cgccgctccc gattcgcagc gcatcgcctt ctatcgcctt cttgacgagt   2760
tcttctgagc gggactctgg ggttcgaaat gaccgaccaa gcgacgccca acctgccatc   2820
acgagatttc gattccaccg ccgccttcta tgaaaggttg gcttcggaa tcgttttccg   2880
ggacgccggc tggatgatcc tccagcgcgg ggatctcatg ctggagttct cgcccacgc   2940
tagcggcgcg ccggccggcc cggtgtgaaa taccgcacag atgcgtaagg agaaaatacc   3000
gcatcaggcg ctcttccgct tcctcgctca ctgactcgct gcgctcggtc gttcggctgc   3060
```

-continued

```
ggcgagcggt atcagctcac tcaaaggcgg taatacggtt atccacagaa tcagggata    3120
acgcaggaaa gaacatgtga gcaaaaggcc agcaaaaggc caggaaccgt aaaaaggccg    3180
cgttgctggc gttttccat aggctccgcc cccctgacga gcatcacaaa atcgacgct     3240
caagtcagag gtggcgaaac ccgacaggac tataaagata ccaggcgttt ccccctggaa    3300
gctccctcgt gcgctctcct gttccgaccc tgccgcttac cggatacctg tccgcctttc    3360
tcccttcggg aagcgtggcg ctttctcata gctcacgctg taggtatctc agttcggtgt    3420
aggtcgttcg ctccaagctg ggctgtgtgc acgaaccccc cgttcagccc gaccgctgcg    3480
ccttatccgg taactatcgt cttgagtcca acccggtaag acacgactta tcgccactgg    3540
cagcagccac tggtaacagg attagcagag cgaggtatgt aggcggtgct acagagttct    3600
tgaagtggtg gcctaactac ggctacacta aaggacagt atttggtatc tgcgctctgc    3660
tgaagccagt taccttcgga aaaagagttg gtagctcttg atccggcaaa caaaccaccg    3720
ctggtagcgg tggtttttttt gtttgcaagc agcagattac gcgcagaaaa aaaggatctc    3780
aagaagatcc tttgatcttt tctacggggt ctgacgctca gtggaacgaa aactcacgtt    3840
aagggatttt ggtcatgaga ttatcaaaaa ggatcttcac ctagatcctt ttaaaggccg    3900
gccgcggccg ccatcggcat tttcttttgc gttttttattt gttaactgtt aattgtcctt    3960
gttcaaggat gctgtctttg acaacagatg ttttcttgcc tttgatgttc agcaggaagc    4020
tcggcgcaaa cgttgattgt ttgtctgcgt agaatcctct gtttgtcata tagcttgtaa    4080
tcacgacatt gtttccttttc gcttgaggta cagcgaagtg tgagtaagta aaggttacat    4140
cgttaggatc aagatccatt tttaacacaa ggccagtttt gttcagcggc ttgtatgggc    4200
cagttaaaga attagaaaca taaccaagca tgtaaatatc gttagacgta atgccgtcaa    4260
tcgtcatttt tgatccgcgg gagtcagtga acaggtacca tttgccgttc atttaaaga    4320
cgttcgcgcg ttcaatttca tctgttactg tgttagatgc aatcagcggt ttcatcactt    4380
ttttcagtgt gtaatcatcg tttagctcaa tcataccgag agcgccgttt gctaactcag    4440
ccgtgcgttt tttatcgctt tgcagaagtt tttgactttc ttgacggaag aatgatgtgc    4500
ttttgccata gtatgctttg ttaaataaag attcttcgcc ttggtagcca tcttcagttc    4560
cagtgtttgc ttcaaatact aagtatttgt ggcctttatc ttctacgtag tgaggatctc    4620
tcagcgtatg gttgtcgcct gagctgtagt tgccttcatc gatgaactgc tgtacatttt    4680
gatacgtttt tccgtcaccg tcaaagattg atttataatc ctctacaccg ttgatgttca    4740
aagagctgtc tgatgctgat acgttaactt gtgcagttgt cagtgtttgt ttgccgtaat    4800
gtttaccgga gaaatcagtg tagaataaac ggattttttcc gtcagatgta aatgtggctg    4860
aacctgacca ttcttgtgtt tggtcttta ggatagaatc atttgcatcg aatttgtcgc    4920
tgtctttaaa gacgcggcca gcgttttttcc agctgtcaat agaagtttcg ccgactttt    4980
gatagaacat gtaaatcgat gtgtcatccg catttttagg atctccggct aatgcaaaga    5040
cgatgtggta gccgtgatag tttgcgacag tgccgtcagc gttttgtaat ggccagctgt    5100
cccaaacgtc caggcctttt gcagaagaga tattttaat tgtggacgaa tcaaattcag    5160
aaacttgata tttttcattt ttttgctgtt cagggatttg cagcatatca tggcgtgtaa    5220
tatgggaaat gccgtatgtt tccttatatg gcttttggtt cgtttctttc gcaaacgctt    5280
gagttgcgcc tcctgccagc agtgcggtag taaaggttaa tactgttgct tgttttgcaa    5340
actttttgat gttcatcgtt catgtctcct tttttatgta ctgtgttagc ggtctgcttc    5400
ttccagcccct cctgtttgaa gatggcaagt tagttacgca caataaaaaa agacctaaaa    5460
```

```
tatgtaaggg gtgacgccaa agtatacact ttgcccttta cacattttag gtcttgcctg      5520
ctttatcagt aacaaacccg cgcgatttac ttttcgacct cattctatta gactctcgtt      5580
tggattgcaa ctggtctatt ttcctctttt gtttgataga aaatcataaa aggatttgca      5640
gactacgggc ctaaagaact aaaaaatcta tctgtttctt ttcattctct gtattttta       5700 tagtttctgt tgcatgggca taaagttgcc ttttaatca caattcagaa aatatcataa       5760
tatctcattt cactaaataa tagtgaacgg caggtatatg tgatgggtta aaaaggatcg      5820
gcggccgctc gatttaaatc tcgagaggcc tgacgtcggg                            5860
```

<210> SEQ ID NO 75
<211> LENGTH: 32
<212> TYPE: DNA
<213> ORGANISM: Artificial sequence
<220> FEATURE:
<223> OTHER INFORMATION: Description of the artificial sequence: PCR primer

<400> SEQUENCE: 75

```
gagactcgag gtagacttta aacccatatt ag                                    32
```

<210> SEQ ID NO 76
<211> LENGTH: 29
<212> TYPE: DNA
<213> ORGANISM: Artificial sequence
<220> FEATURE:
<223> OTHER INFORMATION: Description of the artificial sequence: PCR primer

<400> SEQUENCE: 76

```
gaagtctaga ttagcgaata gcgtcgtgg                                        29
```

<210> SEQ ID NO 77
<211> LENGTH: 6142
<212> TYPE: DNA
<213> ORGANISM: Artificial sequence
<220> FEATURE:
<223> OTHER INFORMATION: Description of the artificial sequence: plasmid

<400> SEQUENCE: 77

```
tcgaggtaga ctttaaaccc atattagagg gtgggggcgc agctaagcca agagctaaga      60
aaactagggg acatagtggt atcgacgctg ttcaataacg gcaacctaca gtaaaaatga      120
ataaaattcc tcaaggtggc aatattcttc aattttccca taaaatacgc ccgtatgtct      180
gcacaaccgc tacctgctgc gtatcagcgc acaatcaccg atgtcatttc catgccaaca      240
ccgggccagg ttccgttttc tgtagagttt atgccgccac gagatgaggc agcagaagag      300
cgactctgga aagccgccga agcatttcac gacttaggag cctcttttgt ctccgttact      360
tatggtgcag gcggatctag ccgcgagcgc acaatgcgtg tcgcgcacaa gctttctcgt      420
catccgttga ccacgctcgt tcatctcacg cttgtggaac acacccaaga agaattagaa      480
gaaattctgt gcacttatgc gtcccacggg ttgtctaact tacttgcctt gcgaggcgat      540
ccccctggca ctgacccgat ggctccgtgg gtccctaccg caggcggcct agattatgcc      600
aaagatttga tcgacctcgt gcgcaagact gagcagacct cgcactttca ggtaggaatt      660 gctagttttcc cagaagggca ctaccgagcg cctagcattg aggcggatac gcaatttaca      720
ttggaaaagc tgcgagctgg cgcagagttt cgattaccc agatgttttt tgatgtcgat      780
cactatttac gactgcgaga tcgcttggtt aaggcggatc ctgaacatgg atcaaagccg      840
```

```
atcatcccag gacttatgcc cattaccagc ttgaggtcgg ttcgtaggca gatggaatta      900
gcaggtgcca ccttgcctaa ggctttagaa aaacggcttc tcgacgcagc gcgcggcgat      960
gaggaagctc atcgcggcga tattcgcaaa gtaggaatcg aagtcactac tgagatggca     1020
cagcgtctta tttctgaagg gatcccagac atccatttca tgaccatgaa ttatgttcga     1080
gcgacccaag aagtactcca taatctcggc atggcgcccg cgtggggaac acagcaaggc     1140
cacgacgcta ttcgctaatc tagacccggg atttaaatcg ctagcgggct gctaaaggaa     1200
gcggaacacg tagaaagcca gtccgcagaa acggtgctga ccccggatga atgtcagcta     1260
ctgggctatc tggacaaggg aaaacgcaag cgcaaagaga aagcaggtag cttgcagtgg     1320
gcttacatgg cgatagctag actgggcggt tttatggaca gcaagcgaac cggaattgcc     1380
agctggggcg ccctctggta aggttgggaa gccctgcaaa gtaaactgga tggctttctt     1440
gccgccaagg atctgatggc gcagggatc aagatctgat caagagacag gatgaggatc     1500
gtttcgcatg attgaacaag atggattgca cgcaggttct ccggccgctt gggtggagag     1560
gctattcggc tatgactggg cacaacagac aatcggctgc tctgatgccg ccgtgttccg     1620
gctgtcagcg caggggcgcc cggttctttt tgtcaagacc gacctgtccg gtgccctgaa     1680
tgaactgcag gacgaggcag cgcggctatc gtggctggcc acgacgggcg ttccttgcgc     1740
agctgtgctc gacgttgtca ctgaagcggg aagggactgg ctgctattgg gcgaagtgcc     1800
ggggcaggat ctcctgtcat ctcaccttgc tcctgccgag aaagtatcca tcatggctga     1860
tgcaatgcgg cggctgcata cgcttgatcc ggctacctgc ccattcgacc accaagcgaa     1920
acatcgcatc gagcgagcac gtactcggat ggaagccggt cttgtcgatc aggatgatct     1980
ggacgaagag catcagggc tcgcgccagc cgaactgttc gccaggctca aggcgcgcat     2040
gcccgacggc gaggatctcg tcgtgaccca tggcgatgcc tgcttgccga atatcatggt     2100
ggaaaatggc cgcttttctg gattcatcga ctgtggccgg ctgggtgtgg cggaccgcta     2160
tcaggacata gcgttggcta cccgtgatat tgctgaagag cttggcggcg aatgggctga     2220
ccgcttcctc gtgctttacg gtatcgccgc tcccgattcg cagcgcatcg ccttctatcg     2280
ccttcttgac gagttcttct gagcgggact ctggggttcg aaatgaccga ccaagcgacg     2340
cccaacctgc catcacgaga tttcgattcc accgccgcct tctatgaaag gttgggcttc     2400
ggaatcgttt tccgggacgc cggctggatg atcctccagc gcgggatct catgctggag      2460
ttcttcgccc acgctagcgg cgcgccggcc ggcccggtgt gaaataccgc acagatgcgt     2520
aaggagaaaa taccgcatca gccgctcttc cgcttcctcg ctcactgact cgctgcgctc     2580
ggtcgttcgg ctgcggcgag cggtatcagc tcactcaaag gcggtaatac ggttatccac     2640
agaatcaggg gataacgcag gaaagaacat gtgagcaaaa ggccagcaaa aggccaggaa     2700
ccgtaaaaag gccgcgttgc tggcgttttt ccataggctc cgcccccctg acgagcatca     2760
caaaaatcga cgctcaagtc agaggtggcg aaacccgaca ggactataaa gataccaggc     2820
gtttccccct ggaagctccc tcgtgcgctc tcctgttccg accctgccgc ttaccggata     2880
cctgtccgcc tttctccctt cgggaagcgt ggcgctttct catagctcac gctgtaggta     2940
tctcagttcg gtgtaggtcg ttcgctccaa gctgggctgt gtgcacgaac cccccgttca     3000
gcccgaccgc tgcgccttat ccggtaacta tcgtcttgag tccaacccgg taagacacga     3060
cttatcgcca ctggcagcag ccactggtaa caggattagc agagcgaggt atgtaggcgg     3120
tgctacagag ttcttgaagt ggtggcctaa ctacggctac actagaagga cagtatttgg     3180
tatctgcgct ctgctgaagc cagttacctt cggaaaaaga gttggtagct cttgatccgg     3240
```

```
caaacaaacc accgctggta gcggtggttt ttttgtttgc aagcagcaga ttacgcgcag   3300
aaaaaaagga tctcaagaag atcctttgat cttttctacg gggtctgacg ctcagtggaa   3360
cgaaaactca cgttaaggga ttttggtcat gagattatca aaaaggatct tcacctagat   3420
cctttttaaag gccggccgcg gccgcgcaaa gtcccgcttc gtgaaaattt tcgtgccgcg   3480
tgattttccg ccaaaaactt taacgaacgt tcgttataat ggtgtcatga ccttcacgac   3540
gaagtactaa aattggcccg aatcatcagc tatggatctc tctgatgtcg cgctggagtc   3600
cgacgcgctc gatgctgccg tcgatttaaa acggtgatc  ggattttttcc gagctctcga   3660
tacgacggac gcgccagcat cacgagactg ggccagtgcc gcgagcgacc tagaaactct   3720
cgtggcggat cttgaggagc tggctgacga gctgcgtgct cggccagcgc caggaggacg   3780
cacagtagtg gaggatgcaa tcagttgcgc ctactgcggt ggcctgattc ctccccggcc   3840
tgacccgcga ggacggcgcg caaaatattg ctcagatgcg tgtcgtgccg cagccagccg   3900
cgagcgcgcc aacaaacgcc acgccgagga gctggaggcg gctaggtcgc aaatggcgct   3960
ggaagtgcgt cccccgagcg aaattttggc catggtcgtc acagagctgg aagcggcagc   4020
gagaattatc gcgatcgtgg cggtgcccgc aggcatgaca aacatcgtaa atgccgcgtt   4080
tcgtgtgccg tggccgccca ggacgtgtca gcgccgccac cacctgcacc gaatcggcag   4140
cagcgtcgcg cgtcgaaaaa gcgcacaggc ggcaagaagc gataagctgc acgaatacct   4200
gaaaaatgtt gaacgccccg tgagcggtaa ctcacagggc gtcggctaac ccccagtcca   4260
aacctgggag aaagcgctca aaaatgactc tagcggattc acgagacatt gacacaccgg   4320
cctggaaatt ttccgctgat ctgttcgaca cccatcccga gctcgcgctg cgatcacgtg   4380
gctggacgag cgaagaccgc cgcgaattcc tcgctcacct gggcagagaa aatttccagg   4440
gcagcaagac ccgcgacttc gccagcgctt ggatcaaaga cccggacacg gagaaacaca   4500
gccgaagtta taccgagttg gttcaaaatc gcttgcccgg tgccagtatg ttgctctgac   4560
gcacgcgcag cacgcagccg tgcttgtcct ggacattgat gtgccgagcc accaggccgg   4620
cgggaaaatc gagcacgtaa accccgaggt ctacgcgatt ttggagcgct gggcacgcct   4680
ggaaaaagcg ccagcttgga tcggcgtgaa tccactgagc gggaaatgcc agctcatctg   4740
gctcattgat ccggtgtatg ccgcagcagg catgagcagc ccgaatatgc gcctgctggc   4800
tgcaacgacc gaggaaatga cccgcgtttt cggcgctgac caggcttttt cacataggct   4860
gagccgtggc cactgcactc tccgacgatc ccagccgtac cgctggcatg cccagcacaa   4920
tcgcgtggat cgcctagctg atcttatgga ggttgctcgc atgatctcag gcacagaaaa   4980
acctaaaaaa cgctatgagc aggagttttc tagcggacgg gcacgtatcg aagcggcaag   5040
aaaagccact gcggaagcaa aagcacttgc cacgcttgaa gcaagcctgc cgagcgccgc   5100
tgaagcgtct ggagagctga tcgacggcgt ccgtgtcctc tggactgctc cagggcgtgc   5160
cgcccgtgat gagacggctt ttcgccacgc tttgactgtg ggataccagt taaaagcggc   5220
tggtgagcgc ctaaaagaca ccaagggtca tcgagcctac gagcgtgcct acaccgtcgc   5280
tcaggcggtc ggaggaggcc gtgagcctga tctgccgccg gactgtgacc gccagacgga   5340
ttggccgcga cgtgtgcgcg gctacgtcgc taaaggccag ccagtcgtcc ctgctcgtca   5400
gacagagacg cagagccagc cgaggcgaaa agctctggcc actatgggaa gacgtggcgg   5460
taaaaaggcc gcagaacgct ggaaagaccc aacagtgag  tacgcccgag cacagcgaga   5520
aaaactagct aagtccagtc aacgacaagc taggaaagct aaaggaaatc gcttgaccat   5580
```

-continued

```
tgcaggttgg tttatgactg ttgagggaga gactggctcg tggccgacaa tcaatgaagc    5640
tatgtctgaa tttagcgtgt cacgtcagac cgtgaataga gcacttaagg tctgcgggca    5700
ttgaacttcc acgaggacgc cgaaagcttc ccagtaaatg tgccatctcg taggcagaaa    5760
acggttcccc cgtagggtct ctctcttggc ctcctttcta ggtcgggctg attgctcttg    5820
aagctctcta gggggggctca caccataggc agataacgtt ccccaccggc tcgcctcgta    5880
agcgcacaag gactgctccc aaagatcttc aaagccactg ccgcgactgc cttcgcgaag    5940
ccttgccccg cggaaatttc ctccaccgag ttcgtgcaca ccctatgcc aagcttcttt    6000 caccctaaat tcgagagatt ggattcttac cgtggaaatt cttcgcaaaa atcgtcccct    6060
gatcgccctt gcgacgttgg cgtcggtgcc gctggttgcg cttggcttga ccgacttgat    6120
cagcggccgc tcgatttaaa tc                                             6142
```